US007960615B2

(12) United States Patent
Peters et al.

(10) Patent No.: US 7,960,615 B2
(45) Date of Patent: Jun. 14, 2011

(54) GRG36: NOVEL EPSP SYNTHASE GENE CONFERRING HERBICIDE RESISTANCE

(75) Inventors: Cheryl Peters, Raleigh, NC (US); Brian Vande Berg, Durham, NC (US); Brian Carr, Raleigh, NC (US); Daniel John Tomso, Bahama, NC (US)

(73) Assignee: Athenix Corp., Morrisville, NC (US)

( * ) Notice: Subject to any disclaimer, the term of this patent is extended or adjusted under 35 U.S.C. 154(b) by 823 days.

(21) Appl. No.: 11/769,327

(22) Filed: Jun. 27, 2007

(65) Prior Publication Data

US 2007/0300326 A1 Dec. 27, 2007

Related U.S. Application Data

(60) Provisional application No. 60/816,676, filed on Jun. 27, 2006, provisional application No. 60/819,122, filed on Jul. 7, 2006, provisional application No. 60/819,119, filed on Jul. 7, 2006.

(51) Int. Cl.
*C12N 15/82* (2006.01)
*C12N 15/52* (2006.01)

(52) U.S. Cl. .................. 800/300; 435/252.3; 435/320.1; 435/419; 536/23.2; 800/288; 800/295

(58) Field of Classification Search ........................ None
See application file for complete search history.

(56) References Cited

U.S. PATENT DOCUMENTS

| | | | |
|---|---|---|---|
| 2003/0233675 | A1 | 12/2003 | Cao et al. |
| 2006/0150270 | A1 | 7/2006 | Hammer et al. |
| 2006/0253921 | A1 | 11/2006 | Carozzi et al. |

FOREIGN PATENT DOCUMENTS

WO WO 2006/110586 A2 10/2006

OTHER PUBLICATIONS

Takami et al 2000 Nucleic Acids Research 28(21): 4317-4331.*
Uniprot Database Report for accession No. Q9K9D5, Direct Submission Oct. 1, 2000.
Geneseq Database Report for accession No. ADT42596, Direct Submission Dec. 2, 2004.
Pipke, R. et al. "Isolation and Characterization of a Mutant of *Athrobacter* sp. Strain GLP—1 Which Utilizes the Herbicide Glyphosate as Its Sole Source of Phosphorus and Nitrogen," Applied and Environmental Microbiology, Nov. 1998, pp. 2868-2870 vol. 54, No. 11.
Sun, Yi-Cheng et al. "Novel AroA with High Tolerance to Glyphosate, Encoded by a Gene of *Pseudomonas putida* 4G-1 Isolated from an Extremely Polluted Environment in China," Applied and Environmental Microbiology, Aug. 2005, pp. 4771-4776 vol. 71, No. 8.
Takami et al. "Complete genome sequesnce of the alkaliphilic bacterium *Bacillus halodurans* and genomic sequence comparison with *Bacillus subtilis*," Nucleic Acids Research, 2000, pp. 4317-4331 vol. 28, No. 21.
NCBI Database Report for Accession No. BAB06432, Direct Submission on Mar. 22, 2000.
NCBI Database Report for Accession No. BAD63759, Direct Submission on Oct. 19, 2003.
NCBI Database Report for Accession No. NP_629359, Direct Submission on May 28, 2002.
NCBI Database Report for Accession No. NP_824218, Direct Submission on Apr. 8, 2002.
NCBI Database Report for Accession No. ZP_00413033, Direct Submission on Jun. 1, 2005.

* cited by examiner

*Primary Examiner* — David H Kruse
(74) *Attorney, Agent, or Firm* — Destiny M. Davenport

(57) ABSTRACT

Compositions and methods for conferring herbicide resistance to bacteria, plants, plant cells, tissues and seeds are provided. Compositions include nucleic acid molecules encoding herbicide resistance or tolerance polypeptides, vectors comprising those nucleic acid molecules, and host cells comprising the vectors. The nucleotide sequences of the invention can be used in DNA constructs or expression cassettes for transformation and expression in organisms, including microorganisms and plants. Compositions also comprise transformed bacteria, plants, plant cells, tissues, and seeds. In particular, the present invention provides for isolated nucleic acid molecules comprising the nucleotide sequence set forth in SEQ ID NO:1, 3, 4, 6, 7, 9, 10, 12, 13, 15, 17, 18, 20, 21, or 23, a nucleotide sequence encoding the amino acid sequence shown in SEQ ID NO:2, 5, 8, 11, 14, 16, 19, or 22, the herbicide resistance nucleotide sequence deposited in a bacterial host as Accession Nos. NRRL B-30932, B-30933, B-30934, B-30945, B-30946, B-30947, or B-30948, as well as variants and fragments thereof.

15 Claims, 8 Drawing Sheets

GRG36: NOVEL EPSP SYNTHASE GENE CONFERRING HERBICIDE RESISTANCE

CROSS REFERENCE TO RELATED APPLICATION

This application claims the benefit of U.S. Provisional Application Ser. Nos. 60/816,676, filed Jun. 27, 2006; 60/819,122, filed Jul. 7, 2006; and, 60/819,119, filed Jul. 7, 2006, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "325059_SequenceListing.txt", created on Jun. 25, 2007, and having a size of 150 kilobytes and is filed concurrently with the specification. The sequence listing contained in this ASCII formatted document is part of the specification and is herein incorporated by reference in its entirety.

FIELD OF THE INVENTION

This invention provides novel genes encoding 5-enolpyruvylshikimate-3-phosphate (EPSP) synthase that provide herbicide resistance. These genes are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have a high tolerance to glyphosate.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945).

U.S. Pat. No. 6,040,497 reports mutant maize EPSP synthase enzymes having substitutions of threonine to isoleucine at position 102 and proline to serine at position 106 (the "TIPS" mutation). Such alterations confer glyphosate resistance upon the maize enzyme. A mutated EPSP synthase from *Salmonella typhimurium* strain CT7 confers glyphosate resistance in bacterial cells, and is reported to confer glyphosate resistance upon plant cells (U.S. Pat. Nos. 4,535,060; 4,769,061; and 5,094,945). He et al. ((2001) *Biochim et Biophysica Acta* 1568:1-6) have developed EPSP synthases with increased glyphosate tolerance by mutagenesis and recombination between the *E. coli* and *Salmonella typhimurium* EPSP synthase genes, and suggest that mutations at position 42 (T42M) and position 230 (Q230K) are likely responsible for the observed resistance.

Subsequent work (He et al. (2003) *Biosci. Biotech. Biochem.* 67:1405-1409) shows that the T42M mutation (threonine to methionine) is sufficient to improve tolerance of both the *E. coli* and *Salmonella typhimurium* enzymes. These enzymes contain amino acid substitutions in their active sites that prevent the binding of glyphosate without affecting binding by PEP or S3P. Mutations that occur in the hinge region between the two globular domains of EPSP synthase have been shown to alter the binding affinity of glyphosate but not PEP (He et al., 2003, supra). Therefore, such enzymes have high catalytic activity, even in the presence of glyphosate.

Due to the many advantages herbicide resistance plants provide, methods for identifying herbicide resistance genes with glyphosate resistance activity are desirable.

SUMMARY OF INVENTION

Compositions and methods for conferring herbicide resistance or tolerance to bacteria, plants, plant cells, tissues and seeds are provided. Compositions include nucleic acid molecules encoding herbicide resistance or tolerance polypeptides, vectors comprising those nucleic acid molecules, and host cells comprising the vectors. Compositions also include antibodies to the herbicide resistance or tolerance polypeptides. As noted the nucleotide sequences of the invention can be used in DNA constructs or expression cassettes for transformation and expression in organisms, including microorganisms and plants. Compositions also comprise transformed bacteria, plants, plant cells, tissues, and seeds. In addition, methods are provided for producing the polypeptides encoded by the synthetic nucleotides of the invention.

In particular, isolated nucleic acid molecules and variants thereof encoding herbicide resistance- or tolerance polypeptides are provided. Additionally, amino acid sequences and variants thereof encoded by the polynucleotides that confer herbicide resistance or tolerance are encompassed. In particular, the present invention provides for isolated nucleic acid molecules comprising the nucleotide sequence set forth in SEQ ID NO:1, 3, 4, 6, 7, 9, 10, 12, 13, 15, 17, 18, 20, 21, or 23, a nucleotide sequence encoding the amino acid sequence shown in SEQ ID NO:2, 5, 8, 11, 14, 16, 19, or 22, the herbicide resistance nucleotide sequence deposited in a bacterial host as Accession Nos. NRRL B-30932, B-30933, B-30934, B-30945, B-30946, B-30947, or B-30948, as well as variants and fragments thereof. Nucleotide sequences that are complementary to a nucleotide sequence of the invention, or that hybridize to a sequence of the invention or a complement of a sequence of the invention are also encompassed.

DETAILED DESCRIPTION

Figure 1A:
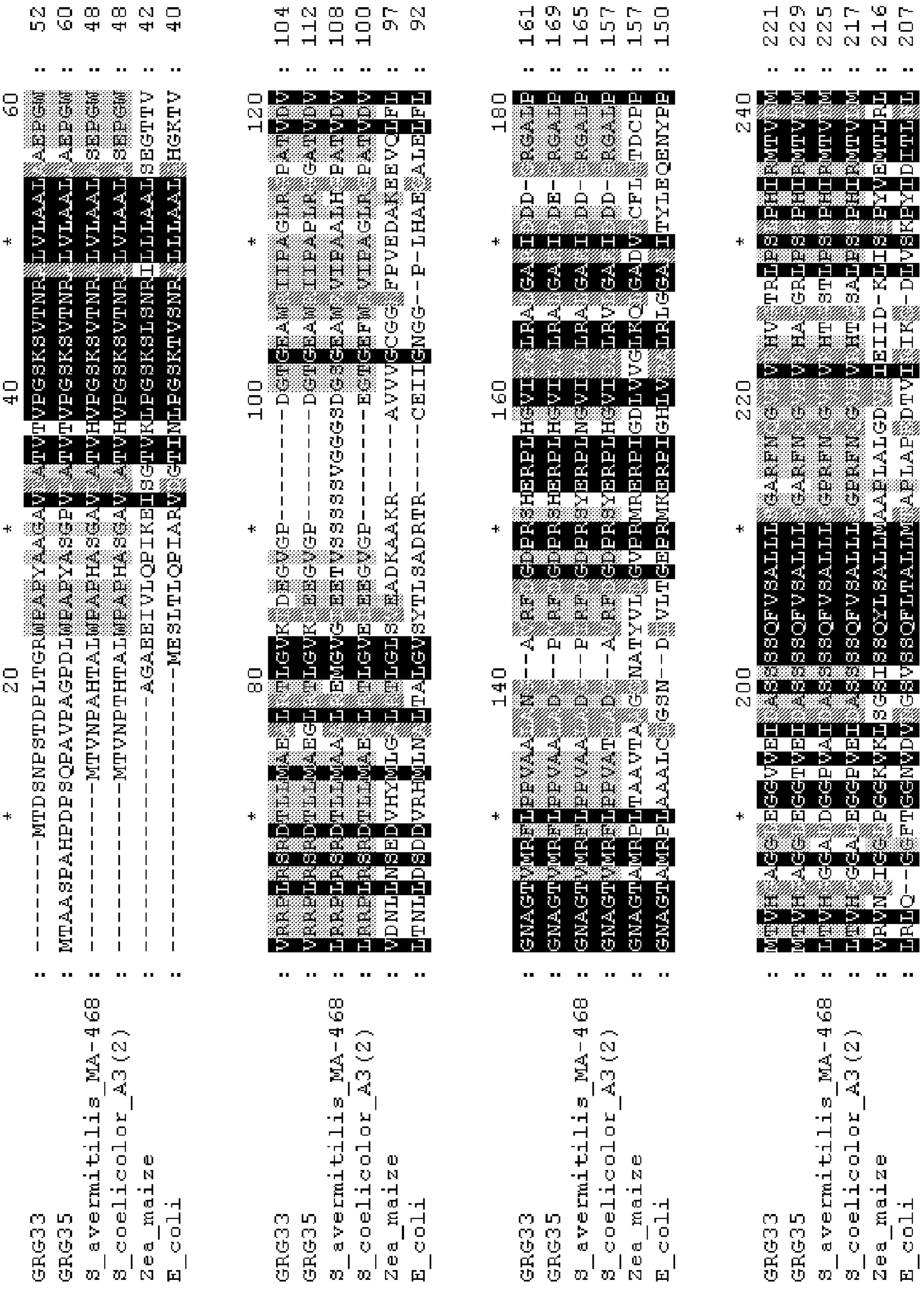
FIG. 1 shows an alignment of the amino acid sequence of GRG33 (SEQ ID NO:2) and GRG35 (SEQ ID NO:5) with EPSP synthase sequences from *Streptomyces cooelicolor* (SEQ ID NO:24), *Streptomyces avermitilis* (SEQ ID NO:25), *Zea mays* (SEQ ID NO:38), and *E. coli* (SEQ ID NO:37). The alignment shows the most highly conserved amino acid residues highlighted in black and highly conserved amino acid residues highlighted in gray.

The present invention is drawn to compositions and methods for regulating herbicide resistance in organisms, particularly in plants or plant cells. The methods involve transforming organisms with a nucleotide sequence encoding a glyphosate resistance gene of the invention. In particular, a nucleotide sequence of the invention is useful for preparing plants that show increased tolerance to the herbicide glyphosate. Thus, transformed bacteria, plants, plant cells, plant tissues and seeds are provided. Compositions include nucleic acids and proteins relating to herbicide tolerance in microorganisms and plants as well as transformed bacteria, plants, plant tissues and seeds. More particularly, nucleotide sequences of the glyphosate resistance genes (grg33, syngrg33, grg35, syngrg35, grg36, syngrg36, grg37, syngrg37, grg38, syngrg38, grg39, syngrg39, grg50, syngrg50) and the amino acid sequences of the proteins encoded thereby are disclosed. The sequences find use in the construction of expression vectors for subsequent transformation into plants of interest, as probes for the isolation of other glyphosate resistance genes, as selectable markers, and the like. Thus, by "glyphosate resistance gene of the invention" is intended the nucleotide sequence set forth in SEQ ID NO:1, 3, 4, 6, 7, 9, 10, 12, 13, 15, 17, 18, 20, 21, or 23, and fragments and variants thereof that encode a glyphosate resistance or tolerance polypeptide. Likewise, a "glyphosate resistance polypeptide of the invention" is a polypeptide having the amino acid sequence set forth in SEQ ID NO:2, 5, 8, 11, 14, 16, 19, or 22, and fragments and variants thereof that confer glyphosate resistance or tolerance to a host cell.

Plasmids containing the herbicide resistance nucleotide sequences of the invention were deposited in the permanent collection of the Agricultural Research Service Culture Collection, Northern Regional Research Laboratory (NRRL), 1815 North University Street, Peoria, Ill. 61604, United States of America, on Jun. 9, 2006, and assigned Accession Nos. NRRL B-30932 (for grg33), NRRL B-30933 (for grg35), and NRRL B-30934 (for grg36); and on Jun. 26, 2006, and assigned Accession Nos. NRRL B-30945 (for grg37), NRRL B-30946 (for grg38), NRRL B-30947 (for grg39), and NRRL B-30948 (for grg50). This deposit will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposit with the ATCC. This deposit was made merely as a convenience for those of skill in the art and is not an admission that a deposit is required under 35 U.S.C. §112.

By "glyphosate" is intended any herbicidal form of N-phosphonomethylglycine (including any salt thereof) and other forms that result in the production of the glyphosate anion in planta. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. A "glyphosate resistance protein" includes a protein that confers upon a cell the ability to tolerate a higher concentration of glyphosate than cells that do not express the protein, or to tolerate a certain concentration of glyphosate for a longer period of time than cells that do not express the protein. By "tolerate" or "tolerance" is intended either to survive, or to carry out essential cellular functions such as protein synthesis and respiration in a manner that is not readily discernable from untreated cells.

Isolated Nucleic Acid Molecules, and Variants and Fragments Thereof

One aspect of the invention pertains to isolated or recombinant nucleic acid molecules comprising nucleotide sequences encoding herbicide resistance proteins and polypeptides or biologically active portions thereof, as well as nucleic acid molecules sufficient for use as hybridization probes to identify herbicide resistance-encoding nucleic acids. As used herein, the term "nucleic acid molecule" is intended to include DNA molecules (e.g., cDNA, recombinant DNA, or genomic DNA) and RNA molecules (e.g., mRNA) and analogs of the DNA or RNA generated using nucleotide analogs. The nucleic acid molecules can be single-stranded or double-stranded, but preferably are double-stranded DNA.

Nucleotide sequences encoding the proteins of the present invention include the sequences set forth in SEQ ID NO:1, 3, 4, 6, 7, 9, 10, 12, 13, 15, 17, 18, 20, 21, or 23, the herbicide resistance nucleotide sequence deposited in a bacterial host as Accession Nos. NRRL B-30932, B-30933, B-30934, B-30945, B-30946, B-30947, or B-30948, and variants, fragments, and complements thereof. By "complement" is intended a nucleotide sequence that is sufficiently complementary to a given nucleotide sequence such that it can hybridize to the given nucleotide sequence to thereby form a stable duplex. In some embodiments, the complement hybridizes across the full length of the sequence of the invention. In another embodiment, the complement hybridizes across at least about 50% of the sequence of the invention, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% of a sequence of the invention. The corresponding amino acid sequences for the herbicide resistance proteins encoded by these nucleotide sequences are set forth in SEQ ID NO:2, 5, 8, 11, 14, 16, 19, or 22. The invention also encompasses nucleic acid molecules comprising nucleotide sequences encoding partial-length herbicide resistance proteins, and complements thereof.

In some embodiments, the polynucleotides of the present invention encode polypeptides that are Class III EPSP synthase enzymes. For the purposes of the present invention, a "Class III EPSP synthase enzyme" is an herbicide tolerant or herbicide resistant polypeptide containing one or more of the amino acid sequence domains described in U.S. patent application Ser. No. 11/400,598, which is herein incorporated by reference in its entirety.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. An herbicide resistance protein that is substantially free of cellular material includes preparations of protein having less than about 30%, 20%, 10%, or 5% (by dry weight) of non-herbicide resistance protein (also referred to herein as a "contaminating protein").

Nucleic acid molecules that are fragments of these herbicide resistance-encoding nucleotide sequences are also encompassed by the present invention. By "fragment" is intended a portion of a nucleotide sequence encoding an herbicide resistance protein. A fragment of a nucleotide sequence may encode a biologically active portion of an herbicide resistance protein, or it may be a fragment that can be used as a hybridization probe or PCR primer using methods disclosed below. Nucleic acid molecules that are fragments of an herbicide resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450 contiguous nucleotides, or up to the number of nucleotides present in a full-length herbicide resistance-encoding nucleotide sequence disclosed herein (for example, 1329 nucleotides for SEQ ID NO:1; 1353 nucleotides for SEQ ID NO:4; 1344 nucleotides for SEQ ID NO:7, etc) depending upon the intended use. By "contiguous" nucleotides is intended nucleotide residues that are immediately adjacent to one another.

Fragments of the nucleotide sequences of the present invention generally will encode protein fragments that retain the biological activity of the full-length glyphosate resistance protein; i.e., herbicide-resistance activity. By "retains herbicide resistance activity" is intended that the fragment will have at least about 30%, at least about 50%, at least about 70%, or at least about 80% of the herbicide resistance activity of the full-length glyphosate resistance protein disclosed herein as SEQ ID NO:2, 5, 8, 11, 14, 16, 19, or 22. Methods for measuring herbicide resistance activity are well known in the art. See, for example, U.S. Pat. Nos. 4,535,060, and 5,188,642, each of which are herein incorporated by reference in their entirety.

A fragment of an herbicide resistance-encoding nucleotide sequence that encodes a biologically active portion of a protein of the invention will encode at least about 15, 25, 30, 50, 75, 100, 125, 150, 175, 200, 250, 300, 350, 400 contiguous amino acids, or up to the total number of amino acids present in a full-length herbicide resistance protein of the invention (for example, 442 amino acids for SEQ ID NO:2; 450 for SEQ ID NO:5; 447 amino acids for SEQ ID NO:8, etc).

Preferred herbicide resistance proteins of the present invention are encoded by a nucleotide sequence sufficiently identical to the nucleotide sequence of SEQ ID NO:1, 3, 4, 6, 7, 9, 10, 12, 13, 15, 17, 18, 20, 21, or 23. The term "sufficiently identical" is intended an amino acid or nucleotide sequence that has at least about 60% or 65% sequence identity, about 70% or 75% sequence identity, about 80% or 85% sequence identity, or about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to glyphosate-resistant nucleic acid molecules of the invention. BLAST protein searches can be performed with the BLASTX program, score=50, wordlength=3, to obtain amino acid sequences homologous to herbicide resistance protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) supra, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the herbicide resistance-encoding nucleotide sequences include those sequences that encode an herbicide resistance protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the herbicide resistance proteins disclosed in the present invention as discussed below. Variant proteins encompassed by the present invention are biologically active, that is they retain the desired biological activity of the native protein, that is, herbicide resistance activity. By "retains herbicide resistance activity" is intended that the variant will have at least about 30%, at least about 50%, at least about 70%, or at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded herbicide resistance protein, without altering the biological activity of the protein. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

Figure 1B:
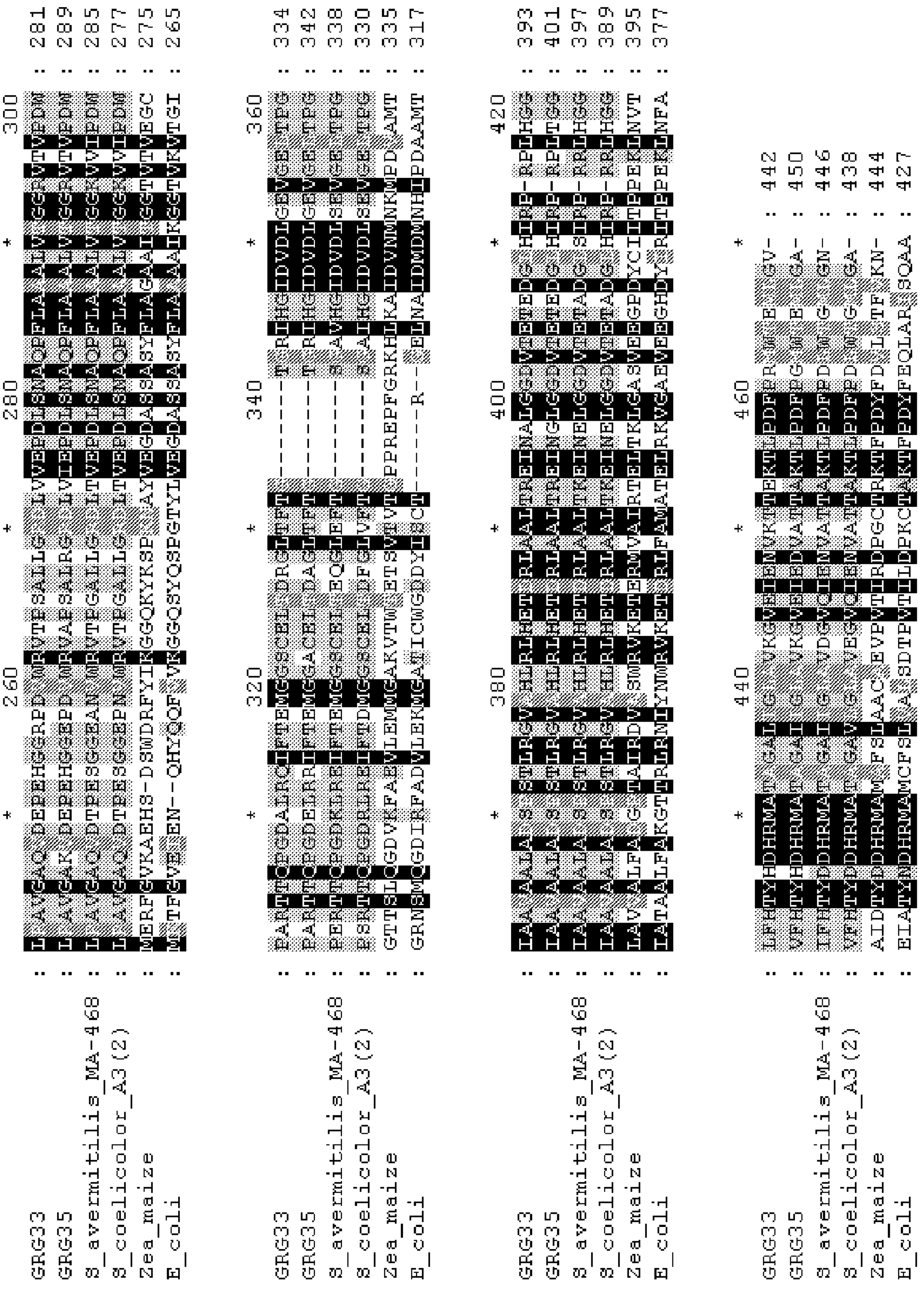
Figure 2A:
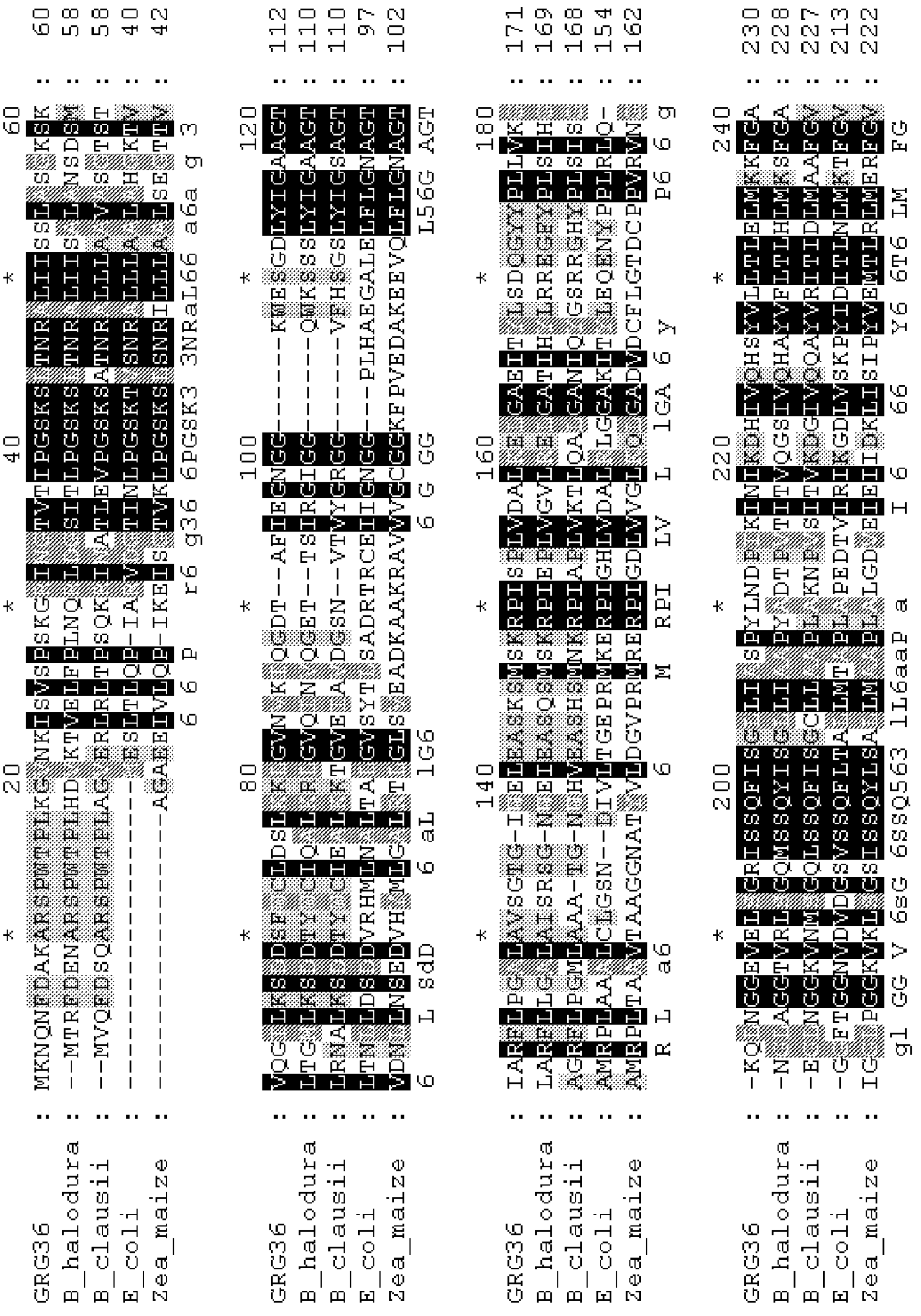
FIG. 2 shows an alignment of the amino acid sequence of GRG36 (SEQ ID NO:8) with EPSP synthase sequences from *Bacillus halodurans* (SEQ ID NO:26), *Bacillus claussi* (SEQ ID NO:27), *Zea mays* (SEQ ID NO:38), and *E. coli* (SEQ ID NO:37). The alignment shows the most highly conserved amino acid residues highlighted in black and highly conserved amino acid residues highlighted in gray.
Figure 2B:
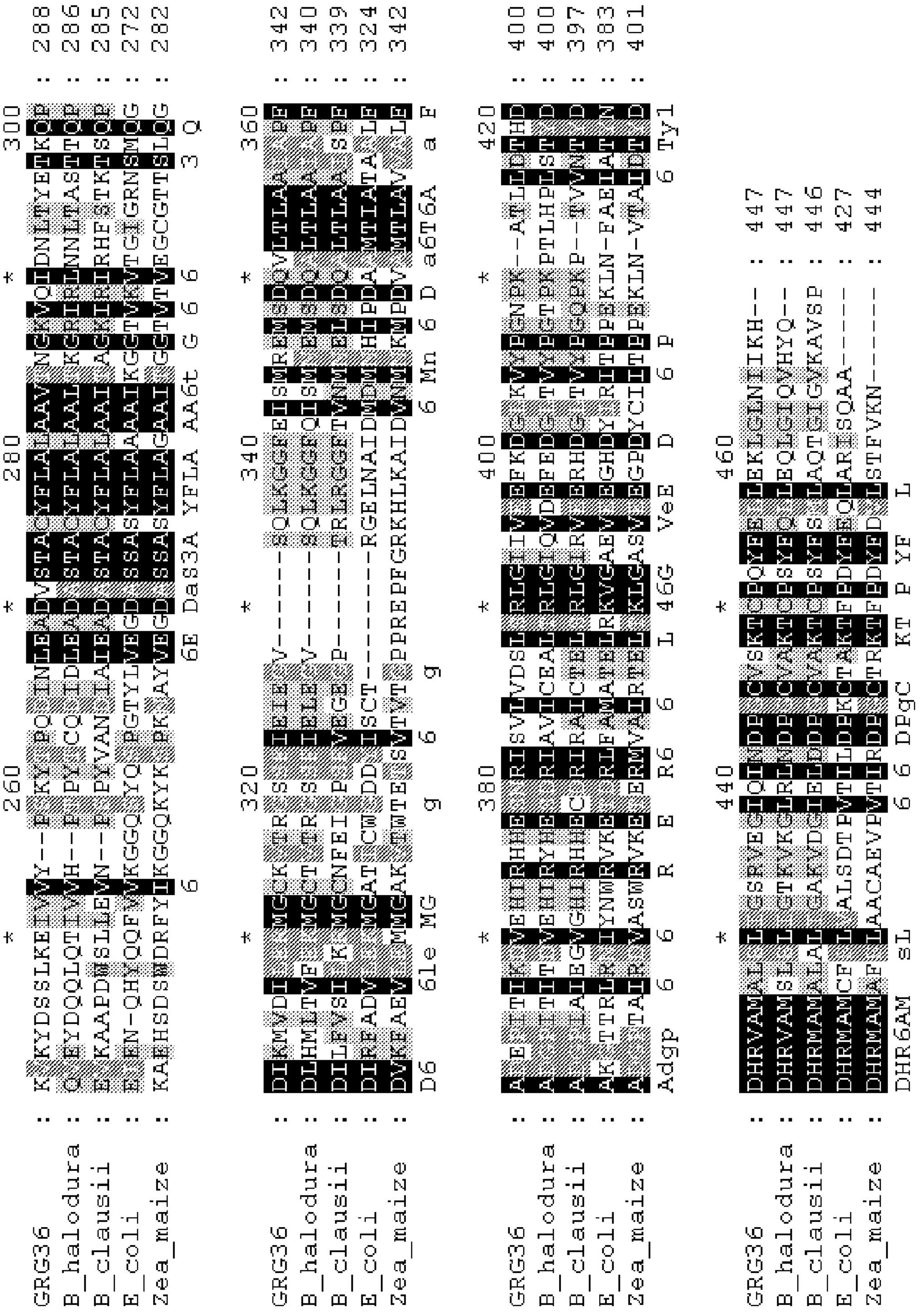
Figure 3A:
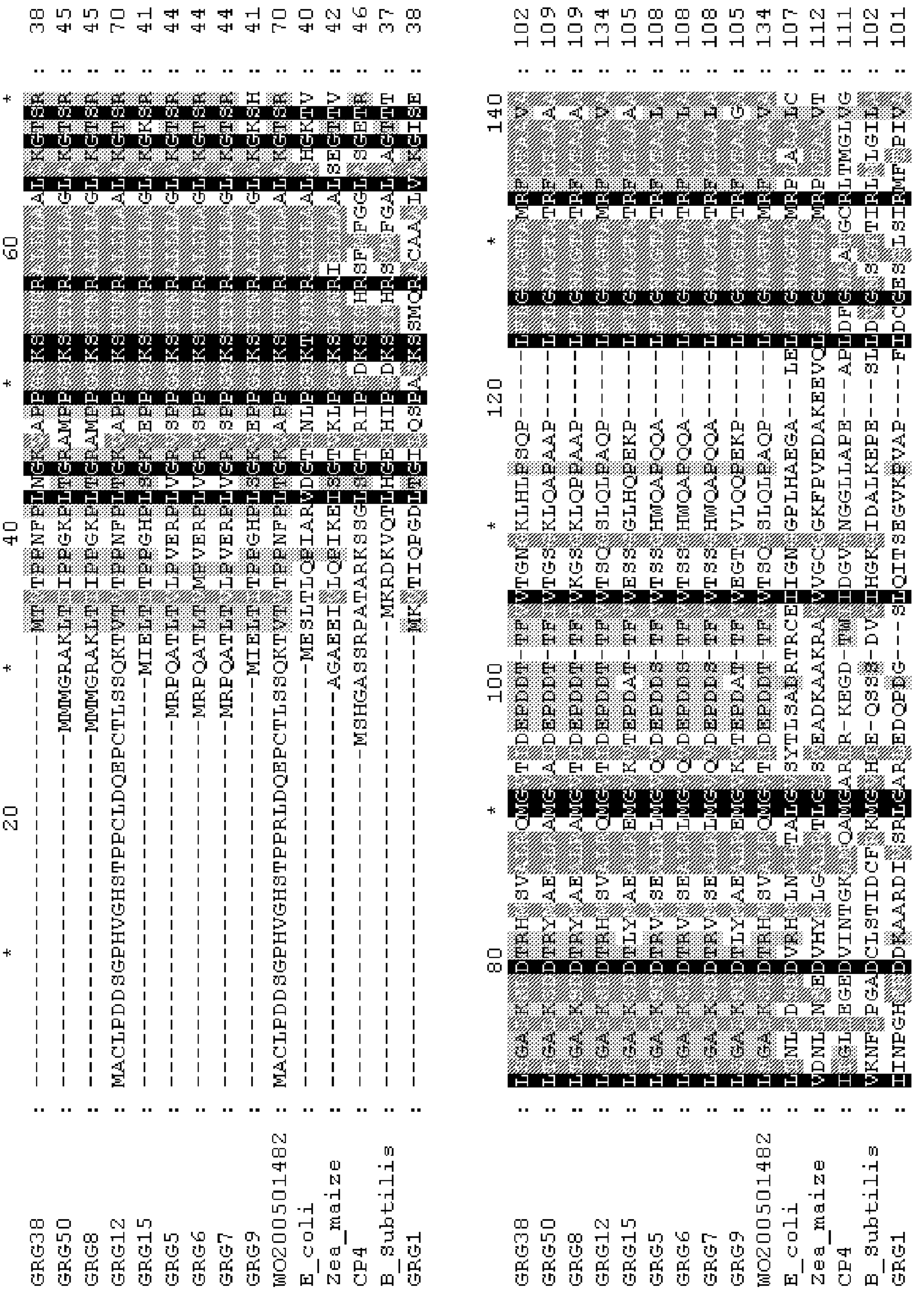
FIG. 3 shows an alignment of GRG38 (SEQ ID NO:16) and GRG50 (SEQ ID NO:22) with other EPSP synthase enzymes, including GRG8 (SEQ ID NO:29), GRG12 (SEQ ID NO:30), GRG15 (SEQ ID NO:31), GRG5 (SEQ ID NO:32), GRG6 (SEQ ID NO:33), GRG7 (SEQ ID NO:34), GRG9 (SEQ ID NO:35), GRG1 (SEQ ID NO:41), the EPSP synthase described in International Patent Application No. WO2005014820 (SEQ ID NO:36), and EPSP synthase enzymes from *E. coli* (SEQ ID NO:37), *Zea mays* (SEQ ID NO:38), *Agrobacterium tumefaciens* (SEQ ID NO:39), and *Bacillus subtilis* (SEQ ID NO:40). The alignment shows the most highly conserved amino acid residues highlighted in black, and highly conserved amino acid residues highlighted in gray.
Figure 3B:
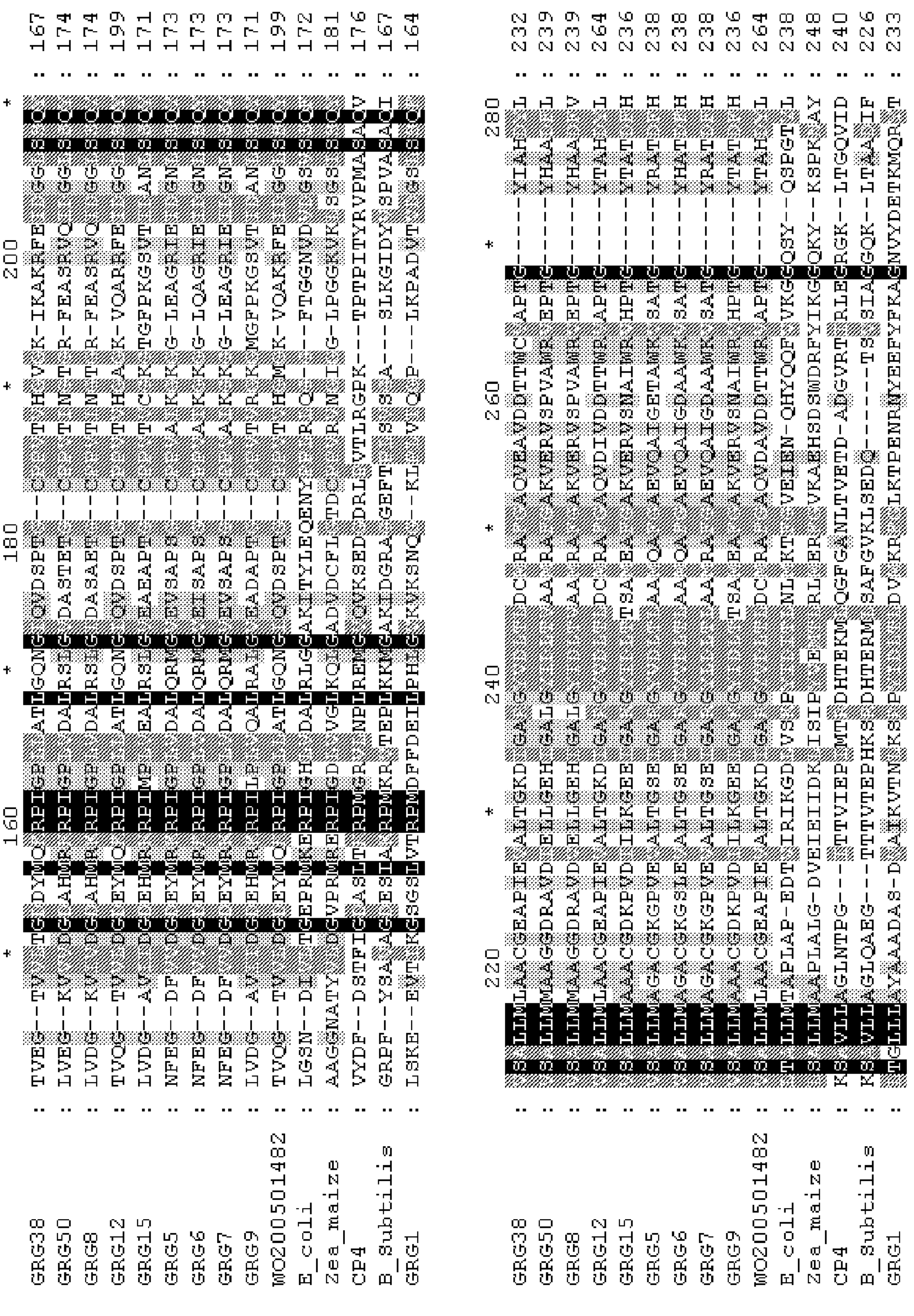
Figure 3C:
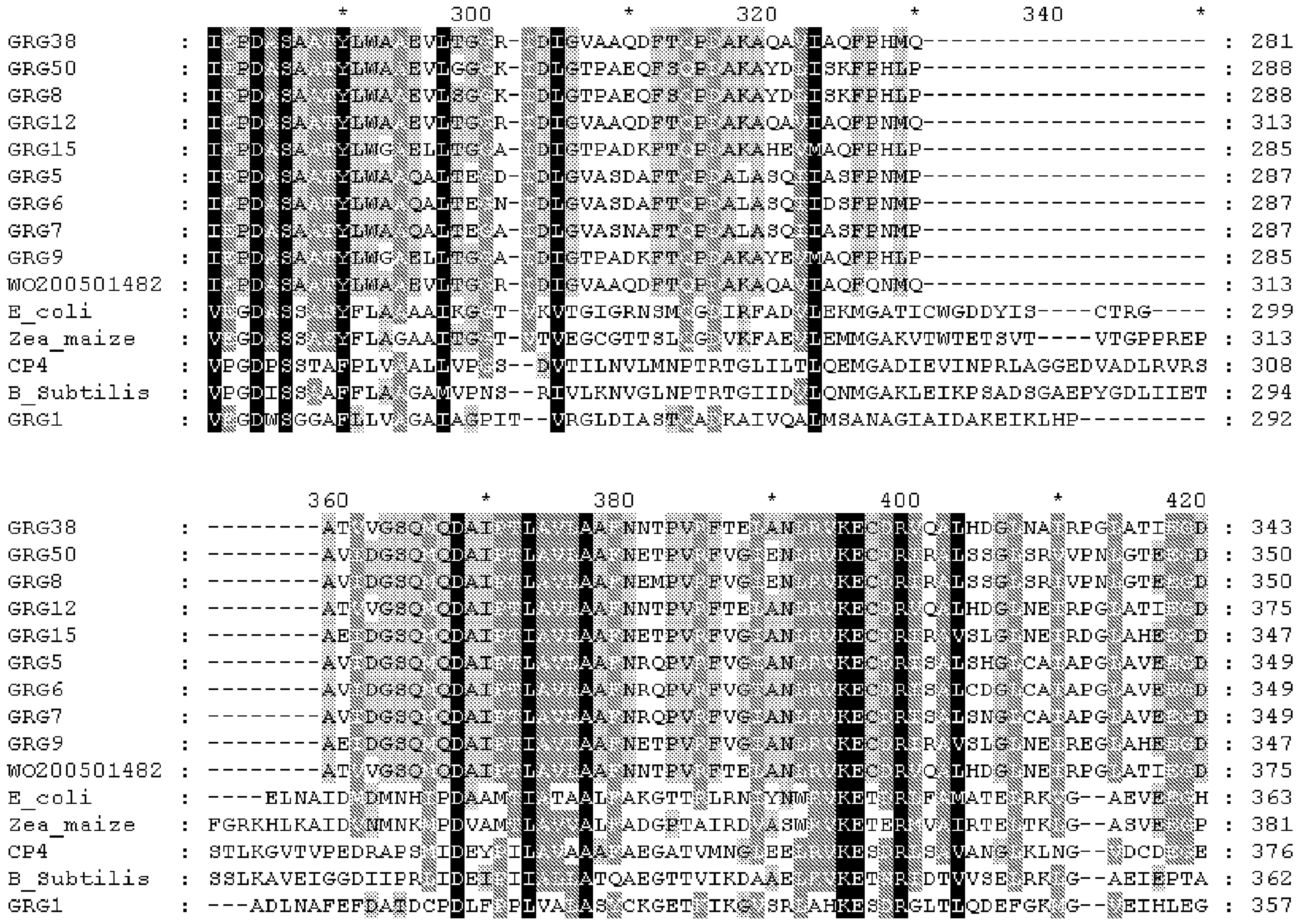
Figure 3D:
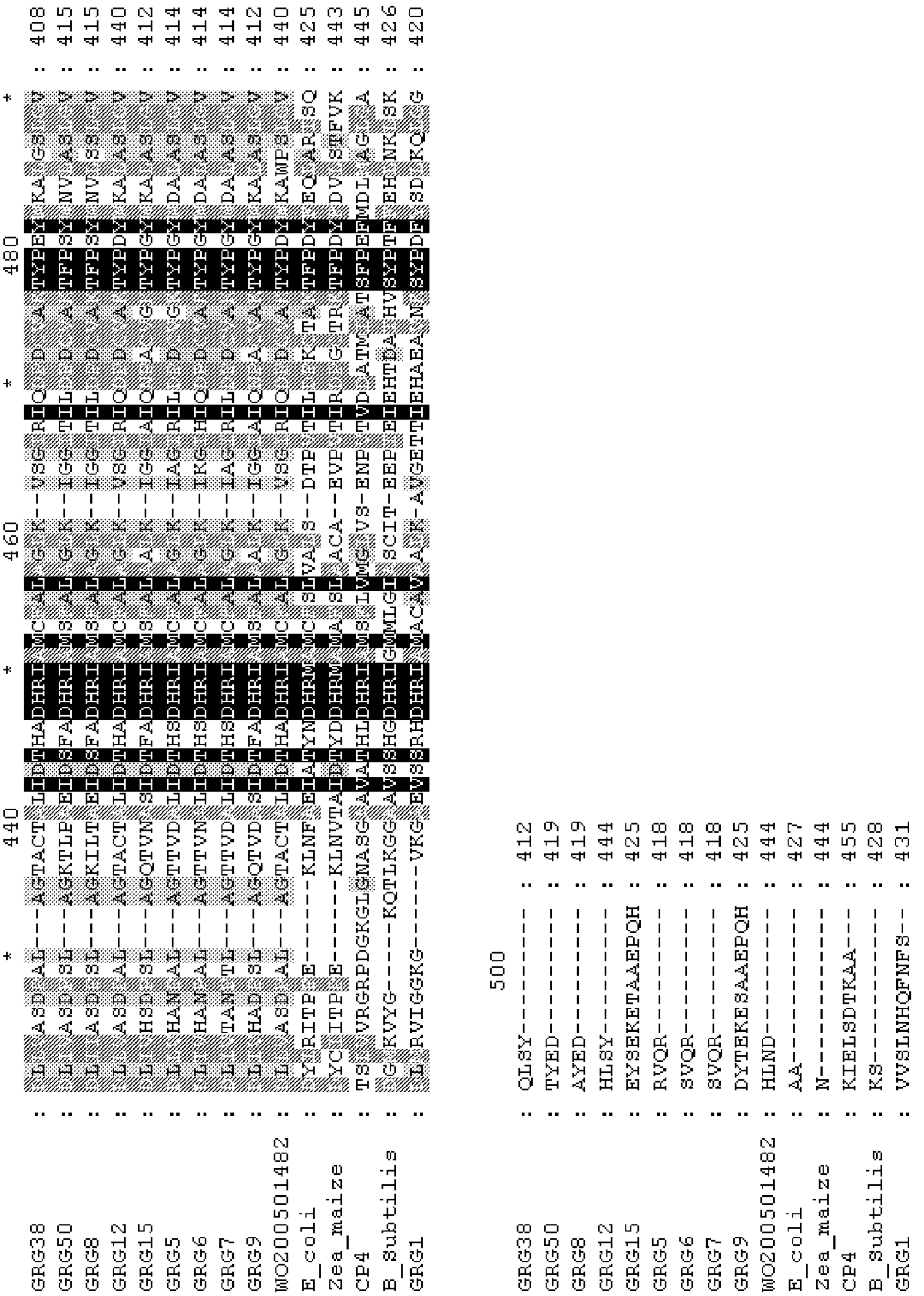

For example, conservative amino acid substitutions may be made at one or more predicted, preferably nonessential amino acid residues. A "nonessential" amino acid residue is a residue that can be altered from the wild-type sequence of an herbicide resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues. Examples of residues that are conserved and that may be essential for protein activity include, for example, residues that are identical between all proteins contained in the alignment of FIGS. 1, 2, or 3. Examples of residues that are conserved but that may allow conservative amino acid substitutions and still retain activity include, for example, residues that have only conservative substitutions between all proteins contained in the alignment of FIGS. 1, 2, or 3.

Lys-22, Arg-124, Asp-313, Arg-344, Arg-386, and Lys-411, are conserved residues of the EPSP synthase from *E. coli* (Schonbrunn et al. (2001) *Proc. Natl. Acad. Sci. USA* 98: 1376-1380). Conserved residues important for EPSP synthase activity also include Arg-100, Asp-242, and Asp-384 (Selvapandiyan et al. (1995) *FEBS Letters* 374:253-256). Arg-27 binds to S3P (Shuttleworth et al. (1999) *Biochemistry* 38:296-302).

Alternatively, variant nucleotide sequences can be made by introducing mutations randomly along all or part of the coding sequence, such as by saturation mutagenesis, and the resultant mutants can be screened for ability to confer herbicide resistance activity to identify mutants that retain activity. Following mutagenesis, the encoded protein can be expressed recombinantly, and the activity of the protein can be determined using standard assay techniques.

Using methods such as PCR, hybridization, and the like, corresponding herbicide resistance sequences can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the herbicide resistance nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequences disclosed herein. Degenerate primers designed on the basis of conserved nucleotides or amino acid residues in the nucleotide sequences or encoded amino acid sequences can additionally be used. The probe typically comprises a region of nucleotide sequence that hybridizes under stringent conditions to at least about 12, preferably about 25, at least about 50, 75, 100, 125, 150, 175, 200, 250, 300, 350, 400, 500, 600, 700, 800, 900, 1000, 1200, 1300 consecutive nucleotides of an herbicide resistance-encoding nucleotide sequence of the invention or a fragment or variant thereof. Methods for the preparation of probes for hybridization are generally known in the art and are disclosed in Sambrook and Russell, 2001, supra and Sambrook et al. (1989) *Molecular Cloning: A Laboratory Manual* (2d ed., Cold Spring Harbor Laboratory Press, Cold Spring Harbor, N.Y.), both of which are herein incorporated by reference.

For example, an entire herbicide resistance sequence disclosed herein, or one or more portions thereof, may be used as a probe capable of specifically hybridizing to corresponding herbicide resistance sequences and messenger RNAs. To achieve specific hybridization under a variety of conditions, such probes include sequences that are unique and are at least about 10 nucleotides in length, or at least about 20 nucleotides in length. Such probes may be used to amplify corresponding herbicide resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. Unless otherwise specified, hybridization conditions are under high stringency.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Herbicide resistance proteins are also encompassed within the present invention. By "herbicide resistance protein" is intended a protein having the amino acid sequence set forth in SEQ ID NO:2, 5, 8, 11, 14, 16, 19, or 22. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein as set forth SEQ ID NO:2, 5, 8, 11, 14, 16, 19, or 22, and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity. Methods for measuring herbicide resistance activity are well known in the art. See, for example, U.S. Pat. Nos. 4,535,060, and 5,188,642, each of which are herein incorporated by reference in their entirety. As used here, a fragment comprises at least 8 contiguous amino acids of SEQ ID NO:2, 5, 8, 11, 14, 16, 19, or 22. The invention encompasses other fragments, however, such as any fragment in the protein greater than about 10, 20, 30, 50, 100, 150, 200, 250, 300, 350, or 400 amino acids.

By "variants" is intended proteins or polypeptides having an amino acid sequence that is at least about 60%, 65%, about 70%, 75%, 80%, 85%, or 90%, 91%, 92%, 93%, 94%, 95%, 96%, 97%, 98% or 99% identical to the amino acid sequence of SEQ ID NO:2, 5, 8, 11, 14, 16, 19, or 22. Variants also include polypeptides encoded by a nucleic acid molecule that hybridizes to the nucleic acid molecule of SEQ ID NO:1, 3, 4, 6, 7, 9, 10, 12, 13, 15, 17, 18, 20, 21, or 23, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining herbicide resistance activity. Methods for measuring herbicide resistance activity are well known in the art. See, for example, U.S. Pat. Nos. 4,535,060, and 5,188,642, each of which are herein incorporated by reference in their entirety.

Bacterial genes, such as the grg and syngrg genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants of grg and syngrg that confer herbicide resistance. These herbicide resistance proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that the DNA sequences of the grg or syngrg genes of the invention may be altered by various methods, and that these alterations may result in DNA sequences encoding proteins with amino acid sequences different than that encoded by the grg or syngrg sequences disclosed herein. This protein may be altered in various ways including amino acid substitutions, deletions, truncations, and insertions of one or more amino acids of SEQ ID NO:1, 3, 4, 6, 7, 9, 10, 12, 13, 15, 17, 18, 20, 21, or 23, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100 or more amino acid substitutions, deletions or insertions.

Methods for such manipulations are generally known in the art. For example, amino acid sequence variants of the GRG proteins disclosed herein can be prepared by mutations in the DNA. This may also be accomplished by one of several forms of mutagenesis and/or in directed evolution. In some aspects, the changes encoded in the amino acid sequence will not substantially affect function of the protein. Such variants will possess the desired herbicide resistance activity. However, it is understood that the ability of the GRG proteins disclosed herein to confer herbicide resistance may be improved by one use of such techniques upon the compositions of this invention. For example, one may express the grg or syngrg sequences disclosed herein in host cells that exhibit high rates of base misincorporation during DNA replication, such as XL-1 Red (Stratagene, La Jolla, Calif.). After propagation in such strains, one can isolate the DNA of the invention (for example by preparing plasmid DNA, or by amplifying by PCR and cloning the resulting PCR fragment into a vector), culture the grg mutations in a non-mutagenic strain, and identify mutated genes with improved resistance to an herbicide such as glyphosate, for example by growing cells in increasing concentrations of glyphosate and testing for clones that confer ability to tolerate increased concentrations of glyphosate.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, or, (3) target secretion or translation of a protein to a subcellular organelle, such as the periplasmic space of gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different herbicide resistance protein coding regions can be used to create a new herbicide resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the herbicide resistance gene of the invention and other known herbicide resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Transformation of Bacterial or Plant Cells

Provided herein are novel isolated genes that confer resistance to an herbicide. Also provided are amino acid sequences of the GRG proteins of the invention. The protein resulting from translation of this gene allows cells to function in the presence of concentrations of an herbicide that are otherwise toxic to cells including plant cells and bacterial cells. In one aspect of the invention, the grg or syngrg genes are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art.

By engineering the genes of the invention to be expressed from a promoter known to stimulate transcription in the organism to be tested and properly translated to generate an intact GRG peptide, and placing the cells in an otherwise toxic concentration of herbicide, one can identify cells that have been transformed with the DNA by virtue of their resistance to herbicide. By "promoter" is intended a nucleic acid sequence that functions to direct transcription of a downstream coding sequence. The promoter, together with other transcriptional and translational regulatory nucleic acid sequences, (also termed as "control sequences") are necessary for the expression of a DNA sequence of interest.

Transformation of bacterial cells is accomplished by one of several techniques known in the art, including but not limited to electroporation or chemical transformation (see, for example, Ausubel, ed. (1994) *Current Protocols in Molecular Biology*, John Wiley and Sons, Inc., Indianapolis, Ind.). Markers conferring resistance to toxic substances are useful in identifying transformed cells (having taken up and expressed the test DNA) from non-transformed cells (those not containing or not expressing the test DNA). In one aspect of the invention, the grg or syngrg genes disclosed herein are useful as markers to assess transformation of bacterial or plant cells.

Transformation of plant cells can be accomplished in similar fashion. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The grg genes of the invention may be modified to obtain or enhance expression in plant cells. The herbicide resistance sequences of the invention may be provided in expression cassettes for expression in the plant of interest. "Plant expression cassette" includes DNA constructs, including recombinant DNA constructs, that are capable of resulting in the expression of a protein from an open reading frame in a plant cell. The cassette will include in the 5'-3' direction of transcription, a transcriptional initiation region (i.e., promoter, particularly a heterologous promoter) operably-linked to a DNA sequence of the invention, and/or a transcriptional and translational termination region (i.e., termination region) functional in plants. The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the herbicide resistance sequence to be under the transcriptional regulation of the regulatory regions.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Often, such constructs will also contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the herbicide resistance sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can then be used to confirm the presence of the integrated heterologous gene of interest in the genome of transgenic plant.

Generation of transgenic plants may be performed by one of several methods, including but not limited to introduction of heterologous DNA by *Agrobacterium* into plant cells (Agrobacterium-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*, Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragments to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by the genes disclosed herein is then tested by hybridizing the filter to a radioactive probe derived from a polynucleotide of the invention, by methods known in the art (Sambrook and Russell, 2001, supra)

Western blot and biochemical assays and the like may be carried out on the transgenic plants to determine the presence of protein encoded by the herbicide resistance gene by standard procedures (Sambrook and Russell, 2001, supra) using antibodies that bind to one or more epitopes present on the herbicide resistance protein.

Methods for Increasing Plant Yield

Methods for increasing plant yield are provided. The methods comprise introducing into a plant or plant cell a polynucleotide comprising a grg sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant is treated with an effective concentration of an herbicide, where the herbicide application results in enhanced plant yield. By "effective concentration" is intended the concentration which allows the increased yield in the plant. Such effective concentrations for herbicides of interest are generally known in the art. The herbicide may be applied either pre- or post emergence in accordance with usual techniques for herbicide application to fields comprising crops which have been rendered resistant to the herbicide by heterologous expression of a grg gene of the invention.

Methods for conferring herbicide resistance in a plant or plant part are also provided. In such methods, a grg polynucleotide disclosed herein is introduced into the plant, wherein expression of the polynucleotide results in glyphosate tolerance or resistance. Plants produced via this method can be treated with an effective concentration of an herbicide and display an increased tolerance to the herbicide. An "effective concentration" of an herbicide in this application is an amount sufficient to slow or stop the growth of plants or plant parts that are not naturally resistant or rendered resistant to the herbicide.

In another embodiment, methods for conferring herbicide resistance in a plant or plant part are provided, wherein the plant or plant part is grown under higher or lower than ambient environmental temperatures as described supra. Glyphosate tolerant EPSP synthase enzymes having thermal stability at higher or lower temperatures, or have temperature optima at higher or lower temperatures, are useful for conferring glyphosate tolerance in plants that are grown under such conditions.

Methods of Controlling Weeds in a Field

Methods for selectively controlling weeds in a field containing a plant are also provided. In one embodiment, the plant seeds or plants are glyphosate resistant as a result of a grg polynucleotide disclosed herein being inserted into the plant seed or plant. In specific methods, the plant is treated with an effective concentration of an herbicide, where the herbicide application results in a selective control of weeds or other untransformed plants. By "effective concentration" is intended the concentration which controls the growth or spread of weeds or other untransformed plants without significantly affecting the glyphosate-resistant plant or plant seed. Such effective concentrations for herbicides of interest are generally known in the art. The herbicide may be applied either pre- or post emergence in accordance with usual techniques for herbicide application to fields comprising plants or plant seeds which have been rendered resistant to the herbicide.

The following examples are offered by way of illustration and not by way of limitation.

EXPERIMENTAL

Example 1

Isolation of Glyphosate Resistant EPSP Synthases

Strains capable of growth in presence of glyphosate were isolated by plating samples of soil on HEPES Mineral Salts Medium (HMSM) containing glyphosate as the sole source of phosphorus. Since HMSM contains no aromatic amino acids, a strain must be resistant to glyphosate in order to grow on this media.

Two grams of soil were suspended in approximately 10 ml of water, vortexed for 15 seconds and permitted to settle for 15 minutes. A 100 µl loopful of this suspension was added to 3 ml of HMSM supplemented with 10 mM glyphosate (pH 7.0). HMSM contains (per liter): 10 g glucose, 2 g $NH_4SO_4$, 9.53 g HEPES, 1.0 ml 0.8 M $MgSO_4$, 1.0 ml 0.1 M $CaCl_2$, 1.0 ml Trace Elements Solution (In 100 ml of 1000× solution: 0.1 g $FeSO_4.7H_2O$, 0.5 mg $CuSO_4.5H_2O$, 1.0 mg $H_3BO_3$, 1.0 mg $MnSO_4.5H_2O$, 7.0 mg $ZnSO_4.7H_2O$, 1.0 mg $MoO_3$, 4.0 g KCl). The culture was grown in a shaker incubator for four days at 28° C. and then 20 µl was used to inoculate 2.5 ml of fresh HMSM containing 10 mM glyphosate as the only phosphorus source. After two days, 20 µl was used to inoculate another fresh 2.5 ml culture. After 5 days, 20 µl was used to inoculate a fresh 2.5 ml culture. After sufficient growth, the culture was plated onto solid media by streaking a 1 µl loop onto the surface of agar plate containing HMSM agar containing 100 mM glyphosate as the sole phosphorus source and stored at 28° C. The culture was then replated for isolation. The strains listed in Table 1 were among the strains selected due to their ability to grow in the presence of high glyphosate concentrations.

TABLE 1

| Strain Name | Strain ID | EPSP synthase Gene Name |
|---|---|---|
| ATX21561 | Unknown | grg33 |
| ATX21563 | Unknown | grg35 |
| ATX21567 | Unknown | grg36 |

Example 2

Isolation of Glyphosate Resistant EPSP Synthases grg37 and grg39

Strains capable of growth in presence of glyphosate were isolated by plating samples of soil on various growth media containing glyphosate. Some strains were isolated on mineral salts media supplemented with glyphosate. Other strains were isolated under rich media in the presence of glyphosate and later tested on mineral salts media supplemented with glyphosate. Since the mineral salts media contain no aromatic amino acids, a strain must be resistant to glyphosate in order to grow on this media.

Strains ATX21800 and ATX21804 were isolated by incubation under rich conditions and supplemention with glyphosate. These strains were then tested for their ability to grow in the presence of glyphosate without aromatic amino acids. Strain ATX21804 was isolated from soil (0.01 grams) that was air dried for two days and plated onto nutrient broth agar supplemented with 100 mM glyphosate. A small amount (10 µl) was then used to inoculate an eosin methylene blue agar plate containing 300 mM glyphosate. ATX21800 was isolated by incubating 0.01 grams soil with 3 ml nutrient broth supplemented with 100 mM glyphosate. After initial isolation, each strain was inoculated into Luria Bertani agar plates to confirm single colony type. These strains were then tested on Brunner minimal medium containing 100 mM glyphosate and were confirmed to grow in the presence of glyphosate without aromatic amino acids.

The strains listed in Table 2 were among the strains selected due to their ability to grow in the presence of high glyphosate concentrations.

TABLE 2

| Strain Name | Strain ID | EPSP synthase Gene Name |
|---|---|---|
| ATX21800 | Unknown | grg37 |
| ATX21804 | Unknown | grg39 |

Example 3

Isolation of Glyphosate Resistant EPSP Synthases grg38 and grg50

Strains capable of growth in presence of glyphosate were isolated by plating samples of soil on various growth media containing glyphosate. Some strains were isolated on mineral salts media supplemented with glyphosate. Other strains were isolated under rich media in the presence of glyphosate and later tested on mineral salts media supplemented with glyphosate. Since the mineral salts media contain no aromatic amino acids, a strain must be resistant to glyphosate in order to grow on this media.

Strain ATX20103 was isolated by suspending approximately 2 grams of soil in 10 ml of water, vortexing for 15 seconds and permitting to settle for 15 minutes. A 10 μl loopful of this suspension was added to 3 ml of Tris MSM (TMSM) supplemented with 10 mM glyphosate (pH 7.0). TMSM contains (per liter): 10 g glucose, 2 g $NH_4SO_4$, 12.12 g Tris, 1.0 ml 0.8 M $MgSO_4$, 1.0 ml 0.1 M $CaCl_2$, 1.0 ml Trace Elements Solution (In 100 ml of 1000× solution: 0.1 g $FeSO_4.7H_2O$, 0.5 mg $CuSO_4.5H_2O$, 1.0 mg 1.0 mg $MnSO_4.5H_2O$, 7.0 mg $ZnSO_4.7H_2O$, 1.0 mg $MoO_3$, 4.0 g KCl). The culture was then incubated at 28° C. for isolation over repeated rounds of selection and then inoculated onto Luria Bertani agar to confirm single colony type. ATX20103 was then reconfirmed to grow on TMSM in the presence of glyphosate without aromatic acids.

Strain ATX21806 was isolated by incubating under rich conditions and supplementing with glyphosate. This strain was then tested for its ability to growth in the presence of glyphosate without aromatic amino acids. Strain ATX21806 was isolated from soil (0.01 grams) that had been suspended in 10 ml water overnight. A small amount (10 μl) was then used to inoculate an eosin methylene blue agar plate containing 300 mM glyphosate. After each initial isolation, the strain was inoculated into Luria Bertani agar plates to confirm single colony type. The strain was then tested on Brunner minimal medium at 100 mM glyphosate and was confirmed to grow in the presence of glyphosate without aromatic amino acids.

The strains listed in Table 3 were among the strains selected due to their ability to grow in the presence of high glyphosate concentrations.

TABLE 3

| Strain Name | Strain ID | EPSP synthase Gene Name |
|---|---|---|
| ATX21806 | Unknown | grg38 |
| ATX20103 | *Rhizobium leguminosarum* | grg50 |

Example 4

Cloning of Glyphosate-Resistant EPSP Synthases

Genomic DNA was extracted from the strains described in Tables 1, 2, and 3, and the resulting DNA was partially digested with restriction enzyme Sau3A 1 to yield DNA fragments approximately 5 kilobases in size. These DNA molecules were size selected on agarose gels, purified, and ligated into LAMBDA ZAP® vector arms pre-digested with BamHI. The ligated arms were then packaged into phage particles, and phage titers determined as known in the art. The resulting libraries were amplified by methods known in the art to generate a library titer of between $3\times10^7$ and $3\times10^8$ PFU/mL. For each independent library, *E. coli* (XL1 Blue MRF') was then co-transfected with phage from an amplified library as well as M13 helper phage to allow mass excision of the library in the form of an infectious, circular ssDNA as known in the art (Short et al. (1988) *Nucleic Acids Research* 16:7583-7600). After centrifugation of the co-infected cells, the phage-containing supernatant was heated to 65-70° C. for 15-20 minutes to incapacitate any residual lambda phage particles. Dilutions of the resulting ssDNA plasmid library were transfected into a fresh culture of competent *E. coli* XL-Blue MRF'(aroA) cells (XL1 Blue MRF'). The resulting transfected cells were plated onto M63 plates containing kanamycin, 0.1 mM IPTG and either 0 mM, 20 mM or 50 mM glyphosate.

The *E. coli* XL-Blue MRF'(aroA) used for the transfection expresses the F-pilus, and also contains a deletion of the aroA gene encoding the endogenous *E. coli* EPSP synthase enzyme. This strain is also referred to as herein as ΔaroA. This ΔaroA strain is unable to grow on minimal media lacking aromatic amino acids, unless complemented by a functional EPSP synthase. Since glyphosate is a potent inhibitor of typical, glyphosate-sensitive EPSP synthases, such as type I EPSP synthases, transfected clones expressing a non-glyphosate resistant EPSP synthase would be able to grown on M63 plates lacking glyphosate, but would be unable to grow on M63 containing either 20 mM or 50 mM glyphosate. In order to grow on M63 plates containing 20 mM or 50 mM glyphosate, the cells must contain a plasmid that expresses an EPSP synthase that is both (1) capable of complementing the ΔaroA mutation of these cells, and (2) resistant to glyphosate. Thus, this screening method allows identification of clones containing glyphosate-resistant EPSP synthases.

Colonies growing on 20 mM or 50 mM glyphosate were picked and their plasmids analyzed by restriction digest to identify plasmids with shared restriction patterns. Individual plasmids were sequenced by methods known in the art.

Using this approach, as sometimes modified for each library as known and appreciated in the art, library clones containing EPSP synthase genes were identified for each of the strains listed in Table 4.

Example 5

DNA and Protein Sequences of EPSP Synthases

The DNA sequences of the glyphosate-resistant EPSP synthases was determined for each of the clones described above by methods well known in the art.

grg33. The DNA sequence of grg33 is provided herein as SEQ ID NO:1. The predicted translation product of grg33 (GRG33) is provided herein as SEQ ID NO:2. A synthetic sequence encoding GRG33 (syngrg33) was also designed and is provided herein as SEQ ID NO:3.

grg35. The DNA sequence of grg35 is provided herein as SEQ ID NO:4. The predicted translation product of grg35 (GRG35) is provided herein as SEQ ID NO:5. A synthetic sequence encoding GRG35 (syngrg35) was also designed and is provided herein as SEQ ID NO:6.

grg36. The DNA sequence of grg36 is provided herein as SEQ ID NO:7. The predicted translation product of grg36 (GRG36) is provided herein as SEQ ID NO:8. A synthetic sequence encoding GRG36 (syngrg36) was also designed and is provided herein as SEQ ID NO:9.

grg37. The DNA sequence of grg37 is provided herein as SEQ ID NO:10. The predicted translation product of grg37

(GRG37) is provided herein as SEQ ID NO:11. A synthetic sequence encoding GRG37 (syngrg37) was also designed and is provided herein as SEQ ID NO:12.

grg38. The DNA sequence of grg38 is provided herein as SEQ ID NO:15. The predicted translation product of grg38 (GRG38) is provided herein as SEQ ID NO:16. A synthetic sequence encoding GRG38 (syngrg38) was also designed and is provided herein as SEQ ID NO:17.

grg39. The DNA sequence of grg39 is provided herein as SEQ ID NO:18. The predicted translation product of grg39 (GRG39) is provided herein as SEQ ID NO:19. A synthetic sequence encoding GRG39 (syngrg39) was also designed and is provided herein as SEQ ID NO:20.

grg50. The DNA sequence of grg50 is provided herein as SEQ ID NO:21. The predicted translation product of grg50 (GRG50) is provided herein as SEQ ID NO:22. A synthetic sequence encoding GRG50 (syngrg50) was also designed and is provided herein as SEQ ID NO:23.

Clones containing each of the grg33, grg35, grg36, grg37, grg38, grg39, and grg50 EPSP synthase genes were deposited at NRRL on Jun. 9, 2006 or Jun. 26, 2007 and assigned deposit numbers as in Table 4.

TABLE 4

Clones containing glyphosate-resistant EPSP synthases

| EPSPS | Strain yielding EPSPS | Original Isolate in pBKCMV | NRRL Number |
|---|---|---|---|
| GRG33 | ATX21561 | pAX1947 | B-30932 |
| GRG35 | ATX21563 | pAX1948 | B-30933 |
| GRG36 | ATX21567 | pAX1949 | B-30934 |
| GRG37 | ATX21800 | pAX1963 | B-30945 |
| GRG38 | ATX21806 | pAX1964 | B-30946 |
| GRG39 | ATX21804 | pAX1965 | B-30947 |
| GRG50 | ATX20103 | pAX1966 | B-30948 |

Each of the proteins GRG33, GRG35, and GRG36 showed regions of homology to EPSP synthase enzymes in the NCBI database by BLAST search. The EPSPS enzyme with the highest protein sequence identity to each GRG enzyme is listed in Table 5.

TABLE 5

Homology of GRG33-GRG36 to known EPSP synthases

| Protein | Strain with homologous EPSPS enzyme | % Identity |
|---|---|---|
| GRG33 | GRG35, *S. coelicolor* | 88%, 86% |
| GRG35 | GRG33, *S. coelicolor* | 88%, 85% |
| GRG36 | *Bacillus halodurans* | 53% |

The amino acid sequences of GRG33 and GRG35 are 88% identical. A search of public protein databases with the amino acid sequence of GRG33 shows that this protein is 86% identical over 430 amino acids to the EPSP synthase from *Streptomyces coelicolor* (SEQ ID NO:24 GENBANK® Accession No. NP 629359.1), and 82% identical over 430 amino acids to the EPSP synthase from *Streptomyces avermitilis* (SEQ ID NO:25; GENBANK® Accession No. NP824218.1).

The amino acid sequence of GRG35 similarly is 85% identical over 434 amino acids to the EPSP synthase from *Streptomyces coelicolor* (SEQ ID NO:24; GENBANK® Accession No. NP 629359.1), and 81% identical over 441 amino acids to the EPSP synthase from *Streptomyces avermitilis* (SEQ ID NO:25; GENBANK® Accession No. NP 824218.1).

TABLE 6

Amino acid identity of GRG33 and GRG35 with Streptomyces EPSP synthases

| EPSP synthase | Identity with GRG33 | Identity with GRG35 |
|---|---|---|
| GRG33 | — | 88% |
| GRG35 | 88% | — |
| *Streptomyces coelicolor* A3(2) | 84% | 82% |
| *Streptomyces avermitilis* MA-4680 | 80% | 78% |
| *E. coli* | 30% | 29% |
| Maize | 30% | 29% |

A search of public protein databases with the amino acid sequence of GRG36 shows that this protein is related to the EPSP synthase from *Bacillus halodurans*, (64% identical over 441 amino acids, SEQ ID NO:26; GENBANK® Accession No. BAB06432.1), and to a lesser extent to the EPSP synthase from *Bacillus clausii* (55% identical over 439 amino acids; SEQ ID NO:27; GENBANK® Accession No. BAD63759.1)

TABLE 7

Amino acid identity of GRG36 with EPSP synthases

| EPSP synthase | Identity with GRG36 |
|---|---|
| *Bacillus halodurans* | 62% |
| *Bacillus clausii* | 54% |
| *E. coli* | 31% |
| Maize | 34% |

A search of public protein databases with the amino acid sequence of GRG37 shows that this protein is 81% identical to the EPSP synthase from *Arthrobacter* sp. FB24 (SEQ ID NO:28, GENBANK® Accession No. ZP_00413033.1)

The grg37 open reading frame has two potential start codons. The upstream ATG (predicted amino acid sequence MTASPMGASADNS . . . (corresponding to amino acid positions 1 through 13 of SEQ ID NO:10)) contains the best ribosome binding site in correct proximity. However, a second downstream ATG may be used. This ORF yields the predicted amino acid sequence MGASADNS . . . (corresponding to amino acid positions 6 through 13 of SEQ ID NO:10)). The upstream ATG appears to have a ribosome binding site ("RBS") that is a better match to the consensus RBS sequence. However, the open reading frame originating from this upstream ATG appears to be translationally coupled to an upstream open reading frame. Translational coupling is one strategy known in the art to be employed by bacteria to ensure good initiation and can substitute for a ribosome binding site. The nucleotide sequence for the downstream start site is provided herein as SEQ ID NO:13, and the encoded amino acid sequence is provided herein as SEQ ID NO:14.

GRG39 shows 96% amino acid identity to the GRG30 EPSP synthase sequence, and is highly homologous to the GRG29 EPSP synthase sequence described in U.S. patent application Ser. No. 11/760,570 filed Jun. 8, 2007.

GRG38 shows 94% amino acid identity to the GRG12 EPSP synthase described in U.S. patent application Ser. No. 11/400,598, filed Apr. 7, 2006 (Table 8). GRG38 also contains the domains of the Class III EPSP synthases described in U.S. patent application Ser. No. 11/400,598.

GRG50 shows 95% amino acid identity to the GRG8 EPSP synthase described in U.S. patent application Ser. No. 11/315,678 filed Dec. 22, 2005 (Table 8). GRG50 also contains the domains of the Class III EPSP synthases described in U.S. application Ser. No. 11/400,598, filed Apr. 7, 2006.

TABLE 8

| Comparison with other Class III EPSP synthases | | |
|---|---|---|
| EPSPS | Amino acid identity with GRG38 | Amino acid identity with GRG50 |
| GRG38 | — | 65% |
| GRG50 | 65% | — |
| GRG8 | 65% | 95% |
| GRG12 | 87% | 62% |
| GRG6 | 67% | 67% |
| GRG9 | 64% | 70% |
| GRG15 | 64% | 71% |
| GRG5 | 68% | 68% |
| GRG37 | 67% | 68% |
| *E. coli* (non-Class III) | 32% | 34% |
| Maize (non-Class III) | 32% | 31% |

Example 6

Cloning of Novel Glyphosate-Resistant EPSP Synthases into an *E. Coli Expression Vector*

The EPSP synthase genes contained in the clones of Table 4 were sub-cloned into the *E. coli* expression vector pRSF1b (Invitrogen). Resulting clones were confirmed by DNA sequencing, and used to induce expression of each EPSP synthase in *E. coli*. The expressed His-tagged protein was then purified as known in the art.

Example 7

Glyphosate Resistance of GRG33 GRG35 and GRG36 EPSP Synthases

The pRSF1b clones were plated onto M63+ plates containing antibiotic and either 0 mM or 50 mM glyphosate. Growth was scored after two days growth at 37° C. Each of the three EPSP synthases was observed to confer resistance to 50 mM glyphosate in *E. coli* cells (Table 9).

TABLE 9

| Glyphosate screen | | |
|---|---|---|
| EPSPS | Clone in pRSF1B | Growth on 50 mM glyphosate |
| Vector | — | — |
| GRG33 | pAX1951 | +++ |
| GRG35 | pAX1952 | +++ |
| GRG36 | pAX1953 | +++ |

Example 8

Glyphosate Resistance of GRG37 and GRG39 EPSP Synthases

Cells containing the plasmid clones shown in Table 4 were plated onto M63+ plates containing antibiotic and either 0 mM or 20 mM glyphosate. Growth was scored after two days growth at 37° C. Each of the EPSP synthases was observed to confer resistance to 20 mM glyphosate in *E. coli* cells (Table 10).

TABLE 10

| Glyphosate screen | | |
|---|---|---|
| EPSPS | Plasmid Clone | Growth on 20 mM glyphosate |
| Vector | — | — |
| GRG37 | pAX1963 | ++ |
| GRG39 | pAX1965 | ++ |

Example 9

Glyphosate Resistance of GRG38 and GRG50 EPSP Synthases

Cells containing the plasmid clones shown in Table 4 were plated onto M63+ plates containing antibiotic and either 0 mM or 20 mM glyphosate. Growth was scored after two days growth at 37° C. Each of the EPSP synthases was observed to confer resistance to 20 mM glyphosate in *E. coli* cells (Table 11).

TABLE 11

| Glyphosate screen | | |
|---|---|---|
| EPSPS | Plasmid Clone | Growth on 20 mM glyphosate |
| Vector | — | — |
| GRG38 | pAX1964 | ++ |
| GRG50 | pAX1966 | ++ |

Example 10

Engineering grg33, grg35, grg36, grg37, grg38, grg39, grg50, syngrg33, syngrg35, syngrg36, syngrg37, syngrg38, syngrg39, and syngrg50 for Plant Transformation The open reading frame (ORF) for each of the grg genes is amplified by PCR from a full-length cDNA template. Hind III restriction sites are added to each end of the orF during PCR. Additionally, the nucleotide sequence ACC is added immediately 5' to the start codon of the gene to increase translational efficiency (Kozak (1987) *Nucleic Acids Research* 15:8125-8148; Joshi (1987) *Nucleic Acids Research* 15:6643-6653). The PCR product is cloned and sequenced, using techniques well known in the art, to ensure that no mutations are introduced during PCR. The plasmid containing the grg PCR product is digested with, for example, Hind III and the fragment containing the intact orF is isolated.

One may generate similar constructs that contain a chloroplast targeting sequence linked to the polynucleotide of the invention by methods known in the art.

A DNA fragment containing the EPSP synthase (and either containing or not containing a chloroplast targeting sequence) is cloned into a plasmid, for example at the Hind III site of pAX200. pAX200 is a plant expression vector containing the rice actin promoter (McElroy et al. (1991) *Molec. Gen. Genet.* 231:150-160), and the PinII terminator (An et al. (1989) *The Plant Cell* 1:115-122). The promoter-gene-terminator fragment (or the promoter-leader-gene-terminator fragment) from this intermediate plasmid is subcloned into a plasmid such as pSB11 (Japan Tobacco, Inc.) to form a final plasmid, referred to herein as, for example, pSB11GRG33.

pSB11GRG33 is organized such that the DNA fragment containing, for example, the promoter-grg36-terminator construct (or the promoter-leader-grg36-terminator construct) may be excised by appropriate restriction enzymes and also used for transformation into plants, for example, by aerosol beam injection. The structure of pSB11GRG33 is verified by restriction digest and gel electrophoresis, as well as by sequencing across the various cloning junctions. The same methods can be used to generate a final plasmid for each of the grg genes described herein.

The plasmid is mobilized into *Agrobacterium tumefaciens* strain LBA4404 which also harbors the plasmid pSB1 (Japan Tobacco, Inc.), using triparental mating procedures well known in the art, and plating on media containing antibiotic. Plasmid pSB11GRG36 carries spectinomycin resistance but is a narrow host range plasmid and cannot replicate in *Agrobacterium*. Antibiotic resistant colonies arise when pSB11GRG36 integrates into the broad host range plasmid pSB1 through homologous recombination. The resulting cointegrate product is verified by Southern hybridization. The *Agrobacterium* strain harboring the cointegrate can be used to transform maize, for example, by the PureIntro method (Japan Tobacco).

Example 11

Transformation grg33, grg35, grg36, grg37, grg38, grg39, grg50, syngrg33, syngrg35, syngrg36, syngrg37, syngrg38, syngrg39, and syngrg50 into Plant Cells Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express the GRG proteins of the present invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

TABLE 12

| DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 12

Transformation of grg33, grg35, grg36, grg37, grg38, grg39, grg50, syngrg33, syngrg35, syngrg36, syngrg37, syngrg38, syngrg39, and syngrg50 into Maize Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated or recombinant nucleic acid molecule comprising a nucleotide sequence selected from the group consisting of:

a) the nucleotide sequence of SEQ ID NO:7 or 9, or a complement thereof;

b) the herbicide resistance nucleotide sequence of the DNA insert of the plasmid deposited as Accession No. NRRL B-30934, or a complement thereof;

c) a nucleotide sequence that encodes a polypeptide comprising the amino acid sequence of SEQ ID NO:8; and d) a nucleotide sequence encoding a polypeptide having at least 95% amino acid sequence identity to the amino acid sequence of SEQ ID NO:8, wherein said polypeptide has herbicide resistance activity.

2. The isolated or recombinant nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. The isolated or recombinant nucleic acid molecule of claim 1, wherein said nucleotide sequence is operably linked to a promoter capable of directing expression of a coding sequence in a plant.

6. A host cell that contains the nucleic acid molecule of claim 5.

7. The host cell of claim 6 that is a bacterial host cell.

8. The host cell of claim 6 that is a plant cell.

9. A transgenic plant comprising the host cell of claim 8.

10. The plant of claim 9, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

11. A transgenic seed comprising the nucleic acid molecule of claim 5.

12. A method for producing a polypeptide with herbicide resistance activity, comprising culturing the host cell of claim 6 under conditions in which a nucleic acid molecule encoding the polypeptide is expressed, said polypeptide being selected from the group consisting of:

a) a polypeptide comprising the amino acid sequence of SEQ ID NO:8;

b) a polypeptide encoded by the nucleotide sequence of SEQ ID NO:7 or 9;

c) a polypeptide comprising an amino acid sequence having at least 95% sequence identity to the amino acid sequence of SEQ ID NO:8, wherein said polypeptide has herbicide resistance activity; and d) a polypeptide that is encoded by the herbicide resistance nucleotide sequence of the DNA insert of the plasmid deposited as Accession No. NRRL B-30934.

13. A method for conferring resistance to an herbicide in a plant, said method comprising transforming said plant with a DNA construct, said construct comprising a promoter that drives expression in a plant cell operably linked with a nucleotide sequence, and regenerating a transformed plant, wherein said nucleotide sequence is selected from the group consisting of:

a) the nucleotide sequence of SEQ ID NO: 7 or 9;

b) the herbicide resistance nucleotide sequence of the DNA insert of the plasmid deposited as Accession No. NRRL B-30934;

c) a nucleotide sequence that encodes a polypeptide comprising the amino acid sequence of SEQ ID NO:8; and d) a nucleotide sequence encoding a polypeptide having at least 95% amino acid sequence identity to the amino acid sequence of SEQ ID NO:8, wherein said polypeptide has herbicide resistance activity.

14. A plant having stably incorporated into its genome a DNA construct comprising a nucleotide sequence that encodes a protein having herbicide resistance activity, wherein said nucleotide sequence is selected from the group consisting of:

a) the nucleotide sequence of SEQ ID NO: 7 or 9;

b) the herbicide resistance nucleotide sequence of the DNA insert of the plasmid deposited as Accession No. NRRL B-30934;

c) a nucleotide sequence that encodes a polypeptide comprising the amino acid sequence of SEQ ID NO:8; and d) a nucleotide sequence encoding a polypeptide having at least 95% amino acid sequence identity to the amino acid sequence of SEQ ID NO:8, wherein said polypeptide has herbicide resistance activity;

wherein said nucleotide sequence is operably linked to a promoter that drives expression of a coding sequence in a plant cell.

15. The plant of claim 14, wherein said plant is a plant cell.

* * * * *

SEQUENCE LISTING

<160> NUMBER OF SEQ ID NOS: 41

<210> SEQ ID NO 1
<211> LENGTH: 1329
<212> TYPE: DNA
<213> ORGANISM: Unknown
<220> FEATURE:
<223> OTHER INFORMATION: Isolated from soil sample
<220> FEATURE:
<221> NAME/KEY: CDS
<222> LOCATION: (1)...(1329)

<400> SEQUENCE: 1 atg acc gac agc aac ccg tcc acc gac ccg ctc acc ggc cgc tgg ccc 48
Met Thr Asp Ser Asn Pro Ser Thr Asp Pro Leu Thr Gly Arg Trp Pro
1 5 10 15 gcc ccg tac gcg gcc ggc gcc gtc gac gcc acc gtc acc gtg ccc gga 96
Ala Pro Tyr Ala Ala Gly Ala Val Asp Ala Thr Val Thr Val Pro Gly
20 25 30 tcg aag tcg gtc acc aac cgc gcc ctg gtg ctc gcc gcg ctg gcc gcc 144
Ser Lys Ser Val Thr Asn Arg Ala Leu Val Leu Ala Ala Leu Ala Ala
35 40 45 gag ccg ggc tgg gtg cgc cgc ccg ctg cgc tcg cgc gac acc ctg ctg 192
Glu Pro Gly Trp Val Arg Arg Pro Leu Arg Ser Arg Asp Thr Leu Leu
50 55 60 atg gcg gag gcg ctg cgc acc ctg ggc gtg aag atc gac gag ggc gtg 240
Met Ala Glu Ala Leu Arg Thr Leu Gly Val Lys Ile Asp Glu Gly Val
65 70 75 80 ggc ccg gac ggc acc ggc gag gcc tgg cgg atc atc ccg gcc ggg ctg 288
Gly Pro Asp Gly Thr Gly Glu Ala Trp Arg Ile Ile Pro Ala Gly Leu
85 90 95 cgc ggc ccg gcg acc gtc gac gtc ggc aac gcg ggc acg gtc atg cgc 336
Arg Gly Pro Ala Thr Val Asp Val Gly Asn Ala Gly Thr Val Met Arg
100 105 110 ttc ctg ccg ccg gtg gcg gcg ctc gcg aac ggc gcg gtg cgc ttc gac 384
Phe Leu Pro Pro Val Ala Ala Leu Ala Asn Gly Ala Val Arg Phe Asp
115 120 125 ggc gac ccg cgc tcc cac gag cgc ccg ctg cac ggg gtg atc gac gcg 432
Gly Asp Pro Arg Ser His Glu Arg Pro Leu His Gly Val Ile Asp Ala
130 135 140 ctg cgc gcg ctg ggc gcc cgg atc gac gac gac ggg cgc ggc gcg ctg 480
Leu Arg Ala Leu Gly Ala Arg Ile Asp Asp Asp Gly Arg Gly Ala Leu
145 150 155 160 ccg atg acc gtg cac ggc gcc ggc ggc ctg gag ggc ggg gtc gtg gag 528
Pro Met Thr Val His Gly Ala Gly Gly Leu Glu Gly Gly Val Val Glu
165 170 175 atc gac gcc tcc tcg tcc tcc cag ttc gtc agc gcg ctg ctg ctc tcc 576
Ile Asp Ala Ser Ser Ser Ser Gln Phe Val Ser Ala Leu Leu Leu Ser
180 185 190 ggc gcc cgc ttc aac cag ggc gtg gag gtg cgg cac gtc ggc acc cgg 624
Gly Ala Arg Phe Asn Gln Gly Val Glu Val Arg His Val Gly Thr Arg
195 200 205 ctg ccc tcg ctg ccg cac atc cgg atg acg gtc gac atg ctg cgc gcg 672
Leu Pro Ser Leu Pro His Ile Arg Met Thr Val Asp Met Leu Arg Ala
210 215 220 gtc ggc gcc cag gtc gac gag ccg gag cac ggc ggg cgt ccc gac gtg 720
Val Gly Ala Gln Val Asp Glu Pro Glu His Gly Gly Arg Pro Asp Val
225 230 235 240 tgg cgg gtc acc ccg tcc gcg ctg ctc ggc cgg gac ctg gtg gtg gag 768
Trp Arg Val Thr Pro Ser Ala Leu Leu Gly Arg Asp Leu Val Val Glu
245 250 255

```
ccg gac ctg tcg aac gcc cag ccg ttc ctg gcg gcg gcg ctg gtc acc      816
Pro Asp Leu Ser Asn Ala Gln Pro Phe Leu Ala Ala Ala Leu Val Thr
            260                 265                 270

ggc ggc cgg gtc acc gtg ccg gac tgg ccg gcc agg acc acc cag ccc      864
Gly Gly Arg Val Thr Val Pro Asp Trp Pro Ala Arg Thr Thr Gln Pro
        275                 280                 285

ggt gac gcg ctg cgg cag atc ttc acc gag atg ggt ggc tcc tgc gag      912
Gly Asp Ala Leu Arg Gln Ile Phe Thr Glu Met Gly Gly Ser Cys Glu
    290                 295                 300

ctc acc gac cgg ggt ctc acc ttc acc gga acc ggc cgg atc cac ggc      960
Leu Thr Asp Arg Gly Leu Thr Phe Thr Gly Thr Gly Arg Ile His Gly
305                 310                 315                 320

atc gac gtc gac ctc ggc gag gtc ggc gag ctg acc ccg ggc atc gcg     1008
Ile Asp Val Asp Leu Gly Glu Val Gly Glu Leu Thr Pro Gly Ile Ala
                325                 330                 335

gcg gtc gcc gcg ctc gcc gac tcc ccg tcc acc ctg cgc ggg gtg gcg     1056
Ala Val Ala Ala Leu Ala Asp Ser Pro Ser Thr Leu Arg Gly Val Ala
            340                 345                 350

cac ctg cgg ctg cac gag acc gac cgg ctc gcc gcg ctc acc cgg gag     1104
His Leu Arg Leu His Glu Thr Asp Arg Leu Ala Ala Leu Thr Arg Glu
        355                 360                 365

atc aac gcg ctg ggc ggc gac gtc acg gag acc gag gac ggc ctg cac     1152
Ile Asn Ala Leu Gly Gly Asp Val Thr Glu Thr Glu Asp Gly Leu His
    370                 375                 380

atc cgc ccg cgc ccg ctg cac ggc ggc ctc ttc cac acg tac cac gac     1200
Ile Arg Pro Arg Pro Leu His Gly Gly Leu Phe His Thr Tyr His Asp
385                 390                 395                 400

cac cgg atg gcg acc gcg ggc gcg ctc atc ggc ctg gcc gtg aag ggc     1248
His Arg Met Ala Thr Ala Gly Ala Leu Ile Gly Leu Ala Val Lys Gly
                405                 410                 415

gtg gag atc gag aac gtg aag acg acc gag aag acc ttg ccc gac ttc     1296
Val Glu Ile Glu Asn Val Lys Thr Thr Glu Lys Thr Leu Pro Asp Phe
            420                 425                 430

ccc agg atg tgg acc gaa atg ctc gga gtc tga                         1329
Pro Arg Met Trp Thr Glu Met Leu Gly Val  *
        435                 440
```

<210> SEQ ID NO 2
<211> LENGTH: 442
<212> TYPE: PRT
<213> ORGANISM: Unknown
<220> FEATURE:
<223> OTHER INFORMATION: Isolated from soil sample

<400> SEQUENCE: 2

```
Met Thr Asp Ser Asn Pro Ser Thr Asp Pro Leu Thr Gly Arg Trp Pro
1               5                   10                  15

Ala Pro Tyr Ala Ala Gly Ala Val Asp Ala Thr Val Thr Val Pro Gly
            20                  25                  30

Ser Lys Ser Val Thr Asn Arg Ala Leu Val Leu Ala Ala Leu Ala Ala
        35                  40                  45

Glu Pro Gly Trp Val Arg Arg Pro Leu Arg Ser Arg Asp Thr Leu Leu
    50                  55                  60

Met Ala Glu Ala Leu Arg Thr Leu Gly Val Lys Ile Asp Glu Gly Val
65                  70                  75                  80

Gly Pro Asp Gly Thr Gly Glu Ala Trp Arg Ile Ile Pro Ala Gly Leu
                85                  90                  95

Arg Gly Pro Ala Thr Val Asp Val Gly Asn Ala Gly Thr Val Met Arg
            100                 105                 110
```

-continued

```
Phe Leu Pro Pro Val Ala Ala Leu Ala Asn Gly Ala Val Arg Phe Asp
        115                 120                 125

Gly Asp Pro Arg Ser His Glu Arg Pro Leu His Gly Val Ile Asp Ala
    130                 135                 140

Leu Arg Ala Leu Gly Ala Arg Ile Asp Asp Asp Gly Arg Gly Ala Leu
145                 150                 155                 160

Pro Met Thr Val His Gly Ala Gly Gly Leu Glu Gly Gly Val Val Glu
                165                 170                 175

Ile Asp Ala Ser Ser Ser Ser Gln Phe Val Ser Ala Leu Leu Leu Ser
            180                 185                 190

Gly Ala Arg Phe Asn Gln Gly Val Glu Val Arg His Val Gly Thr Arg
        195                 200                 205

Leu Pro Ser Leu Pro His Ile Arg Met Thr Val Asp Met Leu Arg Ala
    210                 215                 220

Val Gly Ala Gln Val Asp Glu Pro Glu His Gly Gly Arg Pro Asp Val
225                 230                 235                 240

Trp Arg Val Thr Pro Ser Ala Leu Leu Gly Arg Asp Leu Val Val Glu
                245                 250                 255

Pro Asp Leu Ser Asn Ala Gln Pro Phe Leu Ala Ala Ala Leu Val Thr
            260                 265                 270

Gly Gly Arg Val Thr Val Pro Asp Trp Pro Ala Arg Thr Thr Gln Pro
        275                 280                 285

Gly Asp Ala Leu Arg Gln Ile Phe Thr Glu Met Gly Gly Ser Cys Glu
    290                 295                 300

Leu Thr Asp Arg Gly Leu Thr Phe Thr Gly Thr Gly Arg Ile His Gly
305                 310                 315                 320

Ile Asp Val Asp Leu Gly Glu Val Gly Glu Leu Thr Pro Gly Ile Ala
                325                 330                 335

Ala Val Ala Ala Leu Ala Asp Ser Pro Ser Thr Leu Arg Gly Val Ala
            340                 345                 350

His Leu Arg Leu His Glu Thr Asp Arg Leu Ala Ala Leu Thr Arg Glu
        355                 360                 365

Ile Asn Ala Leu Gly Gly Asp Val Thr Glu Thr Glu Asp Gly Leu His
    370                 375                 380

Ile Arg Pro Arg Pro Leu His Gly Gly Leu Phe His Thr Tyr His Asp
385                 390                 395                 400

His Arg Met Ala Thr Ala Gly Ala Leu Ile Gly Leu Ala Val Lys Gly
                405                 410                 415

Val Glu Ile Glu Asn Val Lys Thr Thr Glu Lys Thr Leu Pro Asp Phe
            420                 425                 430

Pro Arg Met Trp Thr Glu Met Leu Gly Val
        435                 440
```

```
<210> SEQ ID NO 3
<211> LENGTH: 1326
<212> TYPE: DNA
<213> ORGANISM: Artificial Sequence
<220> FEATURE:
<223> OTHER INFORMATION: synthetic nucleotide sequence encoding syngrg33

<400> SEQUENCE: 3

atg aca gac agc aac cca agc acc gac ccg ctc acc ggc cgc tgg ccg       48

gcg ccc tac gcc gcc ggc gcc gtc gac gcc acc gtc acc gtg cct gga       96

agc aag agc gtc acc aac agg gcg ctg gtg ctg gcg gcg ctg gct gct      144

gaa cct gga tgg gtg cgg cgg ccg ctg agg agc agg gac acc tta ttg      192
```

```
atg gcg gag gcg ctg agg acg ctc ggc gtc aag att gat gaa gga gtt      240

gga cct gat gga act gga gaa gca tgg agg atc atc ccc gcc ggc ctc      288

cgc ggc ccg gcg acg gtg gat gtt ggc aac gcc ggc acc gtg atg agg      336

ttc ctg ccg ccg gtg gcg gcg ctg gcc aac ggc gcc gtc cgc ttc gac      384

ggc gac cca aga agt cat gaa agg cct cta cat ggc gtc atc gac gcg      432

ctc cgc gcg ctg gga gca agg atc gac gac gac ggc cgc ggc gcg ctg      480

cca atg aca gtt cat ggc gcc ggc ggc ctg gag ggc ggc gtg gtg gag      528

att gat gca agc agc agc agc cag ttc gtc tcg gcg ctg ctg ctg agc      576

ggc gcg cgc ttc aac caa gga gtg gag gtg cgg cat gtt gga aca agg      624

ctg cca tca ttg ccg cac atc agg atg acg gtg gac atg ctg cgc gcc      672

gtc ggc gct caa gtt gat gag ccg gag cat gga gga agg cca gat gtt      720

tgg agg gtg acg ccg tcg gcg ctg ctg gga aga gat ctg gtg gtg gag      768

cca gat ctc tca aat gct caa ccc ttc ctg gcg gcg gcg ctg gtg acc      816

ggc ggc cgc gtc acc gtg cca gat tgg ccg gca agg acg acg cag ccc      864

ggc gac gcg ctg cgg cag atc ttc acc gag atg gga gga tca tgt gag      912

ctc acc gac cgc ggc ctc acc ttc acc ggc act gga agg att cat ggc      960

att gat gtg gac ctc ggc gag gtg gga gag ctg acg ccg ggc atc gcc     1008

gcc gtg gcg gcg ctc gcc gac tcg ccg tcg acg ctc cgc ggc gtg gct     1056

cac ctc cgc cta cat gaa aca gat cgg ctg gcg gcg ctg aca agg gag     1104

atc aac gcg ctc ggc ggc gac gtc acc gag aca gaa gat ggc ctc cac     1152

atc agg ccg cgg ccg cta cat gga ggc ctc ttc cac acc tac cat gat     1200

cac agg atg gcc acc gcc ggc gcg ctc atc ggc ctc gcc gtc aag ggc     1248

gtg gag att gaa aat gtg aag aca aca gag aag acg ctg ccg gac ttc     1296

cca agg atg tgg acg gag atg ctg ggc gtc                             1326


<210> SEQ ID NO 4
<211> LENGTH: 1353
<212> TYPE: DNA
<213> ORGANISM: Unknown
<220> FEATURE:
<223> OTHER INFORMATION: isolated from soil
<220> FEATURE:
<221> NAME/KEY: CDS
<222> LOCATION: (1)...(1353)

<400> SEQUENCE: 4

atg acc gca gct tcc ccc gcg cac ccc gat ccg tcg cag ccc gcc gtc       48
Met Thr Ala Ala Ser Pro Ala His Pro Asp Pro Ser Gln Pro Ala Val
1               5                   10                  15

ccc gcc ggc ccg gac ctc tgg ccc gcc ccg tac gcg agc ggc ccc gtc       96
Pro Ala Gly Pro Asp Leu Trp Pro Ala Pro Tyr Ala Ser Gly Pro Val
            20                  25                  30

gac gcg acc gtg acc gtg ccc ggc tcg aag tcg gtc acc aac cgc gcc      144
Asp Ala Thr Val Thr Val Pro Gly Ser Lys Ser Val Thr Asn Arg Ala
        35                  40                  45

ctg gtg ctc gcc gcg ctc gcc gcc gag ccc ggc tgg gtg cgg cgc ccg      192
Leu Val Leu Ala Ala Leu Ala Ala Glu Pro Gly Trp Val Arg Arg Pro
    50                  55                  60

ctc cgc tcc cgc gac acc ctc ctg atg gcc gag ggc ctg cgc acc ctg      240
Leu Arg Ser Arg Asp Thr Leu Leu Met Ala Glu Gly Leu Arg Thr Leu
```

-continued

```
65                  70                  75                  80

ggc gtg aag atc gag gag ggc gtg ggc ccg gac ggc acc ggc gag gcc      288
Gly Val Lys Ile Glu Glu Gly Val Gly Pro Asp Gly Thr Gly Glu Ala
                85                  90                  95

tgg cgg atc atc ccg gcc ccg ctg cgc ggc ggc gcc acg gtc gac gtc      336
Trp Arg Ile Ile Pro Ala Pro Leu Arg Gly Gly Ala Thr Val Asp Val
            100                 105                 110

ggc aac gcg ggc acg gtc atg cgc ttc ctg ccg ccg gtc gcc gcg ctc      384
Gly Asn Ala Gly Thr Val Met Arg Phe Leu Pro Pro Val Ala Ala Leu
        115                 120                 125

gcc gac ggc ccg gtc cgc ttc gac ggc gac ccc cgc tcc cac gag cgc      432
Ala Asp Gly Pro Val Arg Phe Asp Gly Asp Pro Arg Ser His Glu Arg
    130                 135                 140

ccg ctg cac ggg gtg atc gac gcg ctg cgc gcg ctc ggc gcc cgg atc      480
Pro Leu His Gly Val Ile Asp Ala Leu Arg Ala Leu Gly Ala Arg Ile
145                 150                 155                 160

gac gac gag ggc cgc ggc gcc ctc ccg atg acc gtg cac ggc gcc ggc      528
Asp Asp Glu Gly Arg Gly Ala Leu Pro Met Thr Val His Gly Ala Gly
                165                 170                 175

ggc ctg gag ggc ggc acg gtc gag atc gac gcc tcc tcg tcc tcc cag      576
Gly Leu Glu Gly Gly Thr Val Glu Ile Asp Ala Ser Ser Ser Ser Gln
            180                 185                 190

ttc gtc agc gcc ctg ctg ctc tcc ggc gcc cgc ttc aac cag ggc gtc      624
Phe Val Ser Ala Leu Leu Leu Ser Gly Ala Arg Phe Asn Gln Gly Val
        195                 200                 205

gag gtc cgg cac gcg ggc ggc cgg ctg ccg tcg atg ccg cac atc cgg      672
Glu Val Arg His Ala Gly Gly Arg Leu Pro Ser Met Pro His Ile Arg
    210                 215                 220

atg acc gtg gac atg ctc cgc gcg gtg ggc gcg aag gtc gac gag ccg      720
Met Thr Val Asp Met Leu Arg Ala Val Gly Ala Lys Val Asp Glu Pro
225                 230                 235                 240

gag cac ggc ggc gag ccg gac gtg tgg cgg gtg gcc ccg tcg gcg ctg      768
Glu His Gly Gly Glu Pro Asp Val Trp Arg Val Ala Pro Ser Ala Leu
                245                 250                 255

cgc ggc cgc gac ctg gtc atc gag ccc gac ctg tcg aac gcc cag ccg      816
Arg Gly Arg Asp Leu Val Ile Glu Pro Asp Leu Ser Asn Ala Gln Pro
            260                 265                 270

ttc ctg gcg gcc gcg ctg gtc acc ggc ggc cgg gtg acc gtc ccg gac      864
Phe Leu Ala Ala Ala Leu Val Thr Gly Gly Arg Val Thr Val Pro Asp
        275                 280                 285

tgg ccg gcc cgc acc acc cag ccc ggc gac gag ctg cgc cgc atc ttc      912
Trp Pro Ala Arg Thr Thr Gln Pro Gly Asp Glu Leu Arg Arg Ile Phe
    290                 295                 300

acc gag atg ggc ggc gcc tgc gag ctc acc gac gcc ggt ctc acc ttc      960
Thr Glu Met Gly Gly Ala Cys Glu Leu Thr Asp Ala Gly Leu Thr Phe
305                 310                 315                 320

acc ggc acc ggc cgg atc cac ggc atc gac gtg gac ctc ggc gag gtc     1008
Thr Gly Thr Gly Arg Ile His Gly Ile Asp Val Asp Leu Gly Glu Val
                325                 330                 335

ggc gag ctg acc ccc ggc atc gcg gcg gtc gcc gcc ctc gcc gac tcc     1056
Gly Glu Leu Thr Pro Gly Ile Ala Ala Val Ala Ala Leu Ala Asp Ser
            340                 345                 350

ccc tcc acc ctg cgc ggc gtg gcc cac ctg cgg ctc cac gag acc gac     1104
Pro Ser Thr Leu Arg Gly Val Ala His Leu Arg Leu His Glu Thr Asp
        355                 360                 365

cgg ctc gcg gcg ctc acc cgg gag atc aac ggt ctg ggc ggc gac gtc     1152
Arg Leu Ala Ala Leu Thr Arg Glu Ile Asn Gly Leu Gly Gly Asp Val
    370                 375                 380

acc gag acc gag gac ggc ctg cac atc cgg ccg cgc ccg ctg acc ggc     1200
Thr Glu Thr Glu Asp Gly Leu His Ile Arg Pro Arg Pro Leu Thr Gly
```

-continued

```
385                 390                 395                 400

ggc gtc ttc cac acg tac cac gac cac cgg atg gcg acc gcg ggc gcg      1248
Gly Val Phe His Thr Tyr His Asp His Arg Met Ala Thr Ala Gly Ala
                405                 410                 415

atc atc ggc ctc gcc gtg aag ggc gtg gag atc gag gac gtg gcg acg      1296
Ile Ile Gly Leu Ala Val Lys Gly Val Glu Ile Glu Asp Val Ala Thr
            420                 425                 430

acc gcc aag acc ttg ccg gac ttc ccg ggg atg tgg acc gaa atg ctc      1344
Thr Ala Lys Thr Leu Pro Asp Phe Pro Gly Met Trp Thr Glu Met Leu
        435                 440                 445

gga gcc tga                                                          1353
Gly Ala  *
    450


<210> SEQ ID NO 5
<211> LENGTH: 450
<212> TYPE: PRT
<213> ORGANISM: Unknown
<220> FEATURE:
<223> OTHER INFORMATION: isolated from soil

<400> SEQUENCE: 5

Met Thr Ala Ala Ser Pro Ala His Pro Asp Pro Ser Gln Pro Ala Val
1               5                   10                  15

Pro Ala Gly Pro Asp Leu Trp Pro Ala Pro Tyr Ala Ser Gly Pro Val
            20                  25                  30

Asp Ala Thr Val Thr Val Pro Gly Ser Lys Ser Val Thr Asn Arg Ala
        35                  40                  45

Leu Val Leu Ala Ala Leu Ala Ala Glu Pro Gly Trp Val Arg Arg Pro
    50                  55                  60

Leu Arg Ser Arg Asp Thr Leu Leu Met Ala Glu Gly Leu Arg Thr Leu
65                  70                  75                  80

Gly Val Lys Ile Glu Glu Gly Val Gly Pro Asp Gly Thr Gly Glu Ala
                85                  90                  95

Trp Arg Ile Ile Pro Ala Pro Leu Arg Gly Gly Ala Thr Val Asp Val
            100                 105                 110

Gly Asn Ala Gly Thr Val Met Arg Phe Leu Pro Pro Val Ala Ala Leu
        115                 120                 125

Ala Asp Gly Pro Val Arg Phe Asp Gly Asp Pro Arg Ser His Glu Arg
    130                 135                 140

Pro Leu His Gly Val Ile Asp Ala Leu Arg Ala Leu Gly Ala Arg Ile
145                 150                 155                 160

Asp Asp Glu Gly Arg Gly Ala Leu Pro Met Thr Val His Gly Ala Gly
                165                 170                 175

Gly Leu Glu Gly Gly Thr Val Glu Ile Asp Ala Ser Ser Ser Ser Gln
            180                 185                 190

Phe Val Ser Ala Leu Leu Leu Ser Gly Ala Arg Phe Asn Gln Gly Val
        195                 200                 205

Glu Val Arg His Ala Gly Gly Arg Leu Pro Ser Met Pro His Ile Arg
    210                 215                 220

Met Thr Val Asp Met Leu Arg Ala Val Gly Ala Lys Val Asp Glu Pro
225                 230                 235                 240

Glu His Gly Gly Glu Pro Asp Val Trp Arg Val Ala Pro Ser Ala Leu
                245                 250                 255

Arg Gly Arg Asp Leu Val Ile Glu Pro Asp Leu Ser Asn Ala Gln Pro
            260                 265                 270

Phe Leu Ala Ala Ala Leu Val Thr Gly Gly Arg Val Thr Val Pro Asp
```

-continued

```
        275                 280                 285

Trp Pro Ala Arg Thr Thr Gln Pro Gly Asp Glu Leu Arg Arg Ile Phe
    290                 295                 300

Thr Glu Met Gly Gly Ala Cys Glu Leu Thr Asp Ala Gly Leu Thr Phe
305                 310                 315                 320

Thr Gly Thr Gly Arg Ile His Gly Ile Asp Val Asp Leu Gly Glu Val
                325                 330                 335

Gly Glu Leu Thr Pro Gly Ile Ala Ala Val Ala Ala Leu Ala Asp Ser
            340                 345                 350

Pro Ser Thr Leu Arg Gly Val Ala His Leu Arg Leu His Glu Thr Asp
        355                 360                 365

Arg Leu Ala Ala Leu Thr Arg Glu Ile Asn Gly Leu Gly Gly Asp Val
    370                 375                 380

Thr Glu Thr Glu Asp Gly Leu His Ile Arg Pro Arg Pro Leu Thr Gly
385                 390                 395                 400

Gly Val Phe His Thr Tyr His Asp His Arg Met Ala Thr Ala Gly Ala
                405                 410                 415

Ile Ile Gly Leu Ala Val Lys Gly Val Glu Ile Glu Asp Val Ala Thr
            420                 425                 430

Thr Ala Lys Thr Leu Pro Asp Phe Pro Gly Met Trp Thr Glu Met Leu
        435                 440                 445

Gly Ala
    450


<210> SEQ ID NO 6
<211> LENGTH: 1326
<212> TYPE: DNA
<213> ORGANISM: Artificial Sequence
<220> FEATURE:
<223> OTHER INFORMATION: synthetic nucleotide sequence encoding syngrg35

<400> SEQUENCE: 6

gttgatccaa gccagccggc ggtgccggcg gggccggacc tctggccggc gccatatgct     60

tctgggccgg tggacgccac cgtcaccgtg cctggaagca agagcgtcac caacagggcg    120

ctggtgctgg cggcgctggc tgctgaacct ggatgggtgc ggcggccgct gaggagcagg    180

gacaccttgc tgatggcaga agggctaagg acgctcggcg tcaagatcga ggagggcgtc    240

ggccctgatg gaactggaga agcatggagg atcatcccgg cgccgctccg cggcggcgcc    300

accgtcgacg tcggcaacgc cggcaccgtg atgaggttcc tgccgccggt ggcggcgctc    360

gccgacgggc cggtgagatt tgatggagat ccaagaagtc atgaaaggcc tctacatggc    420

gtcatcgacg cgctccgcgc gctcggcgcc aggattgatg atgaaggccg cggcgcgctg    480

ccaatgacag ttcatggcgc cggcggcctg gaaggaggaa cagtggagat tgatgcaagc    540

agcagcagcc agttcgtctc ggcgctgctg ctgagcggcg cgcgcttcaa ccaaggagtg    600

gaggtgcggc acgccggcgg ccggctgcca tcaatgcctc acatcaggat gacggtggac    660

atgctgcgcg ccgtcggcgc caaggtggat gagccggagc atggaggaga acctgatgtt    720

tggagggtgg cgccgtcggc gctccgcggc cgcgacctgg tgattgagcc agatctctca    780

aatgctcaac ccttcctggc ggcggcgctg gtgaccggcg gccgcgtcac cgtgccagat    840

tggccggcaa ggacgacgca gcccggcgac gagctaagga ggatcttcac cgagatgggc    900

ggcgcctgcg agctcaccga cgccggcctc accttcaccg gcactggaag gattcatggc    960

attgatgtgg acctcggcga ggtgggagag ctgacgccgg gcatcgccgc cgtggcggcg   1020

ctcgccgact cgccgtcgac gctccgcggc gtggctcacc tccgcctaca tgaaacagat   1080
```

```
cggctggcgg cgctgacaag ggagatcaat ggcctcggcg gcgacgtcac cgagacagaa   1140

gatggactac acatcaggcc gcggccgctc accggcggcg tcttccacac ctaccatgat   1200

cacaggatgg ccaccgccgg cgccatcatc ggcctcgccg tgaagggcgt ggagattgaa   1260

gatgtggcca ccaccgccaa gacgctgccg gacttccctg ggatgtggac ggagatgctg   1320

ggcgcc                                                              1326


<210> SEQ ID NO 7
<211> LENGTH: 1344
<212> TYPE: DNA
<213> ORGANISM: Unknown
<220> FEATURE:
<223> OTHER INFORMATION: isolated from soil
<220> FEATURE:
<221> NAME/KEY: CDS
<222> LOCATION: (1)...(1344)

<400> SEQUENCE: 7

atg aaa aat caa aat ttt gat gct aaa gcc cgt agc ccg tgg aca ccg       48
Met Lys Asn Gln Asn Phe Asp Ala Lys Ala Arg Ser Pro Trp Thr Pro
1               5                   10                  15

tta aaa ggt gta aat aag ata agt gtt tca cct agt aaa gga aga ata       96
Leu Lys Gly Val Asn Lys Ile Ser Val Ser Pro Ser Lys Gly Arg Ile
            20                  25                  30

aat gga acc gtt act att cct ggt agc aag agt tta acc aac aga gct      144
Asn Gly Thr Val Thr Ile Pro Gly Ser Lys Ser Leu Thr Asn Arg Ala
        35                  40                  45

tta atc ata agt tct cta gct agt gga aag tca aaa gtg caa ggt att      192
Leu Ile Ile Ser Ser Leu Ala Ser Gly Lys Ser Lys Val Gln Gly Ile
    50                  55                  60

tta aaa agc gat gat tca ttt tgg tgt tta gac tcc ttg aaa aag cta      240
Leu Lys Ser Asp Asp Ser Phe Trp Cys Leu Asp Ser Leu Lys Lys Leu
65                  70                  75                  80

gga gta aat gtg aaa att caa gga gat aca gct ttt atc gaa gga aac      288
Gly Val Asn Val Lys Ile Gln Gly Asp Thr Ala Phe Ile Glu Gly Asn
                85                  90                  95

ggt ggt aaa tgg gaa tca ggt gat tta tat att ggt gca gca gga acg      336
Gly Gly Lys Trp Glu Ser Gly Asp Leu Tyr Ile Gly Ala Ala Gly Thr
            100                 105                 110

att gca cga ttt cta cct gga gca tta gca gtt tca ggt aca ggc ata      384
Ile Ala Arg Phe Leu Pro Gly Ala Leu Ala Val Ser Gly Thr Gly Ile
        115                 120                 125

tgg gag tta gaa gcc agt aaa agt atg agt aaa cga cct att tca ccc      432
Trp Glu Leu Glu Ala Ser Lys Ser Met Ser Lys Arg Pro Ile Ser Pro
    130                 135                 140

tta gta gat gct tta aaa gag ctt ggg gct gaa ata aca tat cta agc      480
Leu Val Asp Ala Leu Lys Glu Leu Gly Ala Glu Ile Thr Tyr Leu Ser
145                 150                 155                 160

gat caa ggc tac tat ccg ttg tta gtt aaa gga aaa caa cta aat ggg      528
Asp Gln Gly Tyr Tyr Pro Leu Leu Val Lys Gly Lys Gln Leu Asn Gly
                165                 170                 175

ggc gag gtt gaa ctc tca ggt aga att tct agt cag ttt ata agt ggt      576
Gly Glu Val Glu Leu Ser Gly Arg Ile Ser Ser Gln Phe Ile Ser Gly
            180                 185                 190

cta ttg att gcc tcg cct tat tta aat gat cca atc aag att aat att      624
Leu Leu Ile Ala Ser Pro Tyr Leu Asn Asp Pro Ile Lys Ile Asn Ile
        195                 200                 205

aaa gat cac atc gtt caa cac tca tat gta ctc tta act ttg gaa tta      672
Lys Asp His Ile Val Gln His Ser Tyr Val Leu Leu Thr Leu Glu Leu
    210                 215                 220
```

-continued

```
atg aaa aag ttt ggt gca aaa gtt aaa tac gat agt agc cta aaa gaa      720
Met Lys Lys Phe Gly Ala Lys Val Lys Tyr Asp Ser Ser Leu Lys Glu
225                 230                 235                 240

ata gtc gtc tat cca tct aag tac act cca caa gat ata aat tta gaa      768
Ile Val Val Tyr Pro Ser Lys Tyr Thr Pro Gln Asp Ile Asn Leu Glu
                245                 250                 255

gca gat gtt tcc act gca tgt tat ttt ctg gct ctt gct gca gtg acc      816
Ala Asp Val Ser Thr Ala Cys Tyr Phe Leu Ala Leu Ala Ala Val Thr
            260                 265                 270

aac ggt aaa gta caa att gat aat cta act tat gaa aca aaa caa cca      864
Asn Gly Lys Val Gln Ile Asp Asn Leu Thr Tyr Glu Thr Lys Gln Pro
        275                 280                 285

gat ata aaa atg gtt gat atc ctt gaa cgg atg gga tgc aaa gta aca      912
Asp Ile Lys Met Val Asp Ile Leu Glu Arg Met Gly Cys Lys Val Thr
    290                 295                 300

aga ggt tct tca ttc att gaa ata gag gga gtt agt caa tta aaa ggt      960
Arg Gly Ser Ser Phe Ile Glu Ile Glu Gly Val Ser Gln Leu Lys Gly
305                 310                 315                 320

gga ttt gaa atc tct atg agg gaa atg tct gac caa gtg tta act cta     1008
Gly Phe Glu Ile Ser Met Arg Glu Met Ser Asp Gln Val Leu Thr Leu
                325                 330                 335

gca gca att gct cca ttc gca gat gaa cca ata acc ata aaa gac gtt     1056
Ala Ala Ile Ala Pro Phe Ala Asp Glu Pro Ile Thr Ile Lys Asp Val
            340                 345                 350

gaa cat ata cgc cat cac gaa tca aat cga atc agt gta cta gtt gat     1104
Glu His Ile Arg His His Glu Ser Asn Arg Ile Ser Val Leu Val Asp
        355                 360                 365

tca cta tct agg tta gga att ata gta gaa gaa ttt aaa gat gga cta     1152
Ser Leu Ser Arg Leu Gly Ile Ile Val Glu Glu Phe Lys Asp Gly Leu
    370                 375                 380

aaa gtg tat ccg ggt aat ccg aaa gcc act tta cta gat aca cac gat     1200
Lys Val Tyr Pro Gly Asn Pro Lys Ala Thr Leu Leu Asp Thr His Asp
385                 390                 395                 400

gat cat aga gtt gca atg gca tta tca ctt ata ggt tca aga gtt gaa     1248
Asp His Arg Val Ala Met Ala Leu Ser Leu Ile Gly Ser Arg Val Glu
                405                 410                 415

ggt ata caa ata aat gat cca gga tgt gta tct aaa act tgt cct cag     1296
Gly Ile Gln Ile Asn Asp Pro Gly Cys Val Ser Lys Thr Cys Pro Gln
            420                 425                 430

tat ttt gaa tta ttg gaa aaa cta ggt ttg aat ata att aaa cat tga     1344
Tyr Phe Glu Leu Leu Glu Lys Leu Gly Leu Asn Ile Ile Lys His  *
        435                 440                 445


<210> SEQ ID NO 8
<211> LENGTH: 447
<212> TYPE: PRT
<213> ORGANISM: Unknown
<220> FEATURE:
<223> OTHER INFORMATION: isolated from soil

<400> SEQUENCE: 8

Met Lys Asn Gln Asn Phe Asp Ala Lys Ala Arg Ser Pro Trp Thr Pro
1               5                   10                  15

Leu Lys Gly Val Asn Lys Ile Ser Val Ser Pro Ser Lys Gly Arg Ile
            20                  25                  30

Asn Gly Thr Val Thr Ile Pro Gly Ser Lys Ser Leu Thr Asn Arg Ala
        35                  40                  45

Leu Ile Ile Ser Ser Leu Ala Ser Gly Lys Ser Lys Val Gln Gly Ile
    50                  55                  60

Leu Lys Ser Asp Asp Ser Phe Trp Cys Leu Asp Ser Leu Lys Lys Leu
65                  70                  75                  80
```

-continued

```
Gly Val Asn Val Lys Ile Gln Gly Asp Thr Ala Phe Ile Glu Gly Asn
                85                  90                  95

Gly Gly Lys Trp Glu Ser Gly Asp Leu Tyr Ile Gly Ala Ala Gly Thr
            100                 105                 110

Ile Ala Arg Phe Leu Pro Gly Ala Leu Ala Val Ser Gly Thr Gly Ile
        115                 120                 125

Trp Glu Leu Glu Ala Ser Lys Ser Met Ser Lys Arg Pro Ile Ser Pro
    130                 135                 140

Leu Val Asp Ala Leu Lys Glu Leu Gly Ala Glu Ile Thr Tyr Leu Ser
145                 150                 155                 160

Asp Gln Gly Tyr Tyr Pro Leu Leu Val Lys Gly Lys Gln Leu Asn Gly
                165                 170                 175

Gly Glu Val Glu Leu Ser Gly Arg Ile Ser Ser Gln Phe Ile Ser Gly
            180                 185                 190

Leu Leu Ile Ala Ser Pro Tyr Leu Asn Asp Pro Ile Lys Ile Asn Ile
        195                 200                 205

Lys Asp His Ile Val Gln His Ser Tyr Val Leu Leu Thr Leu Glu Leu
    210                 215                 220

Met Lys Lys Phe Gly Ala Lys Val Lys Tyr Asp Ser Ser Leu Lys Glu
225                 230                 235                 240

Ile Val Val Tyr Pro Ser Lys Tyr Thr Pro Gln Asp Ile Asn Leu Glu
                245                 250                 255

Ala Asp Val Ser Thr Ala Cys Tyr Phe Leu Ala Leu Ala Ala Val Thr
            260                 265                 270

Asn Gly Lys Val Gln Ile Asp Asn Leu Thr Tyr Glu Thr Lys Gln Pro
        275                 280                 285

Asp Ile Lys Met Val Asp Ile Leu Glu Arg Met Gly Cys Lys Val Thr
    290                 295                 300

Arg Gly Ser Ser Phe Ile Glu Ile Glu Gly Val Ser Gln Leu Lys Gly
305                 310                 315                 320

Gly Phe Glu Ile Ser Met Arg Glu Met Ser Asp Gln Val Leu Thr Leu
                325                 330                 335

Ala Ala Ile Ala Pro Phe Ala Asp Glu Pro Ile Thr Ile Lys Asp Val
            340                 345                 350

Glu His Ile Arg His His Glu Ser Asn Arg Ile Ser Val Leu Val Asp
        355                 360                 365

Ser Leu Ser Arg Leu Gly Ile Ile Val Glu Glu Phe Lys Asp Gly Leu
    370                 375                 380

Lys Val Tyr Pro Gly Asn Pro Lys Ala Thr Leu Leu Asp Thr His Asp
385                 390                 395                 400

Asp His Arg Val Ala Met Ala Leu Ser Leu Ile Gly Ser Arg Val Glu
                405                 410                 415

Gly Ile Gln Ile Asn Asp Pro Gly Cys Val Ser Lys Thr Cys Pro Gln
            420                 425                 430

Tyr Phe Glu Leu Leu Glu Lys Leu Gly Leu Asn Ile Ile Lys His
        435                 440                 445
```

<210> SEQ ID NO 9
<211> LENGTH: 1344
<212> TYPE: DNA
<213> ORGANISM: Artificial Sequence
<220> FEATURE:
<223> OTHER INFORMATION: synthetic nucleotide sequence encoding GRG36
(syngrg36)

<400> SEQUENCE: 9

```
atgaagaacc agaacttcga cgccaaggca agaagcccct ggacgccgct caagggcgtc      60

aacaagatct ccgtctcgcc aagcaaagga aggatcaatg gcaccgtcac catccctgga     120

agcaagagct tgacaaatag agctctcatc atcagcagct tagcaagcgg caagagcaag     180

gttcaaggca tcctcaagag cgacgacagc ttctggtgcc tggattcatt gaagaagctc     240

ggcgtcaatg tgaagatcca aggagacacc gccttcattg aaggaaatgg aggaaaatgg     300

gagagtggag atctctacat cggcgccgcc ggcaccattg caagatttct tcctggcgcg     360

ctggcggtga gcggcaccgg catctgggag ctggaggcaa gcaagagcat gagcaagagg     420

cccatctcac cgctggtgga tgctctcaag gagctcggcg ccgagatcac ctacctctct     480

gatcaaggct actacccgct gctggtgaag ggcaagcagc tcaatggagg agaggtggag     540

ctctctggaa ggatcagcag ccagttcatc agcggcctgc tgattgcttc accatatttg     600

aatgatccca tcaagatcaa catcaaggac cacatcgtgc agcacagcta tgtgctgctg     660

acgctggagc tgatgaagaa gttcggcgcc aaggtgaagt acgacagcag cttgaaggag     720

atcgtcgtct acccaagcaa gtacacgccg caggacatca acctggaagc tgatgtttca     780

acagcatgct acttcctggc gctggcggcg gtgacaaatg gcaaggtgca aattgacaac     840

ctcacctacg agaccaagca gccggacatc aagatggtgg acatcctgga gaggatgggc     900

tgcaaggtga caagaggaag cagcttcatc gagattgaag gagtgagcca gctgaagggc     960

ggcttcgaga tctcaatgag ggagatgagc gaccaggtgc tgacgctggc ggccatcgcg    1020

ccatttgctg atgagcccat caccatcaag gatgtggagc acatccgcca tcatgaaagc    1080

aacaggatct ccgtgctggt ggacagcctc tcaaggctgg gcatcatcgt ggaggagttc    1140

aaggatggcc tcaaggtgta ccctggaaat ccaaaggcga cgctgctgga cacccatgat    1200

gatcaccgcg tggcaatggc gctgagcttg attggatcaa gggtggaagg catccagatc    1260

aatgatcctg gctgcgtcag caagacctgc cctcaatatt ttgagctgct ggagaagctg    1320

ggcctcaaca tcatcaagca ctag                                           1344
```

```
<210> SEQ ID NO 10
<211> LENGTH: 1407
<212> TYPE: DNA
<213> ORGANISM: Unknown
<220> FEATURE:
<223> OTHER INFORMATION: isolated from soil
<220> FEATURE:
<221> NAME/KEY: CDS
<222> LOCATION: (1)...(1407)

<400> SEQUENCE: 10

atg aca gca tca ccc atg ggc gcg tcc gct gac aac tcc ggc gct gct       48
Met Thr Ala Ser Pro Met Gly Ala Ser Ala Asp Asn Ser Gly Ala Ala
1               5                   10                  15

ccg cac tgg ccc gcg ccg ttt gcg gag cag ccc gtt gac gcc acg gtc       96
Pro His Trp Pro Ala Pro Phe Ala Glu Gln Pro Val Asp Ala Thr Val
            20                  25                  30

cgc gtg ccg ggc tcc aag tcg ctg acc aac agg tac ctg gtg ctc gcc      144
Arg Val Pro Gly Ser Lys Ser Leu Thr Asn Arg Tyr Leu Val Leu Ala
        35                  40                  45

gcg ctg gcc gac ggg ccg tcc cgg ctc cgg gcg ccg ctg cat tcc cgc      192
Ala Leu Ala Asp Gly Pro Ser Arg Leu Arg Ala Pro Leu His Ser Arg
    50                  55                  60

gac tca gcg ctg atg atc gcc gcc ctg cgc cag ctc ggc gcg gac atc      240
Asp Ser Ala Leu Met Ile Ala Ala Leu Arg Gln Leu Gly Ala Asp Ile
65                  70                  75                  80
```

-continued

```
cgg gag gtg ccg ggc gac ggc gcc ttc ggc ccg gac ctg gag gtg acg       288
Arg Glu Val Pro Gly Asp Gly Ala Phe Gly Pro Asp Leu Glu Val Thr
                85                  90                  95

ccg att ccg gca aac gcc ggg ggt gcc gac gtc gcc atc gac tgc ggc       336
Pro Ile Pro Ala Asn Ala Gly Gly Ala Asp Val Ala Ile Asp Cys Gly
            100                 105                 110

ctg gcc ggg acc gtc atg agg ttt gtt ccg ccg ctg gcg gcg ctc cgc       384
Leu Ala Gly Thr Val Met Arg Phe Val Pro Pro Leu Ala Ala Leu Arg
        115                 120                 125

agc ggt acc acc gtt ttc gac ggc gat ccc cac gcc cgg gag cgc ccg       432
Ser Gly Thr Thr Val Phe Asp Gly Asp Pro His Ala Arg Glu Arg Pro
    130                 135                 140

atg ggg acc atc atc gag gcg ctt gcg ggc ctt ggc gtt acc gtc agc       480
Met Gly Thr Ile Ile Glu Ala Leu Ala Gly Leu Gly Val Thr Val Ser
145                 150                 155                 160

ggc gag gac ggc gga acg cct gct tca ctg ccg ttc cgc gtc gaa ggc       528
Gly Glu Asp Gly Gly Thr Pro Ala Ser Leu Pro Phe Arg Val Glu Gly
                165                 170                 175

acc ggg cag gtc cgc ggc ggg cac ctc gtc ata gac gcc agc gcc tcc       576
Thr Gly Gln Val Arg Gly Gly His Leu Val Ile Asp Ala Ser Ala Ser
            180                 185                 190

tcc cag ttc gtc tcc gcg ctg ctg ctg gtg ggg gcc cgg ttc acg gac       624
Ser Gln Phe Val Ser Ala Leu Leu Leu Val Gly Ala Arg Phe Thr Asp
        195                 200                 205

ggc ctg cat ctg gag cac tcc ggc agc acc gtg ccg agc ctg gac cac       672
Gly Leu His Leu Glu His Ser Gly Ser Thr Val Pro Ser Leu Asp His
    210                 215                 220

atc aac atg acc atc gct acg ctg cgc ggc gcg ggc gtg gcg gtg gat       720
Ile Asn Met Thr Ile Ala Thr Leu Arg Gly Ala Gly Val Ala Val Asp
225                 230                 235                 240

gac tcc acg ccc aac cac tgg att gtg ggc ccc ggg ccg atc cgc gcc       768
Asp Ser Thr Pro Asn His Trp Ile Val Gly Pro Gly Pro Ile Arg Ala
                245                 250                 255

ttc gac cag cgg atc gag cag gac ctg tcc aac gcc ggc ccg ttc ctg       816
Phe Asp Gln Arg Ile Glu Gln Asp Leu Ser Asn Ala Gly Pro Phe Leu
            260                 265                 270

gcg gcc gcg ctg gca acc ggc ggc acg gtg cgg att ccg gac tgg ccg       864
Ala Ala Ala Leu Ala Thr Gly Gly Thr Val Arg Ile Pro Asp Trp Pro
        275                 280                 285

gag cac acc acg cag gtg ggt gac atg tgg cgc agt atc ctc agt gac       912
Glu His Thr Thr Gln Val Gly Asp Met Trp Arg Ser Ile Leu Ser Asp
    290                 295                 300

atg ggg gca acc gtc acc ctg cag gac ggc acc ctg acc gtg acc ggc       960
Met Gly Ala Thr Val Thr Leu Gln Asp Gly Thr Leu Thr Val Thr Gly
305                 310                 315                 320

ggc agc aaa atc aac ggc gcg gac ttc gcc gag acc agc gaa ctg gcg      1008
Gly Ser Lys Ile Asn Gly Ala Asp Phe Ala Glu Thr Ser Glu Leu Ala
                325                 330                 335

ccc acc gtc gct gcg ctc tgc gcg ctg gca tcc ggt ccc tcg cgg ctg      1056
Pro Thr Val Ala Ala Leu Cys Ala Leu Ala Ser Gly Pro Ser Arg Leu
            340                 345                 350

acc ggc atc gcc cac ctc cgg gga cat gag acg gac cgg ctc gcc gcg      1104
Thr Gly Ile Ala His Leu Arg Gly His Glu Thr Asp Arg Leu Ala Ala
        355                 360                 365

ctc gtc acc gaa atc aac cgc ctc ggc ggc gat gcc gag gaa acc gcc      1152
Leu Val Thr Glu Ile Asn Arg Leu Gly Gly Asp Ala Glu Glu Thr Ala
    370                 375                 380

gac gga ctc gtc atc cgc ccc gcg gaa ctg cac gcg ggg gtg gtg cac      1200
Asp Gly Leu Val Ile Arg Pro Ala Glu Leu His Ala Gly Val Val His
385                 390                 395                 400
```

-continued

```
agc tac gcg gac cac cgg atg gcc aca gcc gga gcc atc ctc ggc ctg      1248
Ser Tyr Ala Asp His Arg Met Ala Thr Ala Gly Ala Ile Leu Gly Leu
                405                 410                 415

gcg gtc agg ggc gtg gaa gtg cag gac atc gcc acc aca tcc aag acc      1296
Ala Val Arg Gly Val Glu Val Gln Asp Ile Ala Thr Thr Ser Lys Thr
            420                 425                 430

atg ccg gac ttc ccc aag ctg tgg gcg gac atg ctc ggc cgg cag acc      1344
Met Pro Asp Phe Pro Lys Leu Trp Ala Asp Met Leu Gly Arg Gln Thr
        435                 440                 445

gat gca gct aca aac aca gcg ggt acc aac acc gcg ggg acc gcc ggt      1392
Asp Ala Ala Thr Asn Thr Ala Gly Thr Asn Thr Ala Gly Thr Ala Gly
    450                 455                 460

ggc acg cag cac tga                                                  1407
Gly Thr Gln His  *
465


<210> SEQ ID NO 11
<211> LENGTH: 468
<212> TYPE: PRT
<213> ORGANISM: Unknown
<220> FEATURE:
<223> OTHER INFORMATION: isolated from soil

<400> SEQUENCE: 11

Met Thr Ala Ser Pro Met Gly Ala Ser Ala Asp Asn Ser Gly Ala Ala
1               5                   10                  15

Pro His Trp Pro Ala Pro Phe Ala Glu Gln Pro Val Asp Ala Thr Val
            20                  25                  30

Arg Val Pro Gly Ser Lys Ser Leu Thr Asn Arg Tyr Leu Val Leu Ala
        35                  40                  45

Ala Leu Ala Asp Gly Pro Ser Arg Leu Arg Ala Pro Leu His Ser Arg
    50                  55                  60

Asp Ser Ala Leu Met Ile Ala Ala Leu Arg Gln Leu Gly Ala Asp Ile
65                  70                  75                  80

Arg Glu Val Pro Gly Asp Gly Ala Phe Gly Pro Asp Leu Glu Val Thr
                85                  90                  95

Pro Ile Pro Ala Asn Ala Gly Gly Ala Asp Val Ala Ile Asp Cys Gly
            100                 105                 110

Leu Ala Gly Thr Val Met Arg Phe Val Pro Pro Leu Ala Ala Leu Arg
        115                 120                 125

Ser Gly Thr Thr Val Phe Asp Gly Asp Pro His Ala Arg Glu Arg Pro
    130                 135                 140

Met Gly Thr Ile Ile Glu Ala Leu Ala Gly Leu Gly Val Thr Val Ser
145                 150                 155                 160

Gly Glu Asp Gly Gly Thr Pro Ala Ser Leu Pro Phe Arg Val Glu Gly
                165                 170                 175

Thr Gly Gln Val Arg Gly Gly His Leu Val Ile Asp Ala Ser Ala Ser
            180                 185                 190

Ser Gln Phe Val Ser Ala Leu Leu Leu Val Gly Ala Arg Phe Thr Asp
        195                 200                 205

Gly Leu His Leu Glu His Ser Gly Ser Thr Val Pro Ser Leu Asp His
    210                 215                 220

Ile Asn Met Thr Ile Ala Thr Leu Arg Gly Ala Gly Val Ala Val Asp
225                 230                 235                 240

Asp Ser Thr Pro Asn His Trp Ile Val Gly Pro Gly Pro Ile Arg Ala
                245                 250                 255

Phe Asp Gln Arg Ile Glu Gln Asp Leu Ser Asn Ala Gly Pro Phe Leu
            260                 265                 270
```

```
Ala Ala Ala Leu Ala Thr Gly Gly Thr Val Arg Ile Pro Asp Trp Pro
        275                 280                 285

Glu His Thr Thr Gln Val Gly Asp Met Trp Arg Ser Ile Leu Ser Asp
    290                 295                 300

Met Gly Ala Thr Val Thr Leu Gln Asp Gly Thr Leu Thr Val Thr Gly
305                 310                 315                 320

Gly Ser Lys Ile Asn Gly Ala Asp Phe Ala Glu Thr Ser Glu Leu Ala
                325                 330                 335

Pro Thr Val Ala Ala Leu Cys Ala Leu Ala Ser Gly Pro Ser Arg Leu
            340                 345                 350

Thr Gly Ile Ala His Leu Arg Gly His Glu Thr Asp Arg Leu Ala Ala
        355                 360                 365

Leu Val Thr Glu Ile Asn Arg Leu Gly Gly Asp Ala Glu Glu Thr Ala
    370                 375                 380

Asp Gly Leu Val Ile Arg Pro Ala Glu Leu His Ala Gly Val Val His
385                 390                 395                 400

Ser Tyr Ala Asp His Arg Met Ala Thr Ala Gly Ala Ile Leu Gly Leu
                405                 410                 415

Ala Val Arg Gly Val Glu Val Gln Asp Ile Ala Thr Thr Ser Lys Thr
            420                 425                 430

Met Pro Asp Phe Pro Lys Leu Trp Ala Asp Met Leu Gly Arg Gln Thr
        435                 440                 445

Asp Ala Ala Thr Asn Thr Ala Gly Thr Asn Thr Ala Gly Thr Ala Gly
    450                 455                 460

Gly Thr Gln His
465
```

<210> SEQ ID NO 12
<211> LENGTH: 1404
<212> TYPE: DNA
<213> ORGANISM: Artificial Sequence
<220> FEATURE:
<223> OTHER INFORMATION: synthetic nucleotide sequence encoding GRG37
(syngrg37)

<400> SEQUENCE: 12

```
atgacagctt ctccaatggg cgcctccgcc gacaacagcg gcgccgcgcc gcactggccg     60

gcgcccttcg ccgagcagcc ggtggacgcc accgtccgcg tgcctggaag caagagcctc    120

accaacagat atttggtgct ggcggcgctg gctgatgggc catcaaggct ccgcgcgccg    180

ctgcattcaa gagattcggc gctgatgatc gccgcgctcc gtcagctcgg cgccgacatc    240

agggaggtgc ccggcgacgg cgccttcggc cctgatctgg aggtgacgcc catcccggcc    300

aacgccggcg gcgccgacgt cgccatcgac tgcggcctcg ccggcaccgt gatgaggttc    360

gtgccgccgc tggcggcgct gagatcaggc accaccgtct ttgatggaga tcctcatgca    420

agagaaaggc caatgggcac catcatcgag gcgctcgccg gcctcggcgt caccgtcagc    480

ggcgaggacg gcggcacgcc ggcgtcgctg cccttccgcg tggaaggaac tggtcaagtt    540

cgcggcggcc acctggtgat tgatgcttca gcaagcagcc agttcgtctc ggcgctgctg    600

ctggtgggag caaggttcac cgacggcctc cacctggagc acagcggcag caccgtgcca    660

agcctggatc acatcaacat gaccatcgcc accctccgcg gcgccggcgt cgccgtggat    720

gattcaacgc ccaaccactg gatcgtcggc cccggcccca tcagggcatt tgatcaaaga    780

attgagcaag atctttcaaa tgctggaccc ttcctggcgg cggcgctggc caccggcggc    840

accgtgagga ttccagattg gccggagcac accacccaag ttggtgacat gtggaggagc    900
```

```
atcctctccg acatgggcgc caccgtcacc cttcaagatg gcaccttgac cgtcaccggc    960

ggcagcaaga tcaacggcgc cgacttcgcc gagacatcag agctggcgcc gacggtggcg   1020

gcgctctgcg cgctggcttc tggccaagc cgcctcaccg gcattgctca cctccgcggc   1080

catgaaacag atcggctggc ggcgctggtg acagagatca acaggctcgg cggcgacgcc   1140

gaggagaccg ccgacggcct ggtgatcagg ccggcggagc tacatgctgg agtggtgcac   1200

agctatgctg atcacaggat ggccaccgcc ggcgccatcc tcggcctcgc cgtcagagga   1260

gtggaggtgc aagatatagc aacaacaagc aagaccatgc cggacttccc caagctctgg   1320

gccgacatgc tgggccgcca aacagatgct gccaccaaca ccgccggcac caacaccgcc   1380

ggcaccgccg gcggcaccca gcac                                           1404
```

<210> SEQ ID NO 13
<211> LENGTH: 1392
<212> TYPE: DNA
<213> ORGANISM: Unknown
<220> FEATURE:
<223> OTHER INFORMATION: isolated from soil
<220> FEATURE:
<221> NAME/KEY: CDS
<222> LOCATION: (1)...(1392)

<400> SEQUENCE: 13

```
atg ggc gcg tcc gct gac aac tcc ggc gct gct ccg cac tgg ccc gcg       48
Met Gly Ala Ser Ala Asp Asn Ser Gly Ala Ala Pro His Trp Pro Ala
1               5                   10                  15

ccg ttt gcg gag cag ccc gtt gac gcc acg gtc cgc gtg ccg ggc tcc       96
Pro Phe Ala Glu Gln Pro Val Asp Ala Thr Val Arg Val Pro Gly Ser
            20                  25                  30

aag tcg ctg acc aac agg tac ctg gtg ctc gcc gcg ctg gcc gac ggg      144
Lys Ser Leu Thr Asn Arg Tyr Leu Val Leu Ala Ala Leu Ala Asp Gly
        35                  40                  45

ccg tcc cgg ctc cgg gcg ccg ctg cat tcc cgc gac tca gcg ctg atg      192
Pro Ser Arg Leu Arg Ala Pro Leu His Ser Arg Asp Ser Ala Leu Met
    50                  55                  60

atc gcc gcc ctg cgc cag ctc ggc gcg gac atc cgg gag gtg ccg ggc      240
Ile Ala Ala Leu Arg Gln Leu Gly Ala Asp Ile Arg Glu Val Pro Gly
65                  70                  75                  80

gac ggc gcc ttc ggc ccg gac ctg gag gtg acg ccg att ccg gca aac      288
Asp Gly Ala Phe Gly Pro Asp Leu Glu Val Thr Pro Ile Pro Ala Asn
                85                  90                  95

gcc ggg ggt gcc gac gtc gcc atc gac tgc ggc ctg gcc ggg acc gtc      336
Ala Gly Gly Ala Asp Val Ala Ile Asp Cys Gly Leu Ala Gly Thr Val
            100                 105                 110

atg agg ttt gtt ccg ccg ctg gcg gcg ctc cgc agc ggt acc acc gtt      384
Met Arg Phe Val Pro Pro Leu Ala Ala Leu Arg Ser Gly Thr Thr Val
        115                 120                 125

ttc gac ggc gat ccc cac gcc cgg gag cgc ccg atg ggg acc atc atc      432
Phe Asp Gly Asp Pro His Ala Arg Glu Arg Pro Met Gly Thr Ile Ile
    130                 135                 140

gag gcg ctt gcg ggc ctt ggc gtt acc gtc agc ggc gag gac ggc gga      480
Glu Ala Leu Ala Gly Leu Gly Val Thr Val Ser Gly Glu Asp Gly Gly
145                 150                 155                 160

acg cct gct tca ctg ccg ttc cgc gtc gaa ggc acc ggg cag gtc cgc      528
Thr Pro Ala Ser Leu Pro Phe Arg Val Glu Gly Thr Gly Gln Val Arg
                165                 170                 175

ggc ggg cac ctc gtc ata gac gcc agc gcc tcc tcc cag ttc gtc tcc      576
Gly Gly His Leu Val Ile Asp Ala Ser Ala Ser Ser Gln Phe Val Ser
            180                 185                 190
```

```
gcg ctg ctg ctg gtg ggg gcc cgg ttc acg gac ggc ctg cat ctg gag      624
Ala Leu Leu Leu Val Gly Ala Arg Phe Thr Asp Gly Leu His Leu Glu
        195                 200                 205

cac tcc ggc agc acc gtg ccg agc ctg gac cac atc aac atg acc atc      672
His Ser Gly Ser Thr Val Pro Ser Leu Asp His Ile Asn Met Thr Ile
    210                 215                 220

gct acg ctg cgc ggc gcg ggc gtg gcg gtg gat gac tcc acg ccc aac      720
Ala Thr Leu Arg Gly Ala Gly Val Ala Val Asp Asp Ser Thr Pro Asn
225                 230                 235                 240

cac tgg att gtg ggc ccc ggg ccg atc cgc gcc ttc gac cag cgg atc      768
His Trp Ile Val Gly Pro Gly Pro Ile Arg Ala Phe Asp Gln Arg Ile
                245                 250                 255

gag cag gac ctg tcc aac gcc ggc ccg ttc ctg gcg gcc gcg ctg gca      816
Glu Gln Asp Leu Ser Asn Ala Gly Pro Phe Leu Ala Ala Ala Leu Ala
            260                 265                 270

acc ggc ggc acg gtg cgg att ccg gac tgg ccg gag cac acc acg cag      864
Thr Gly Gly Thr Val Arg Ile Pro Asp Trp Pro Glu His Thr Thr Gln
        275                 280                 285

gtg ggt gac atg tgg cgc agt atc ctc agt gac atg ggg gca acc gtc      912
Val Gly Asp Met Trp Arg Ser Ile Leu Ser Asp Met Gly Ala Thr Val
    290                 295                 300

acc ctg cag gac ggc acc ctg acc gtg acc ggc ggc agc aaa atc aac      960
Thr Leu Gln Asp Gly Thr Leu Thr Val Thr Gly Gly Ser Lys Ile Asn
305                 310                 315                 320

ggc gcg gac ttc gcc gag acc agc gaa ctg gcg ccc acc gtc gct gcg     1008
Gly Ala Asp Phe Ala Glu Thr Ser Glu Leu Ala Pro Thr Val Ala Ala
                325                 330                 335

ctc tgc gcg ctg gca tcc ggt ccc tcg cgg ctg acc ggc atc gcc cac     1056
Leu Cys Ala Leu Ala Ser Gly Pro Ser Arg Leu Thr Gly Ile Ala His
            340                 345                 350

ctc cgg gga cat gag acg gac cgg ctc gcc gcg ctc gtc acc gaa atc     1104
Leu Arg Gly His Glu Thr Asp Arg Leu Ala Ala Leu Val Thr Glu Ile
        355                 360                 365

aac cgc ctc ggc ggc gat gcc gag gaa acc gcc gac gga ctc gtc atc     1152
Asn Arg Leu Gly Gly Asp Ala Glu Glu Thr Ala Asp Gly Leu Val Ile
    370                 375                 380

cgc ccc gcg gaa ctg cac gcg ggg gtg gtg cac agc tac gcg gac cac     1200
Arg Pro Ala Glu Leu His Ala Gly Val Val His Ser Tyr Ala Asp His
385                 390                 395                 400

cgg atg gcc aca gcc gga gcc atc ctc ggc ctg gcg gtc agg ggc gtg     1248
Arg Met Ala Thr Ala Gly Ala Ile Leu Gly Leu Ala Val Arg Gly Val
                405                 410                 415

gaa gtg cag gac atc gcc acc aca tcc aag acc atg ccg gac ttc ccc     1296
Glu Val Gln Asp Ile Ala Thr Thr Ser Lys Thr Met Pro Asp Phe Pro
            420                 425                 430

aag ctg tgg gcg gac atg ctc ggc cgg cag acc gat gca gct aca aac     1344
Lys Leu Trp Ala Asp Met Leu Gly Arg Gln Thr Asp Ala Ala Thr Asn
        435                 440                 445

aca gcg ggt acc aac acc gcg ggg acc gcc ggt ggc acg cag cac tga     1392
Thr Ala Gly Thr Asn Thr Ala Gly Thr Ala Gly Gly Thr Gln His  *
    450                 455                 460


<210> SEQ ID NO 14
<211> LENGTH: 463
<212> TYPE: PRT
<213> ORGANISM: Unknown
<220> FEATURE:
<223> OTHER INFORMATION: isolated from soil

<400> SEQUENCE: 14

Met Gly Ala Ser Ala Asp Asn Ser Gly Ala Ala Pro His Trp Pro Ala
1               5                   10                  15
```

-continued

```
Pro Phe Ala Glu Gln Pro Val Asp Ala Thr Val Arg Val Pro Gly Ser
            20                  25                  30

Lys Ser Leu Thr Asn Arg Tyr Leu Val Leu Ala Ala Leu Ala Asp Gly
        35                  40                  45

Pro Ser Arg Leu Arg Ala Pro Leu His Ser Arg Asp Ser Ala Leu Met
    50                  55                  60

Ile Ala Ala Leu Arg Gln Leu Gly Ala Asp Ile Arg Glu Val Pro Gly
65                  70                  75                  80

Asp Gly Ala Phe Gly Pro Asp Leu Glu Val Thr Pro Ile Pro Ala Asn
                85                  90                  95

Ala Gly Gly Ala Asp Val Ala Ile Asp Cys Gly Leu Ala Gly Thr Val
            100                 105                 110

Met Arg Phe Val Pro Pro Leu Ala Ala Leu Arg Ser Gly Thr Thr Val
        115                 120                 125

Phe Asp Gly Asp Pro His Ala Arg Glu Arg Pro Met Gly Thr Ile Ile
    130                 135                 140

Glu Ala Leu Ala Gly Leu Gly Val Thr Val Ser Gly Glu Asp Gly Gly
145                 150                 155                 160

Thr Pro Ala Ser Leu Pro Phe Arg Val Glu Gly Thr Gly Gln Val Arg
                165                 170                 175

Gly Gly His Leu Val Ile Asp Ala Ser Ala Ser Ser Gln Phe Val Ser
            180                 185                 190

Ala Leu Leu Leu Val Gly Ala Arg Phe Thr Asp Gly Leu His Leu Glu
        195                 200                 205

His Ser Gly Ser Thr Val Pro Ser Leu Asp His Ile Asn Met Thr Ile
    210                 215                 220

Ala Thr Leu Arg Gly Ala Gly Val Ala Val Asp Asp Ser Thr Pro Asn
225                 230                 235                 240

His Trp Ile Val Gly Pro Gly Pro Ile Arg Ala Phe Asp Gln Arg Ile
                245                 250                 255

Glu Gln Asp Leu Ser Asn Ala Gly Pro Phe Leu Ala Ala Ala Leu Ala
            260                 265                 270

Thr Gly Gly Thr Val Arg Ile Pro Asp Trp Pro Glu His Thr Thr Gln
        275                 280                 285

Val Gly Asp Met Trp Arg Ser Ile Leu Ser Asp Met Gly Ala Thr Val
    290                 295                 300

Thr Leu Gln Asp Gly Thr Leu Thr Val Thr Gly Gly Ser Lys Ile Asn
305                 310                 315                 320

Gly Ala Asp Phe Ala Glu Thr Ser Glu Leu Ala Pro Thr Val Ala Ala
                325                 330                 335

Leu Cys Ala Leu Ala Ser Gly Pro Ser Arg Leu Thr Gly Ile Ala His
            340                 345                 350

Leu Arg Gly His Glu Thr Asp Arg Leu Ala Ala Leu Val Thr Glu Ile
        355                 360                 365

Asn Arg Leu Gly Gly Asp Ala Glu Glu Thr Ala Asp Gly Leu Val Ile
    370                 375                 380

Arg Pro Ala Glu Leu His Ala Gly Val Val His Ser Tyr Ala Asp His
385                 390                 395                 400

Arg Met Ala Thr Ala Gly Ala Ile Leu Gly Leu Ala Val Arg Gly Val
                405                 410                 415

Glu Val Gln Asp Ile Ala Thr Thr Ser Lys Thr Met Pro Asp Phe Pro
            420                 425                 430

Lys Leu Trp Ala Asp Met Leu Gly Arg Gln Thr Asp Ala Ala Thr Asn
```

```
        435                 440                 445

Thr Ala Gly Thr Asn Thr Ala Gly Thr Ala Gly Gly Thr Gln His
    450                 455                 460


<210> SEQ ID NO 15
<211> LENGTH: 1239
<212> TYPE: DNA
<213> ORGANISM: Unknown
<220> FEATURE:
<223> OTHER INFORMATION: isolated from soil
<220> FEATURE:
<221> NAME/KEY: CDS
<222> LOCATION: (1)...(1239)

<400> SEQUENCE: 15

gtg acc gtt aca ccg ccc aat ttc ccc ctc aat ggc aag gtc gcg ccc       48
Val Thr Val Thr Pro Pro Asn Phe Pro Leu Asn Gly Lys Val Ala Pro
1               5                   10                  15

ccc ggc tcc aaa tcc att acc aac cgc gcc ctg ttg ctg gcg gcc ctg       96
Pro Gly Ser Lys Ser Ile Thr Asn Arg Ala Leu Leu Leu Ala Ala Leu
            20                  25                  30

gcc aag ggc acc agc cgt ctc agc ggc gcg ctc aag agc gac gac acc      144
Ala Lys Gly Thr Ser Arg Leu Ser Gly Ala Leu Lys Ser Asp Asp Thr
        35                  40                  45

cgc cat atg tcg gtg gcc ctg cgc caa atg ggc gtg acc atc gat gag      192
Arg His Met Ser Val Ala Leu Arg Gln Met Gly Val Thr Ile Asp Glu
    50                  55                  60

ccg gac gac acc acc ttc gtt gtc acc ggc aac ggc aaa ctg cac ctg      240
Pro Asp Asp Thr Thr Phe Val Val Thr Gly Asn Gly Lys Leu His Leu
65                  70                  75                  80

ccg tcg caa ccg ctg ttc ctc ggc aat gcc ggt act gcc atg cgc ttt      288
Pro Ser Gln Pro Leu Phe Leu Gly Asn Ala Gly Thr Ala Met Arg Phe
                85                  90                  95

ctc acg gct gcg gtg gcc acg gtc gaa ggc acc gtg gtg ctg acc ggc      336
Leu Thr Ala Ala Val Ala Thr Val Glu Gly Thr Val Val Leu Thr Gly
            100                 105                 110

gac gac tac atg caa aaa cgc ccg atc ggc ccg ttg ctg gcg acc ctc      384
Asp Asp Tyr Met Gln Lys Arg Pro Ile Gly Pro Leu Leu Ala Thr Leu
        115                 120                 125

ggc cag aac ggc atc cag gtc gac agc ccg acc ggt tgc ccg ccg gtc      432
Gly Gln Asn Gly Ile Gln Val Asp Ser Pro Thr Gly Cys Pro Pro Val
    130                 135                 140

acc gtg cat ggc gtg ggc aag atc aag gcc aag cgc ttc gag atc gac      480
Thr Val His Gly Val Gly Lys Ile Lys Ala Lys Arg Phe Glu Ile Asp
145                 150                 155                 160

ggc ggc ctg tcc agc cag tac gtg tcg gcg ctg ctg atg ctc gcg gcc      528
Gly Gly Leu Ser Ser Gln Tyr Val Ser Ala Leu Leu Met Leu Ala Ala
                165                 170                 175

tgc ggc gaa gcg ccg att gaa gtg gcg ctg acc ggc aag gac atc ggt      576
Cys Gly Glu Ala Pro Ile Glu Val Ala Leu Thr Gly Lys Asp Ile Gly
            180                 185                 190

gcc cgt ggc tat gtc gac ctg acc ctg gac tgc atg cgc gcc ttc ggt      624
Ala Arg Gly Tyr Val Asp Leu Thr Leu Asp Cys Met Arg Ala Phe Gly
        195                 200                 205

gcc cag gtt gaa gcc gtt gac gac acc acc tgg tgc gtg gcc ccg acc      672
Ala Gln Val Glu Ala Val Asp Asp Thr Thr Trp Cys Val Ala Pro Thr
    210                 215                 220

ggc tac atc gcc cac gac tac ctg atc gaa ccc gac gcc tcc gcc gcc      720
Gly Tyr Ile Ala His Asp Tyr Leu Ile Glu Pro Asp Ala Ser Ala Ala
225                 230                 235                 240

act tac ctg tgg gcc gct gaa gtg ttg acc ggg ggg cgc atc gac atc      768
Thr Tyr Leu Trp Ala Ala Glu Val Leu Thr Gly Gly Arg Ile Asp Ile
```

```
                245                 250                 255

ggc gtg gcc gcg cag gat ttc acc cag ccg gac gcc aag gcc cag gcc      816
Gly Val Ala Ala Gln Asp Phe Thr Gln Pro Asp Ala Lys Ala Gln Ala
            260                 265                 270

gtg atc gcg cag ttc ccg cat atg caa gcc acg gtg gtc ggc tcg cag      864
Val Ile Ala Gln Phe Pro His Met Gln Ala Thr Val Val Gly Ser Gln
        275                 280                 285

atg cag gac gcc atc ccg acc ctg gcg gtg ctc gcg gct ttc aac aac      912
Met Gln Asp Ala Ile Pro Thr Leu Ala Val Leu Ala Ala Phe Asn Asn
    290                 295                 300

acg ccg gtg cgt ttc acc gag ttg gcc aac ctg cgg gtc aag gag tgc      960
Thr Pro Val Arg Phe Thr Glu Leu Ala Asn Leu Arg Val Lys Glu Cys
305                 310                 315                 320

gac cgt gtg cag gca ctg cat gac ggc ctc aat gca atc cgc ccg ggc     1008
Asp Arg Val Gln Ala Leu His Asp Gly Leu Asn Ala Ile Arg Pro Gly
                325                 330                 335

ctg gcg acc atc gaa ggc gac gac ctg ctg gta gcc agc gac ccc gca     1056
Leu Ala Thr Ile Glu Gly Asp Asp Leu Leu Val Ala Ser Asp Pro Ala
            340                 345                 350

ttg gcc ggc acc gcg tgc acc gcg ctg atc gac acc cac gcc gac cac     1104
Leu Ala Gly Thr Ala Cys Thr Ala Leu Ile Asp Thr His Ala Asp His
        355                 360                 365

cgc atc gcc atg tgc ttt gcc ctg gcc ggg ctg aag gtt tcg ggt att     1152
Arg Ile Ala Met Cys Phe Ala Leu Ala Gly Leu Lys Val Ser Gly Ile
    370                 375                 380

cgc atc cag gac ccg gat tgc gtg gca aag acc tat ccc gag tac tgg     1200
Arg Ile Gln Asp Pro Asp Cys Val Ala Lys Thr Tyr Pro Glu Tyr Trp
385                 390                 395                 400

aag gcc ctg ggc agt ctc ggg gtg cag ctg agc tat taa                 1239
Lys Ala Leu Gly Ser Leu Gly Val Gln Leu Ser Tyr  *
                405                 410


<210> SEQ ID NO 16
<211> LENGTH: 412
<212> TYPE: PRT
<213> ORGANISM: Unknown
<220> FEATURE:
<223> OTHER INFORMATION: isolated from soil

<400> SEQUENCE: 16

Val Thr Val Thr Pro Pro Asn Phe Pro Leu Asn Gly Lys Val Ala Pro
1               5                   10                  15

Pro Gly Ser Lys Ser Ile Thr Asn Arg Ala Leu Leu Leu Ala Ala Leu
            20                  25                  30

Ala Lys Gly Thr Ser Arg Leu Ser Gly Ala Leu Lys Ser Asp Asp Thr
        35                  40                  45

Arg His Met Ser Val Ala Leu Arg Gln Met Gly Val Thr Ile Asp Glu
    50                  55                  60

Pro Asp Asp Thr Thr Phe Val Val Thr Gly Asn Gly Lys Leu His Leu
65                  70                  75                  80

Pro Ser Gln Pro Leu Phe Leu Gly Asn Ala Gly Thr Ala Met Arg Phe
                85                  90                  95

Leu Thr Ala Ala Val Ala Thr Val Glu Gly Thr Val Val Leu Thr Gly
            100                 105                 110

Asp Asp Tyr Met Gln Lys Arg Pro Ile Gly Pro Leu Leu Ala Thr Leu
        115                 120                 125

Gly Gln Asn Gly Ile Gln Val Asp Ser Pro Thr Gly Cys Pro Pro Val
    130                 135                 140

Thr Val His Gly Val Gly Lys Ile Lys Ala Lys Arg Phe Glu Ile Asp
```

-continued

```
145                 150                 155                 160

Gly Gly Leu Ser Ser Gln Tyr Val Ser Ala Leu Leu Met Leu Ala Ala
                165                 170                 175

Cys Gly Glu Ala Pro Ile Glu Val Ala Leu Thr Gly Lys Asp Ile Gly
            180                 185                 190

Ala Arg Gly Tyr Val Asp Leu Thr Leu Asp Cys Met Arg Ala Phe Gly
        195                 200                 205

Ala Gln Val Glu Ala Val Asp Asp Thr Thr Trp Cys Val Ala Pro Thr
    210                 215                 220

Gly Tyr Ile Ala His Asp Tyr Leu Ile Glu Pro Asp Ala Ser Ala Ala
225                 230                 235                 240

Thr Tyr Leu Trp Ala Ala Glu Val Leu Thr Gly Gly Arg Ile Asp Ile
                245                 250                 255

Gly Val Ala Ala Gln Asp Phe Thr Gln Pro Asp Ala Lys Ala Gln Ala
            260                 265                 270

Val Ile Ala Gln Phe Pro His Met Gln Ala Thr Val Val Gly Ser Gln
        275                 280                 285

Met Gln Asp Ala Ile Pro Thr Leu Ala Val Leu Ala Ala Phe Asn Asn
    290                 295                 300

Thr Pro Val Arg Phe Thr Glu Leu Ala Asn Leu Arg Val Lys Glu Cys
305                 310                 315                 320

Asp Arg Val Gln Ala Leu His Asp Gly Leu Asn Ala Ile Arg Pro Gly
                325                 330                 335

Leu Ala Thr Ile Glu Gly Asp Asp Leu Leu Val Ala Ser Asp Pro Ala
            340                 345                 350

Leu Ala Gly Thr Ala Cys Thr Ala Leu Ile Asp Thr His Ala Asp His
        355                 360                 365

Arg Ile Ala Met Cys Phe Ala Leu Ala Gly Leu Lys Val Ser Gly Ile
    370                 375                 380

Arg Ile Gln Asp Pro Asp Cys Val Ala Lys Thr Tyr Pro Glu Tyr Trp
385                 390                 395                 400

Lys Ala Leu Gly Ser Leu Gly Val Gln Leu Ser Tyr
                405                 410
```

<210> SEQ ID NO 17
<211> LENGTH: 1236
<212> TYPE: DNA
<213> ORGANISM: Artificial Sequence
<220> FEATURE:
<223> OTHER INFORMATION: synthetic nucleotide sequence encoding GRG38 (syngrg38)

<400> SEQUENCE: 17

```
atgacggtga cgccgccaaa cttcccgctc aatggcaagg tggcgccgcc gggcagcaag     60

agcatcacca acagggcgct gctgctggcg gcgctggcca agggcacctc aaggctgagc    120

ggcgcgctga agagcgacga cacccgtcac atgagcgtgg cgctgcggca gatgggcgtc    180

accattgatg aacctgatga caccaccttc gtcgtcaccg gcaatggcaa gctgcatctt    240

ccatcacagc cgctcttcct cggcaacgcc ggcaccgcca tgaggttctt gacggcggcg    300

gtggccaccg tggaaggaac agtggtgctc actggagatg actacatgca aaagaggcca    360

attggacctc tactggcgac gctgggccaa aatggcatcc aggtggactc gccgacgggc    420

tgcccgccgg tgacagttca tggcgtcggc aagatcaagg ccaagagatt tgagatcgac    480

ggcggcctca gcagccaata tgtttcagcg ctgctgatgc tggcggcctg cggcgaggcg    540

cccatcgagg tggcgctcac cggcaaggac atcggcgcgc gcggctatgt ggacctcacc    600
```

```
ttggactgca tgagggcctt cggcgctcaa gtggaggcgg tggatgacac cacctggtgc    660

gtggcgccga cgggctacat tgctcatgac tacctcatcg agccagatgc ctccgccgcc    720

acctacctat gggcggcgga ggtgctcacc ggcggcagga tcgacatcgg cgtcgccgct    780

caagatttca cccaacctga tgccaaggct caagctgtga ttgctcaatt tcctcacatg    840

caagcaacag tggtgggcag ccagatgcaa gatgccatcc cgacgctggc ggtgctggcg    900

gccttcaaca acacgccggt gaggttcacc gagctggcca acctacgagt gaaggaatgt    960

gacagggtgc aagctcttca tgatggcctc aacgccatca ggccagggct ggccaccatt   1020

gaaggagatg atctgctggt ggcttcagat ccggcgctcg ccggcaccgc ctgcacggcg   1080

ctcatcgaca cccacgccga ccaccgcatc gccatgtgct tcgcgctcgc cggcctcaag   1140

gtgagcggca tcaggattca agatccagat tgtgtggcca agacctaccc ggagtactgg   1200

aaggcgctgg gcagcctcgg cgtgcagctg agctac                              1236
```

```
<210> SEQ ID NO 18
<211> LENGTH: 1296
<212> TYPE: DNA
<213> ORGANISM: Unknown
<220> FEATURE:
<223> OTHER INFORMATION: isolated from soil
<220> FEATURE:
<221> NAME/KEY: CDS
<222> LOCATION: (1)...(1296)

<400> SEQUENCE: 18

atg gac gtt atc gtt aaa cca acc cca tcc ctg aac ggg gaa att gga       48
Met Asp Val Ile Val Lys Pro Thr Pro Ser Leu Asn Gly Glu Ile Gly
1               5                   10                  15

gct ttg tct tcc aaa aac tac acc aca cgc tac ttg cta gct gct gcg       96
Ala Leu Ser Ser Lys Asn Tyr Thr Thr Arg Tyr Leu Leu Ala Ala Ala
            20                  25                  30

ctg gca gaa ggc aca agt aca atc cat tac ccg gct cat agt gaa gat      144
Leu Ala Glu Gly Thr Ser Thr Ile His Tyr Pro Ala His Ser Glu Asp
        35                  40                  45

agt gat gct atg cgc aga tgt att cgt gac ctt ggg gcg gtg ctt gaa      192
Ser Asp Ala Met Arg Arg Cys Ile Arg Asp Leu Gly Ala Val Leu Glu
    50                  55                  60

gaa gat gat agc aaa atc gtt atc caa gga ttc ggc agc cat ccg cgt      240
Glu Asp Asp Ser Lys Ile Val Ile Gln Gly Phe Gly Ser His Pro Arg
65                  70                  75                  80

gat gtg cgt gaa tta aat gta ggc aat gcg ggt gca gtg ctg cgt ttc      288
Asp Val Arg Glu Leu Asn Val Gly Asn Ala Gly Ala Val Leu Arg Phe
                85                  90                  95

ctg atg gga gta acg gca ctt tgt cca gag gtg acg ttt gta aat acg      336
Leu Met Gly Val Thr Ala Leu Cys Pro Glu Val Thr Phe Val Asn Thr
            100                 105                 110

tac ccg gat tct ctt ggc aaa cgc cca cat gat gac ctg atc gat gcg      384
Tyr Pro Asp Ser Leu Gly Lys Arg Pro His Asp Asp Leu Ile Asp Ala
        115                 120                 125

ctt ggt cag ctc ggt gtt gag gta cag cac gaa caa gga cgc ttg cca      432
Leu Gly Gln Leu Gly Val Glu Val Gln His Glu Gln Gly Arg Leu Pro
    130                 135                 140

atc acg atc aaa ggg ggt cag gct aag ggt gga cat atc cgt gta tcc      480
Ile Thr Ile Lys Gly Gly Gln Ala Lys Gly Gly His Ile Arg Val Ser
145                 150                 155                 160

ggt tct gtc agc tcc cag tat ttg agc gcg ttg ctg ttt gta act cct      528
Gly Ser Val Ser Ser Gln Tyr Leu Ser Ala Leu Leu Phe Val Thr Pro
                165                 170                 175
```

-continued

```
ctt ctg gcc gaa gac agc aca att gaa gta tta aac gac ttg aaa tcc      576
Leu Leu Ala Glu Asp Ser Thr Ile Glu Val Leu Asn Asp Leu Lys Ser
            180                 185                 190

aaa gtg gtt att ggt cag acg ctg gaa gta ctg gaa cag gcg ggg att      624
Lys Val Val Ile Gly Gln Thr Leu Glu Val Leu Glu Gln Ala Gly Ile
        195                 200                 205

gtc att cat gcg agt gat gat tac atg tcc ttc cgt gta cct ggt ggt      672
Val Ile His Ala Ser Asp Asp Tyr Met Ser Phe Arg Val Pro Gly Gly
    210                 215                 220

caa gct tat aaa ccg caa aca tat acc gtt caa ggc gac tat cca gga      720
Gln Ala Tyr Lys Pro Gln Thr Tyr Thr Val Gln Gly Asp Tyr Pro Gly
225                 230                 235                 240

tca gca gct gtc ctc gcg gcc gcg gct gtc acc caa tca gat gtt aaa      768
Ser Ala Ala Val Leu Ala Ala Ala Ala Val Thr Gln Ser Asp Val Lys
                245                 250                 255

att ttg cga ttg atg gaa cag agc aaa cag ggt gag cgt gct att gtt      816
Ile Leu Arg Leu Met Glu Gln Ser Lys Gln Gly Glu Arg Ala Ile Val
            260                 265                 270

gac gtt ctg cgt atg atg gaa gtg cca ttg acg cat gag aac gat gtg      864
Asp Val Leu Arg Met Met Glu Val Pro Leu Thr His Glu Asn Asp Val
        275                 280                 285

gta cac gtg caa ggt aac ggt aca ttg aaa gcc gtg gaa ttc gac gga      912
Val His Val Gln Gly Asn Gly Thr Leu Lys Ala Val Glu Phe Asp Gly
    290                 295                 300

gat gcc gcg aca gac gcg gtt ttg gcc atg gta gcg gcg gca gtg ttt      960
Asp Ala Ala Thr Asp Ala Val Leu Ala Met Val Ala Ala Ala Val Phe
305                 310                 315                 320

gcg gaa ggc acc tca cgg ttc tat aat gta gag aac tta cgt tac aag     1008
Ala Glu Gly Thr Ser Arg Phe Tyr Asn Val Glu Asn Leu Arg Tyr Lys
                325                 330                 335

gaa tgt gac cga att acg gat tat ttg aac gaa ctg cgg aag gca gga     1056
Glu Cys Asp Arg Ile Thr Asp Tyr Leu Asn Glu Leu Arg Lys Ala Gly
            340                 345                 350

gcc aac gta gaa gaa cgt cag gcc gag att atc gta cat ggt cgt ccg     1104
Ala Asn Val Glu Glu Arg Gln Ala Glu Ile Ile Val His Gly Arg Pro
        355                 360                 365

gaa ggc gtc gaa ggc ggc gtt gag att aac gct cac tac gat cat cgc     1152
Glu Gly Val Glu Gly Gly Val Glu Ile Asn Ala His Tyr Asp His Arg
    370                 375                 380

gta att atg gca ctg acc gtt gtt ggt ttg cgt tcc aaa gaa ccg ctt     1200
Val Ile Met Ala Leu Thr Val Val Gly Leu Arg Ser Lys Glu Pro Leu
385                 390                 395                 400

cgt att cgg gat gca cac cat gta gcg aag tct tat cca caa tat ttc     1248
Arg Ile Arg Asp Ala His His Val Ala Lys Ser Tyr Pro Gln Tyr Phe
                405                 410                 415

gat cat ttg cag gcg ctt ggc gcc tcg gtt caa tgg gta aaa gag taa     1296
Asp His Leu Gln Ala Leu Gly Ala Ser Val Gln Trp Val Lys Glu  *
            420                 425                 430


<210> SEQ ID NO 19
<211> LENGTH: 431
<212> TYPE: PRT
<213> ORGANISM: Unknown
<220> FEATURE:
<223> OTHER INFORMATION: isolated from soil

<400> SEQUENCE: 19

Met Asp Val Ile Val Lys Pro Thr Pro Ser Leu Asn Gly Glu Ile Gly
1               5                   10                  15

Ala Leu Ser Ser Lys Asn Tyr Thr Thr Arg Tyr Leu Leu Ala Ala Ala
            20                  25                  30
```

-continued

```
Leu Ala Glu Gly Thr Ser Thr Ile His Tyr Pro Ala His Ser Glu Asp
        35                  40                  45

Ser Asp Ala Met Arg Arg Cys Ile Arg Asp Leu Gly Ala Val Leu Glu
    50                  55                  60

Glu Asp Asp Ser Lys Ile Val Ile Gln Gly Phe Gly Ser His Pro Arg
65                  70                  75                  80

Asp Val Arg Glu Leu Asn Val Gly Asn Ala Gly Ala Val Leu Arg Phe
                85                  90                  95

Leu Met Gly Val Thr Ala Leu Cys Pro Glu Val Thr Phe Val Asn Thr
            100                 105                 110

Tyr Pro Asp Ser Leu Gly Lys Arg Pro His Asp Asp Leu Ile Asp Ala
        115                 120                 125

Leu Gly Gln Leu Gly Val Glu Val Gln His Glu Gln Gly Arg Leu Pro
    130                 135                 140

Ile Thr Ile Lys Gly Gly Gln Ala Lys Gly Gly His Ile Arg Val Ser
145                 150                 155                 160

Gly Ser Val Ser Ser Gln Tyr Leu Ser Ala Leu Leu Phe Val Thr Pro
                165                 170                 175

Leu Leu Ala Glu Asp Ser Thr Ile Glu Val Leu Asn Asp Leu Lys Ser
            180                 185                 190

Lys Val Val Ile Gly Gln Thr Leu Glu Val Leu Glu Gln Ala Gly Ile
        195                 200                 205

Val Ile His Ala Ser Asp Asp Tyr Met Ser Phe Arg Val Pro Gly Gly
    210                 215                 220

Gln Ala Tyr Lys Pro Gln Thr Tyr Thr Val Gln Gly Asp Tyr Pro Gly
225                 230                 235                 240

Ser Ala Ala Val Leu Ala Ala Ala Ala Val Thr Gln Ser Asp Val Lys
                245                 250                 255

Ile Leu Arg Leu Met Glu Gln Ser Lys Gln Gly Glu Arg Ala Ile Val
            260                 265                 270

Asp Val Leu Arg Met Met Glu Val Pro Leu Thr His Glu Asn Asp Val
        275                 280                 285

Val His Val Gln Gly Asn Gly Thr Leu Lys Ala Val Glu Phe Asp Gly
    290                 295                 300

Asp Ala Ala Thr Asp Ala Val Leu Ala Met Val Ala Ala Ala Val Phe
305                 310                 315                 320

Ala Glu Gly Thr Ser Arg Phe Tyr Asn Val Glu Asn Leu Arg Tyr Lys
                325                 330                 335

Glu Cys Asp Arg Ile Thr Asp Tyr Leu Asn Glu Leu Arg Lys Ala Gly
            340                 345                 350

Ala Asn Val Glu Glu Arg Gln Ala Glu Ile Ile Val His Gly Arg Pro
        355                 360                 365

Glu Gly Val Glu Gly Gly Val Glu Ile Asn Ala His Tyr Asp His Arg
    370                 375                 380

Val Ile Met Ala Leu Thr Val Val Gly Leu Arg Ser Lys Glu Pro Leu
385                 390                 395                 400

Arg Ile Arg Asp Ala His His Val Ala Lys Ser Tyr Pro Gln Tyr Phe
                405                 410                 415

Asp His Leu Gln Ala Leu Gly Ala Ser Val Gln Trp Val Lys Glu
            420                 425                 430
```

<210> SEQ ID NO 20
<211> LENGTH: 1293
<212> TYPE: DNA
<213> ORGANISM: Artificial Sequence
<220> FEATURE:
<223> OTHER INFORMATION: synthetic nucleotide sequence encoding GRG39
(syngrg39)

<400> SEQUENCE: 20

```
atggatgtca tcgtcaagcc gacgccaagc ctcaatggag agatcggcgc gctgagcagc     60

aagaactaca caacaagata tttgctggcg gcggcgctgg cagaaggaac aagcaccatc    120

cactaccctg ctcattcaga agattctgat gccatgagaa gatgcatcag ggacctcggc    180

gccgtgctgg aagaagatga cagcaagatc gtcatccaag gcttcggctc acatccaaga    240

gatgtgaggg agctcaatgt tggaaatgct ggcgccgtgc tgcgcttctt gatgggcgtg    300

acggcgctct gcccggaggt gaccttcgtc aacacctacc ccgacagcct cggcaagagg    360

cctcatgatg acctcatcga cgcgctgggg cagctaggag tggaggtgca gcatgagcaa    420

ggaaggctgc ccatcaccat caagggcggc caagcaaaag gaggccacat cagagtttct    480

ggaagcgtca gctctcagta cctctcggcg ctgctcttcg tgacgccgct gctggcagaa    540

gattccacca tcgaggtgct aaatgacctc aagagcaagg tggtgatcgg ccagacgctg    600

gaggtgctgg agcaagctgg catcgtcatc catgcttcag atgactacat gagcttcaga    660

gttcctggag gacaagccta caagccgcag acctacaccg tccaaggaga ttatcctgga    720

agcgccgccg tgctggccgc cgccgccgtc acccaaagtg atgtgaagat cctccggctg    780

atggagcaat caaagcaagg agaaagggcc atcgtggatg tgctgaggat gatggaggtg    840

ccgctcaccc atgaaaatga tgtggtgcat gttcaaggaa atggcacctt gaaggcggtg    900

gagtttgatg gagatgctgc aacagatgct gtgctggcaa tggtggcggc ggcggtgttt    960

gctgaaggaa catcaagatt ctacaatgtg gagaacttga gatacaagga atgtgacagg   1020

atcaccgact acctcaacga gctgaggaag gccggcgcca atgtggagga gaggcaagct   1080

gagatcattg ttcatggaag gccagaagga gtggagggcg gcgtggagat caatgctcac   1140

tacgaccacc gcgtcatcat ggcgctaaca gtggtggggc tgaggagcaa ggagccgctg   1200

aggatcagag atgctcatca tgtggccaag agctaccctc aatattttga tcatcttcaa   1260

gctctcggcg cctccgtgca gtgggtgaag gag                                1293
```

<210> SEQ ID NO 21
<211> LENGTH: 1260
<212> TYPE: DNA
<213> ORGANISM: Rhizobium leguminosarum
<220> FEATURE:
<221> NAME/KEY: CDS
<222> LOCATION: (1)...(1260)

<400> SEQUENCE: 21

```
atg atg atg ggt aga gcc aaa ctc acg att atc ccg ccg ggc aag cct       48
Met Met Met Gly Arg Ala Lys Leu Thr Ile Ile Pro Pro Gly Lys Pro
1               5                   10                  15

ttg acc gga cgc gcc atg ccg ccg gga tcg aag tcg atc acc aac cgc       96
Leu Thr Gly Arg Ala Met Pro Pro Gly Ser Lys Ser Ile Thr Asn Arg
            20                  25                  30

gcg ctg ctg ctg gca ggc ctt gcc aag ggc acg agc cgg ctg acc ggc      144
Ala Leu Leu Leu Ala Gly Leu Ala Lys Gly Thr Ser Arg Leu Thr Gly
        35                  40                  45

gcg ctg aaa agc gac gat acc cgc tat atg gcc gaa gcg ttg cgc gcc      192
Ala Leu Lys Ser Asp Asp Thr Arg Tyr Met Ala Glu Ala Leu Arg Ala
    50                  55                  60

atg ggc gtt gcg atc gac gag ccc gac gac acc acc ttc atc gtg aca      240
Met Gly Val Ala Ile Asp Glu Pro Asp Asp Thr Thr Phe Ile Val Thr
65                  70                  75                  80
```

-continued

```
ggc agt ggc aag ctg cag gcg ccg gca gcc cct ctt ttc ctc ggc aat      288
Gly Ser Gly Lys Leu Gln Ala Pro Ala Ala Pro Leu Phe Leu Gly Asn
                85                  90                  95

gcc ggc acg gca acg cgc ttc ctg aca gca gca gca gcg cta gtc gaa      336
Ala Gly Thr Ala Thr Arg Phe Leu Thr Ala Ala Ala Ala Leu Val Glu
            100                 105                 110

ggc aag gtc gtc gtt gat ggc gat gcc cat atg cgc aaa cgg ccg atc      384
Gly Lys Val Val Val Asp Gly Asp Ala His Met Arg Lys Arg Pro Ile
        115                 120                 125

ggc ccg ctg gtc gac gcg ctc cgc tcg ctc ggc gtg gac gcc tcg acg      432
Gly Pro Leu Val Asp Ala Leu Arg Ser Leu Gly Val Asp Ala Ser Thr
    130                 135                 140

gaa acc ggc tgc cca ccc gta aca atc aat ggc acc ggc cgt ttc gaa      480
Glu Thr Gly Cys Pro Pro Val Thr Ile Asn Gly Thr Gly Arg Phe Glu
145                 150                 155                 160

gct agc cgc gtg cag atc gac ggc ggc ctg tcc agc cag tat gtc tcg      528
Ala Ser Arg Val Gln Ile Asp Gly Gly Leu Ser Ser Gln Tyr Val Ser
                165                 170                 175

gcg ctg ttg atg atg gcg gcc ggc ggc gac cgc gcc gtc gat atc gag      576
Ala Leu Leu Met Met Ala Ala Gly Gly Asp Arg Ala Val Asp Ile Glu
            180                 185                 190

ctg ctc ggc gaa cat atc ggt gct ctg gga tac atc gac ctg acc gtt      624
Leu Leu Gly Glu His Ile Gly Ala Leu Gly Tyr Ile Asp Leu Thr Val
        195                 200                 205

gcc gcc atg cgc gcc ttc ggt gcc aag gtc gag cgc gtg agc cca gtc      672
Ala Ala Met Arg Ala Phe Gly Ala Lys Val Glu Arg Val Ser Pro Val
    210                 215                 220

gcc tgg cgt gtc gag ccc acc ggc tac cat gct gcc gat ttc ctg atc      720
Ala Trp Arg Val Glu Pro Thr Gly Tyr His Ala Ala Asp Phe Leu Ile
225                 230                 235                 240

gag ccg gat gcc tct gct gcg acc tat ctc tgg gct gcc gaa gtg ctt      768
Glu Pro Asp Ala Ser Ala Ala Thr Tyr Leu Trp Ala Ala Glu Val Leu
                245                 250                 255

ggt ggg ggc aag atc gat ctc ggg acg ccg gcg gaa caa ttc tcg cag      816
Gly Gly Gly Lys Ile Asp Leu Gly Thr Pro Ala Glu Gln Phe Ser Gln
            260                 265                 270

ccg gat gcg aaa gca tat gat ctg atc tcg aaa ttc ccg cat ctg ccc      864
Pro Asp Ala Lys Ala Tyr Asp Leu Ile Ser Lys Phe Pro His Leu Pro
        275                 280                 285

gcc gtc atc gac ggt tcg cag atg cag gac gcc atc ccg acg ctt gcg      912
Ala Val Ile Asp Gly Ser Gln Met Gln Asp Ala Ile Pro Thr Leu Ala
    290                 295                 300

gtt ctc gcc gct ttc aac gag acg ccg gtg cgc ttc gtc ggc atc gag      960
Val Leu Ala Ala Phe Asn Glu Thr Pro Val Arg Phe Val Gly Ile Glu
305                 310                 315                 320

aat ctc cgc gtc aag gaa tgc gat cgt atc cgc gcg ctg tcg agc ggc     1008
Asn Leu Arg Val Lys Glu Cys Asp Arg Ile Arg Ala Leu Ser Ser Gly
                325                 330                 335

ctg tcg cgc gtc gtt ccg aac ctc ggc acg gaa gag ggc gac gat ctg     1056
Leu Ser Arg Val Val Pro Asn Leu Gly Thr Glu Glu Gly Asp Asp Leu
            340                 345                 350

atc gtc gca tcc gat ccg agc ctc gcc ggc aag acc ctg ccc gca gag     1104
Ile Val Ala Ser Asp Pro Ser Leu Ala Gly Lys Thr Leu Pro Ala Glu
        355                 360                 365

atc gac agc ttt gcc gat cat cgc att gcc atg agc ttt gcg ctt gcc     1152
Ile Asp Ser Phe Ala Asp His Arg Ile Ala Met Ser Phe Ala Leu Ala
    370                 375                 380

ggc ctg aag atc ggc ggc atc acc att ctc gac ccc gat tgc gtc gcc     1200
Gly Leu Lys Ile Gly Gly Ile Thr Ile Leu Asp Pro Asp Cys Val Ala
385                 390                 395                 400
```

-continued

```
aag acc ttc ccg tcc tat tgg aac gtg ctg gct tcg ctt gga gtc aca      1248
Lys Thr Phe Pro Ser Tyr Trp Asn Val Leu Ala Ser Leu Gly Val Thr
                405                 410                 415

tac gaa gac tga                                                      1260
Tyr Glu Asp  *


<210> SEQ ID NO 22
<211> LENGTH: 419
<212> TYPE: PRT
<213> ORGANISM: Rhizobium leguminosarum

<400> SEQUENCE: 22

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Ala Ile Asp Glu Pro Asp Asp Thr Thr Phe Ile Val Thr
65                  70                  75                  80

Gly Ser Gly Lys Leu Gln Ala Pro Ala Ala Pro Leu Phe Leu Gly Asn
                85                  90                  95

Ala Gly Thr Ala Thr Arg Phe Leu Thr Ala Ala Ala Ala Leu Val Glu
            100                 105                 110

Gly Lys Val Val Val Asp Gly Asp Ala His Met Arg Lys Arg Pro Ile
        115                 120                 125

Gly Pro Leu Val Asp Ala Leu Arg Ser Leu Gly Val Asp Ala Ser Thr
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Ile Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Val Ser Pro Val
    210                 215                 220

Ala Trp Arg Val Glu Pro Thr Gly Tyr His Ala Ala Asp Phe Leu Ile
225                 230                 235                 240

Glu Pro Asp Ala Ser Ala Ala Thr Tyr Leu Trp Ala Ala Glu Val Leu
                245                 250                 255

Gly Gly Gly Lys Ile Asp Leu Gly Thr Pro Ala Glu Gln Phe Ser Gln
            260                 265                 270

Pro Asp Ala Lys Ala Tyr Asp Leu Ile Ser Lys Phe Pro His Leu Pro
        275                 280                 285

Ala Val Ile Asp Gly Ser Gln Met Gln Asp Ala Ile Pro Thr Leu Ala
    290                 295                 300

Val Leu Ala Ala Phe Asn Glu Thr Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Val Val Pro Asn Leu Gly Thr Glu Glu Gly Asp Asp Leu
```

-continued

```
            340                 345                 350

Ile Val Ala Ser Asp Pro Ser Leu Ala Gly Lys Thr Leu Pro Ala Glu
        355                 360                 365

Ile Asp Ser Phe Ala Asp His Arg Ile Ala Met Ser Phe Ala Leu Ala
    370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ala Ser Leu Gly Val Thr
                405                 410                 415

Tyr Glu Asp


<210> SEQ ID NO 23
<211> LENGTH: 1257
<212> TYPE: DNA
<213> ORGANISM: Artificial Sequence
<220> FEATURE:
<223> OTHER INFORMATION: synthetic nucleotide sequence encoding GRG50
      (syngrg50)

<400> SEQUENCE: 23

atgatgatgg gccgcgccaa gctcaccatc atcccgccgg gcaagccgct caccggccgc     60

gccatgccgc cgggcagcaa gagcatcacc aacagggcgc tgctgctggc cggcctcgcc    120

aagggcacct caaggctcac cggcgcgctg aagagcgacg acacccgcta catggcggag    180

gcgctgagag caatgggcgt cgccatcgac gagccagatg acaccacctt catcgtcacc    240

ggctcaggca agctgcaagc gccggcggcg ccgctcttcc tcggcaacgc cggcacggca    300

acaagattct tgacggcggc ggcggcgctg gtggaaggca aggtggtggt ggatggtgat    360

gctcacatga ggaagaggcc aattgggccg ctggtggacg cgctgaggag cctcggcgtg    420

gatgcttcaa cagaaactgg ctgcccgccg gtgaccatca atggaactgg aagatttgaa    480

gcatcaagag ttcagatcga cggcggcctc agctctcaat atgtctcggc gctgctgatg    540

atggccgccg gcggcgaccg cgccgtggac attgagctgc tgggagagca catcggcgcg    600

ctgggctaca tcgacctcac cgtcgccgcc atgagggcct tcggcgccaa ggtggagagg    660

gtgtcaccag tggcatggag ggtggagcca actggctacc atgctgctga cttcctcatc    720

gagccagatg cttctgctgc cacctacctc tgggcggcgg aggtgctggg cggcggcaag    780

atagatcttg ggacgccggc ggagcagttc agccaacctg atgccaaggc ctacgacctc    840

atctcaaaat ttcctcatct tcccgccgtc atcgacggca gccagatgca agatgccatc    900

ccgacgctgg cggtgctggc ggccttcaat gagacgccgg tgaggttcgt cggcatcgag    960

aacctccgcg tcaaggaatg tgacaggatc agggcgctga gcagcggcct ctcaagggtg   1020

gtgcccaacc tcggcacaga agaaggagat gacctcatcg tggcttcaga tccaagcctc   1080

gccggcaaga cgctgccggc ggagatcgac agctttgctg atcaccgcat cgccatgagc   1140

ttcgcgctcg ccggcctcaa gatcggcggc atcaccatcc ttgatccaga ttgtgtggcc   1200

aagaccttcc caagctactg gaatgtgctg gcaagcctcg gcgtcaccta tgaagat      1257


<210> SEQ ID NO 24
<211> LENGTH: 438
<212> TYPE: PRT
<213> ORGANISM: Streptomyces coelicolor A3(2)

<400> SEQUENCE: 24

Met Thr Val Asn Pro Thr His Thr Ala Leu Trp Pro Ala Pro His Ala
1               5                   10                  15
```

-continued

```
Ser Gly Ala Val Asp Ala Thr Val His Val Pro Gly Ser Lys Ser Val
            20                  25                  30

Thr Asn Arg Ala Leu Val Leu Ala Ala Leu Ala Ser Glu Pro Gly Trp
        35                  40                  45

Leu Arg Arg Pro Leu Arg Ser Arg Asp Thr Leu Leu Met Ala Glu Ala
    50                  55                  60

Leu Arg Thr Leu Gly Val Glu Ile Glu Glu Gly Val Gly Pro Glu Gly
65                  70                  75                  80

Thr Gly Glu Phe Trp Arg Val Ile Pro Ala Gly Leu Arg Gly Pro Ala
                85                  90                  95

Thr Val Asp Val Gly Asn Ala Gly Thr Val Met Arg Phe Leu Pro Pro
            100                 105                 110

Val Ala Thr Leu Ala Asp Gly Ala Val Arg Phe Asp Gly Asp Pro Arg
        115                 120                 125

Ser Tyr Glu Arg Pro Leu His Gly Val Ile Asp Ala Leu Arg Val Leu
    130                 135                 140

Gly Ala Arg Ile Asp Asp Asp Gly Arg Gly Ala Leu Pro Leu Thr Val
145                 150                 155                 160

His Gly Gly Gly Ala Leu Glu Gly Gly Pro Val Glu Ile Asp Ala Ser
                165                 170                 175

Ser Ser Ser Gln Phe Val Ser Ala Leu Leu Leu Ser Gly Pro Arg Phe
            180                 185                 190

Asn Gln Gly Val Glu Val Arg His Thr Gly Ser Ala Leu Pro Ser Met
        195                 200                 205

Pro His Ile Arg Met Thr Val Asp Met Leu Arg Ala Val Gly Ala Gln
    210                 215                 220

Val Asp Thr Pro Glu Ser Gly Gly Glu Pro Asn Val Trp Arg Val Thr
225                 230                 235                 240

Pro Gly Ala Leu Leu Gly Arg Asp Leu Thr Val Glu Pro Asp Leu Ser
                245                 250                 255

Asn Ala Gln Pro Phe Leu Ala Ala Ala Leu Val Thr Gly Gly Lys Val
            260                 265                 270

Val Ile Pro Asp Trp Pro Ser Arg Thr Thr Gln Pro Gly Asp Arg Leu
        275                 280                 285

Arg Glu Ile Phe Thr Asp Met Gly Gly Ser Cys Glu Leu Thr Asp Phe
    290                 295                 300

Gly Leu Val Phe Thr Gly Ser Gly Ala Ile His Gly Ile Asp Val Asp
305                 310                 315                 320

Leu Ser Glu Val Gly Glu Leu Thr Pro Gly Ile Ala Ala Val Ala Ala
                325                 330                 335

Leu Ala Asp Ser Pro Ser Thr Leu Arg Gly Val Ala His Leu Arg Leu
            340                 345                 350

His Glu Thr Asp Arg Leu Ala Ala Leu Thr Lys Glu Ile Asn Glu Leu
        355                 360                 365

Gly Gly Asp Val Thr Glu Thr Ala Asp Gly Leu His Ile Arg Pro Arg
    370                 375                 380

Arg Leu His Gly Gly Val Phe His Thr Tyr Asp Asp His Arg Met Ala
385                 390                 395                 400

Thr Ala Gly Ala Val Leu Gly Leu Ala Val Glu Gly Val Gln Ile Glu
                405                 410                 415

Asn Val Ala Thr Thr Ala Lys Thr Leu Pro Asp Phe Pro Asp Leu Trp
            420                 425                 430

Thr Gly Met Leu Gly Ala
        435
```

<210> SEQ ID NO 25
<211> LENGTH: 446
<212> TYPE: PRT
<213> ORGANISM: Streptomyces avermitilis MA-4680

<400> SEQUENCE: 25

```
Met Thr Val Asn Pro Ala His Thr Ala Leu Trp Pro Ala Pro His Ala
1               5                   10                  15

Ser Gly Ala Val Asp Ala Thr Val His Val Pro Gly Ser Lys Ser Val
            20                  25                  30

Thr Asn Arg Ala Leu Val Leu Ala Ala Leu Ala Ser Glu Pro Gly Trp
        35                  40                  45

Leu Arg Arg Pro Leu Arg Ser Arg Asp Thr Leu Leu Met Ala Ala Ala
    50                  55                  60

Leu Arg Glu Met Gly Val Gly Ile Glu Glu Thr Val Ser Ser Ser Ser
65                  70                  75                  80

Ser Val Gly Gly Gly Ser Asp Gly Ser Gly Glu Ala Trp Arg Val Ile
                85                  90                  95

Pro Ala Ala Leu His Gly Pro Ala Thr Val Asp Val Gly Asn Ala Gly
            100                 105                 110

Thr Val Met Arg Phe Leu Pro Pro Val Ala Ala Leu Ala Asp Gly Pro
        115                 120                 125

Ile Arg Phe Asp Gly Asp Pro Arg Ser Tyr Glu Arg Pro Leu Asn Gly
    130                 135                 140

Val Ile Asp Ala Leu Arg Ala Leu Gly Ala Arg Ile Asp Asp Asp Gly
145                 150                 155                 160

Arg Gly Ala Leu Pro Leu Thr Val His Gly Gly Gly Ala Leu Asp Gly
                165                 170                 175

Gly Pro Val Ala Ile Asp Ala Ser Ser Ser Ser Gln Phe Val Ser Ala
            180                 185                 190

Leu Leu Leu Ser Gly Pro Arg Phe Asn Gln Gly Val Glu Val Arg His
        195                 200                 205

Thr Gly Ser Thr Leu Pro Ser Met Pro His Ile Arg Met Thr Val Asp
    210                 215                 220

Met Leu Arg Ala Val Gly Ala Gln Val Asp Thr Pro Glu Ser Gly Gly
225                 230                 235                 240

Glu Ala Asn Val Trp Arg Val Thr Pro Gly Ala Leu Leu Gly Arg Asp
                245                 250                 255

Leu Thr Val Glu Pro Asp Leu Ser Asn Ala Gln Pro Phe Leu Ala Ala
            260                 265                 270

Ala Leu Val Thr Gly Gly Lys Val Val Ile Pro Asp Trp Pro Glu Arg
        275                 280                 285

Thr Thr Gln Pro Gly Asp Lys Leu Arg Glu Ile Phe Thr Glu Met Gly
    290                 295                 300

Gly Ser Cys Glu Leu Thr Glu Gln Gly Leu Glu Phe Thr Gly Ser Gly
305                 310                 315                 320

Ala Val His Gly Ile Asp Val Asp Leu Ser Glu Val Gly Glu Leu Thr
                325                 330                 335

Pro Gly Ile Ala Ala Val Ala Ala Leu Ala Asp Ser Pro Ser Thr Leu
            340                 345                 350

Arg Gly Val Ala His Leu Arg Leu His Glu Thr Asp Arg Leu Ala Ala
        355                 360                 365

Leu Thr Lys Glu Ile Asn Glu Leu Gly Gly Asp Val Thr Glu Thr Ala
    370                 375                 380
```

-continued

```
Asp Gly Leu Ser Ile Arg Pro Arg Arg Leu His Gly Gly Ile Phe His
385                 390                 395                 400

Thr Tyr Asp Asp His Arg Met Ala Thr Ala Gly Ala Ile Ile Gly Leu
                405                 410                 415

Ala Val Asp Gly Val Gln Ile Glu Asn Val Ala Thr Thr Ala Lys Thr
            420                 425                 430

Leu Pro Asp Phe Pro Asp Leu Trp Thr Gly Met Leu Gly Asn
        435                 440                 445


<210> SEQ ID NO 26
<211> LENGTH: 447
<212> TYPE: PRT
<213> ORGANISM: Bacillus halodurans C-125

<400> SEQUENCE: 26

Met Thr Arg Phe Asp Glu Asn Ala Arg Ser Pro Trp Thr Pro Leu His
1               5                   10                  15

Asp Val Lys Thr Val Glu Leu Phe Pro Leu Asn Gln Arg Leu Asp Gly
            20                  25                  30

Ser Ile Thr Leu Pro Gly Ser Lys Ser Leu Thr Asn Arg Ala Leu Ile
        35                  40                  45

Ile Ser Ala Leu Ala Asn Ser Asp Ser Met Leu Thr Gly Met Leu Lys
    50                  55                  60

Ser Asp Asp Thr Tyr Trp Cys Ile Gln Ala Leu Lys Arg Leu Gly Val
65                  70                  75                  80

Gln Ile Asn Val Gln Gly Glu Thr Thr Ser Ile Arg Gly Ile Gly Gly
                85                  90                  95

Gln Trp Lys Ser Ser Ser Leu Tyr Ile Gly Ala Ala Gly Thr Leu Ala
            100                 105                 110

Arg Phe Leu Leu Gly Ala Leu Ala Ile Ser Arg Ser Gly Asn Trp Glu
        115                 120                 125

Ile Glu Ala Ser Gln Ser Met Ser Lys Arg Pro Ile Glu Pro Leu Val
    130                 135                 140

Gly Val Leu Arg Glu Leu Gly Ala Thr Ile His Tyr Leu Arg Arg Glu
145                 150                 155                 160

Gly Phe Tyr Pro Leu Ser Ile His Gly Asn Gly Leu Ala Gly Gly Thr
                165                 170                 175

Val Arg Leu Ser Gly Gln Met Ser Ser Gln Tyr Ile Ser Gly Leu Leu
            180                 185                 190

Ile Ala Ala Pro Tyr Ala Asp Thr Pro Val Thr Ile Thr Val Gln Gly
        195                 200                 205

Ser Ile Val Gln His Ala Tyr Val Phe Leu Thr Leu His Leu Met Lys
    210                 215                 220

Ser Phe Gly Ala Gln Val Glu Tyr Asp Gln Gln Leu Gln Thr Ile Val
225                 230                 235                 240

Val His Pro Thr Pro Tyr Thr Cys Gln Asp Ile Asp Leu Glu Ala Asp
                245                 250                 255

Ala Ser Thr Ala Cys Tyr Phe Leu Ala Leu Ala Ala Leu Thr Lys Gly
            260                 265                 270

Arg Ile Arg Leu Asn Asn Leu Thr Ala Ser Thr Thr Gln Pro Asp Leu
        275                 280                 285

His Met Leu Thr Val Phe Glu Lys Met Gly Cys Thr Val Thr Arg Gly
    290                 295                 300

Ser Ser Phe Ile Glu Leu Glu Gly Val Ser Gln Leu Lys Gly Gly Phe
305                 310                 315                 320
```

```
Gln Ile Ser Met Asn Glu Met Ser Asp Gln Ala Leu Thr Leu Ala Ala
                325                 330                 335

Ile Ala Pro Phe Ala Asp Gly Pro Ile Thr Ile Thr Asp Val Glu His
            340                 345                 350

Ile Arg Tyr His Glu Ser Asp Arg Ile Ala Val Ile Cys Glu Ala Leu
        355                 360                 365

Thr Arg Leu Gly Ile Gln Val Asp Glu Phe Glu Asp Gly Leu Thr Val
    370                 375                 380

Tyr Pro Gly Thr Pro Lys Pro Thr Leu His Pro Leu Ser Thr Tyr Asp
385                 390                 395                 400

Asp His Arg Val Ala Met Ser Leu Ser Leu Ile Gly Thr Lys Val Lys
                405                 410                 415

Gly Leu Arg Leu Asn Asp Pro Gly Cys Val Ala Lys Thr Cys Pro Ser
            420                 425                 430

Tyr Phe Gln Leu Leu Glu Gln Leu Gly Ile Gln Val His Tyr Gln
        435                 440                 445


<210> SEQ ID NO 27
<211> LENGTH: 446
<212> TYPE: PRT
<213> ORGANISM: Bacillus clausii KSM-K16

<400> SEQUENCE: 27

Met Val Gln Phe Asp Ser Gln Ala Arg Ser Pro Trp Thr Pro Leu Ala
1               5                   10                  15

Gly Val Glu Arg Leu Arg Leu Thr Pro Ser Gln Lys Arg Ile Asn Ala
            20                  25                  30

Thr Leu Glu Val Pro Gly Ser Lys Ser Ala Thr Asn Arg Ala Leu Leu
        35                  40                  45

Leu Ala Ala Val Ala Ser Gly Thr Ser Thr Leu Arg Asn Ala Leu Lys
    50                  55                  60

Ser Asp Asp Thr Tyr Trp Cys Ile Glu Ala Leu Lys Lys Thr Gly Val
65                  70                  75                  80

Glu Ile Ala Val Asp Gly Ser Asn Val Thr Val Tyr Gly Arg Gly Gly
                85                  90                  95

Val Phe His Ser Gly Ser Leu Tyr Ile Gly Ser Ala Gly Thr Ala Gly
            100                 105                 110

Arg Phe Leu Pro Gly Met Leu Ala Ala Ala Thr Gly Asn Trp His Val
        115                 120                 125

Glu Ala Ser His Ser Met Asn Lys Arg Pro Ile Ala Pro Leu Val Lys
    130                 135                 140

Thr Leu Gln Ala Leu Gly Ala Asn Ile Gln Tyr Gly Ser Arg Arg Gly
145                 150                 155                 160

His Tyr Pro Leu Ser Ile Ser Gly Glu Gly Leu Asn Gly Gly Lys Val
                165                 170                 175

Asn Met Ser Gly Gln Leu Ser Ser Gln Phe Ile Ser Gly Cys Leu Leu
            180                 185                 190

Ala Ala Pro Leu Ala Lys Asn Pro Val Ser Ile Thr Val Lys Asp Gly
        195                 200                 205

Ile Val Gln Gln Ala Tyr Val Arg Ile Thr Ile Asp Leu Met Ala Ala
    210                 215                 220

Phe Gly Val Glu Val Lys Ala Ala Pro Asp Trp Ser Leu Leu Glu Val
225                 230                 235                 240

Asn Pro Ser Pro Tyr Val Ala Asn Asp Ile Ala Ile Glu Ala Asp Ala
                245                 250                 255
```

```
Ser Thr Ala Cys Tyr Phe Leu Ala Leu Ala Ala Ile Thr Ala Gly Lys
            260                 265                 270

Ile Arg Ile Arg His Phe Ser Thr Lys Thr Ser Gln Pro Asp Ile Leu
        275                 280                 285

Phe Val Ser Ile Leu Lys Arg Met Gly Cys Asn Phe Glu Ile Gly Pro
    290                 295                 300

Ser Phe Val Glu Gly Glu Gly Pro Thr Arg Leu Arg Gly Gly Phe Thr
305                 310                 315                 320

Val Asn Met Asn Glu Leu Ser Asp Gln Ala Leu Thr Leu Ala Ala Ile
                325                 330                 335

Ser Pro Phe Ala Asp Gly Pro Ile Ala Ile Glu Gly Val Gly His Ile
            340                 345                 350

Arg His His Glu Cys Asp Arg Ile Arg Ala Ile Cys Thr Glu Leu Ser
        355                 360                 365

Arg Leu Gly Ile Arg Val Glu Glu Arg His Asp Gly Leu Thr Val Tyr
    370                 375                 380

Pro Gly Gln Pro Lys Pro Thr Val Val Asn Thr Tyr Asp Asp His Arg
385                 390                 395                 400

Met Ala Met Ala Leu Ala Leu Ile Gly Ala Lys Val Asp Gly Ile Glu
                405                 410                 415

Leu Asp Asp Pro Gly Cys Val Ala Lys Thr Cys Pro Ser Tyr Phe Ser
            420                 425                 430

Met Leu Ala Gln Thr Gly Ile Gly Val Lys Ala Val Ser Pro
        435                 440                 445


<210> SEQ ID NO 28
<211> LENGTH: 460
<212> TYPE: PRT
<213> ORGANISM: Arthrobacter sp. FB24

<400> SEQUENCE: 28

Met Thr Gly Thr Ala Pro Thr Glu Ser Ala Thr Ser Gly Pro Val Ala
1               5                   10                  15

Asp Val Pro His Trp Pro Ala Pro Phe Ala Glu Ala Pro Val Asp Ala
            20                  25                  30

Thr Val Thr Val Pro Gly Ser Lys Ser Leu Thr Asn Arg Tyr Leu Val
        35                  40                  45

Leu Ala Ala Leu Ala Asp Gly Pro Ser Arg Leu Arg Ala Pro Leu His
    50                  55                  60

Ser Arg Asp Ser Ala Leu Met Ile Glu Ala Leu Arg Gln Leu Gly Ala
65                  70                  75                  80

Gly Ile Arg Glu Val His Ser Asp Gly Ala Phe Gly Pro Asp Leu Glu
                85                  90                  95

Val Thr Pro Leu Arg Ala Asp Ala Ala Ala Thr Asp Ala Ala Ile Asp
            100                 105                 110

Cys Gly Leu Ala Gly Thr Val Met Arg Phe Val Pro Pro Val Ala Ala
        115                 120                 125

Leu Arg Asn Gly Ala Thr Val Phe Asp Gly Asp Pro His Ala Arg Lys
    130                 135                 140

Arg Pro Met Gly Thr Ile Ile Glu Ala Leu Ala Ala Leu Gly Val Asp
145                 150                 155                 160

Val Arg Ala Ala Asp Gly Thr Pro Pro Ser Ala Leu Pro Phe Thr Val
                165                 170                 175

Ala Gly Ser Gly His Val Arg Gly Gly His Leu Val Ile Asp Ala Ser
            180                 185                 190
```

-continued

```
Ala Ser Ser Gln Phe Val Ser Ala Leu Leu Leu Val Gly Ala Arg Phe
        195                 200                 205

Thr Glu Gly Leu His Leu Glu His Val Gly Lys Pro Val Pro Ser Leu
    210                 215                 220

Asp His Ile Asn Met Thr Val Ala Val Leu Arg Glu Val Gly Val Ser
225                 230                 235                 240

Val Asp Asp Ser Val Pro Asn His Trp Val Val Ala Pro Gly Arg Ile
                245                 250                 255

Arg Ala Phe Asp Arg Arg Ile Glu Gln Asp Leu Ser Asn Ala Gly Pro
            260                 265                 270

Phe Leu Ala Ala Ala Leu Ala Thr Arg Gly Thr Val Arg Ile Pro Asn
        275                 280                 285

Trp Pro Ser Pro Thr Thr Gln Val Gly Asp Leu Trp Arg Ser Ile Leu
    290                 295                 300

Thr Ala Met Gly Ala Thr Val Thr Leu Asp Asn Gly Thr Leu Thr Val
305                 310                 315                 320

Thr Gly Gly Pro Glu Ile Thr Gly Ala Asp Phe Ala Asp Thr Ser Glu
                325                 330                 335

Leu Ala Pro Thr Val Ala Ala Leu Cys Ala Leu Ala Thr Gly Pro Ser
            340                 345                 350

Arg Leu Thr Gly Ile Ala His Leu Arg Gly His Glu Thr Asp Arg Leu
        355                 360                 365

Ala Ala Leu Val Thr Glu Ile Asn Arg Leu Gly Gly Asp Ala Glu Glu
    370                 375                 380

Thr Ser Asp Gly Leu Val Ile Arg Pro Ala Lys Leu His Gly Gly Val
385                 390                 395                 400

Val His Ser Tyr Ala Asp His Arg Met Ala Thr Ala Gly Ala Ile Leu
                405                 410                 415

Gly Leu Ala Val Pro Gly Val Glu Val Glu Asp Ile Gly Thr Thr Ser
            420                 425                 430

Lys Thr Met Pro Asp Phe Pro Gln Leu Trp Glu Ser Met Leu Thr Gln
        435                 440                 445

Gln Pro Gly Arg Gln Thr Glu Gln Ala Arg Gly Ala
    450                 455                 460


<210> SEQ ID NO 29
<211> LENGTH: 419
<212> TYPE: PRT
<213> ORGANISM: Brevundomonas vesicularis

<400> SEQUENCE: 29

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Ala Leu Val Asp
            100                 105                 110
```

Gly Lys Val Ile Val Asp Gly Asp Ala His Met Arg Lys Arg Pro Ile
115 120 125

Gly Pro Leu Val Asp Ala Leu Arg Ser Leu Gly Ile Asp Ala Ser Ala
130 135 140

Glu Thr Gly Cys Pro Pro Val Thr Ile Asn Gly Thr Gly Arg Phe Glu
145 150 155 160

Ala Ser Arg Val Gln Ile Asp Gly Gly Leu Ser Ser Gln Tyr Val Ser
165 170 175

Ala Leu Leu Met Met Ala Ala Gly Gly Asp Arg Ala Val Asp Val Glu
180 185 190

Leu Leu Gly Glu His Ile Gly Ala Leu Gly Tyr Ile Asp Leu Thr Val
195 200 205

Ala Ala Met Arg Ala Phe Gly Ala Lys Val Glu Arg Val Ser Pro Val
210 215 220

Ala Trp Arg Val Glu Pro Thr Gly Tyr His Ala Ala Asp Phe Val Ile
225 230 235 240

Glu Pro Asp Ala Ser Ala Ala Thr Tyr Leu Trp Ala Ala Glu Val Leu
245 250 255

Ser Gly Gly Lys Ile Asp Leu Gly Thr Pro Ala Glu Gln Phe Ser Gln
260 265 270

Pro Asp Ala Lys Ala Tyr Asp Leu Ile Ser Lys Phe Pro His Leu Pro
275 280 285

Ala Val Ile Asp Gly Ser Gln Met Gln Asp Ala Ile Pro Thr Leu Ala
290 295 300

Val Leu Ala Ala Phe Asn Glu Met Pro Val Arg Phe Val Gly Ile Glu
305 310 315 320

Asn Leu Arg Val Lys Glu Cys Asp Arg Ile Arg Ala Leu Ser Ser Gly
325 330 335

Leu Ser Arg Ile Val Pro Asn Leu Gly Thr Glu Glu Gly Asp Asp Leu
340 345 350

Ile Ile Ala Ser Asp Pro Ser Leu Ala Gly Lys Ile Leu Thr Ala Glu
355 360 365

Ile Asp Ser Phe Ala Asp His Arg Ile Ala Met Ser Phe Ala Leu Ala
370 375 380

Gly Leu Lys Ile Gly Gly Ile Thr Ile Leu Asp Pro Asp Cys Val Ala
385 390 395 400

Lys Thr Phe Pro Ser Tyr Trp Asn Val Leu Ser Ser Leu Gly Val Ala
405 410 415

Tyr Glu Asp

<210> SEQ ID NO 30
<211> LENGTH: 444
<212> TYPE: PRT
<213> ORGANISM: Ochrobactrum/Brucella strain C58

<400> SEQUENCE: 30

Met Ala Cys Leu Pro Asp Asp Ser Gly Pro His Val Gly His Ser Thr
1 5 10 15

Pro Pro Cys Leu Asp Gln Glu Pro Cys Thr Leu Ser Ser Gln Lys Thr
20 25 30

Val Thr Val Thr Pro Pro Asn Phe Pro Leu Thr Gly Lys Val Ala Pro
35 40 45

Pro Gly Ser Lys Ser Ile Thr Asn Arg Ala Leu Leu Leu Ala Ala Leu
50 55 60

```
Ala Lys Gly Thr Ser Arg Leu Ser Gly Ala Leu Lys Ser Asp Asp Thr
65                  70                  75                  80

Arg His Met Ser Val Ala Leu Arg Gln Met Gly Val Thr Ile Asp Glu
                85                  90                  95

Pro Asp Asp Thr Thr Phe Val Val Thr Ser Gln Gly Ser Leu Gln Leu
            100                 105                 110

Pro Ala Gln Pro Leu Phe Leu Gly Asn Ala Gly Thr Ala Met Arg Phe
        115                 120                 125

Leu Thr Ala Ala Val Ala Thr Val Gln Gly Thr Val Val Leu Asp Gly
    130                 135                 140

Asp Glu Tyr Met Gln Lys Arg Pro Ile Gly Pro Leu Leu Ala Thr Leu
145                 150                 155                 160

Gly Gln Asn Gly Ile Gln Val Asp Ser Pro Thr Gly Cys Pro Pro Val
                165                 170                 175

Thr Val His Gly Ala Gly Lys Val Gln Ala Arg Arg Phe Glu Ile Asp
            180                 185                 190

Gly Gly Leu Ser Ser Gln Tyr Val Ser Ala Leu Leu Met Leu Ala Ala
        195                 200                 205

Cys Gly Glu Ala Pro Ile Glu Val Ala Leu Thr Gly Lys Asp Ile Gly
    210                 215                 220

Ala Arg Gly Tyr Val Asp Leu Thr Leu Asp Cys Met Arg Ala Phe Gly
225                 230                 235                 240

Ala Gln Val Asp Ile Val Asp Asp Thr Thr Trp Arg Val Ala Pro Thr
                245                 250                 255

Gly Tyr Thr Ala His Asp Tyr Leu Ile Glu Pro Asp Ala Ser Ala Ala
            260                 265                 270

Thr Tyr Leu Trp Ala Ala Glu Val Leu Thr Gly Gly Arg Ile Asp Ile
        275                 280                 285

Gly Val Ala Ala Gln Asp Phe Thr Gln Pro Asp Ala Lys Ala Gln Ala
    290                 295                 300

Val Ile Ala Gln Phe Pro Asn Met Gln Ala Thr Val Val Gly Ser Gln
305                 310                 315                 320

Met Gln Asp Ala Ile Pro Thr Leu Ala Val Leu Ala Ala Phe Asn Asn
                325                 330                 335

Thr Pro Val Arg Phe Thr Glu Leu Ala Asn Leu Arg Val Lys Glu Cys
            340                 345                 350

Asp Arg Val Gln Ala Leu His Asp Gly Leu Asn Glu Ile Arg Pro Gly
        355                 360                 365

Leu Ala Thr Ile Glu Gly Asp Asp Leu Leu Val Ala Ser Asp Pro Ala
    370                 375                 380

Leu Ala Gly Thr Ala Cys Thr Ala Leu Ile Asp Thr His Ala Asp His
385                 390                 395                 400

Arg Ile Ala Met Cys Phe Ala Leu Ala Gly Leu Lys Val Ser Gly Ile
                405                 410                 415

Arg Ile Gln Asp Pro Asp Cys Val Ala Lys Thr Tyr Pro Asp Tyr Trp
            420                 425                 430

Lys Ala Leu Ala Ser Leu Gly Val His Leu Ser Tyr
        435                 440
```

<210> SEQ ID NO 31
<211> LENGTH: 425
<212> TYPE: PRT
<213> ORGANISM: Agrobacterium tumefaciens strain C58

<400> SEQUENCE: 31

-continued

```
Met Ile Glu Leu Thr Ile Thr Pro Pro Gly His Pro Leu Ser Gly Lys
1               5                   10                  15

Val Glu Pro Pro Gly Ser Lys Ser Ile Thr Asn Arg Ala Leu Leu Leu
            20                  25                  30

Ala Gly Leu Ala Lys Gly Lys Ser Arg Leu Thr Gly Ala Leu Lys Ser
        35                  40                  45

Asp Asp Thr Leu Tyr Met Ala Glu Ala Leu Arg Glu Met Gly Val Lys
    50                  55                  60

Val Thr Glu Pro Asp Ala Thr Thr Phe Val Val Glu Ser Ser Gly Gly
65                  70                  75                  80

Leu His Gln Pro Glu Lys Pro Leu Phe Leu Gly Asn Ala Gly Thr Ala
                85                  90                  95

Thr Arg Phe Leu Thr Ala Ala Ala Ala Leu Val Asp Gly Ala Val Ile
            100                 105                 110

Ile Asp Gly Asp Glu His Met Arg Lys Arg Pro Ile Met Pro Leu Val
        115                 120                 125

Glu Ala Leu Arg Ser Leu Gly Val Glu Ala Glu Ala Pro Thr Gly Cys
    130                 135                 140

Pro Pro Val Thr Val Cys Gly Lys Gly Thr Gly Phe Pro Lys Gly Ser
145                 150                 155                 160

Val Thr Ile Asp Ala Asn Leu Ser Ser Gln Tyr Val Ser Ala Leu Leu
                165                 170                 175

Met Ala Ala Ala Cys Gly Asp Lys Pro Val Asp Ile Ile Leu Lys Gly
            180                 185                 190

Glu Glu Ile Gly Ala Lys Gly Tyr Ile Asp Leu Thr Thr Ser Ala Met
        195                 200                 205

Glu Ala Phe Gly Ala Lys Val Glu Arg Val Ser Asn Ala Ile Trp Arg
    210                 215                 220

Val His Pro Thr Gly Tyr Thr Ala Thr Asp Phe His Ile Glu Pro Asp
225                 230                 235                 240

Ala Ser Ala Ala Thr Tyr Leu Trp Gly Ala Glu Leu Leu Thr Gly Gly
                245                 250                 255

Ala Ile Asp Ile Gly Thr Pro Ala Asp Lys Phe Thr Gln Pro Asp Ala
            260                 265                 270

Lys Ala His Glu Val Met Ala Gln Phe Pro His Leu Pro Ala Glu Ile
        275                 280                 285

Asp Gly Ser Gln Met Gln Asp Ala Ile Pro Thr Ile Ala Val Leu Ala
    290                 295                 300

Ala Phe Asn Glu Thr Pro Val Arg Phe Val Gly Ile Ala Asn Leu Arg
305                 310                 315                 320

Val Lys Glu Cys Asp Arg Ile Arg Ala Val Ser Leu Gly Leu Asn Glu
                325                 330                 335

Ile Arg Asp Gly Leu Ala His Glu Glu Gly Asp Asp Leu Ile Val His
            340                 345                 350

Ser Asp Pro Ser Leu Ala Gly Gln Thr Val Asn Ala Ser Ile Asp Thr
        355                 360                 365

Phe Ala Asp His Arg Ile Ala Met Ser Phe Ala Leu Ala Ala Leu Lys
    370                 375                 380

Ile Gly Gly Ile Ala Ile Gln Asn Pro Ala Cys Val Gly Lys Thr Tyr
385                 390                 395                 400

Pro Gly Tyr Trp Lys Ala Leu Ala Ser Leu Gly Val Glu Tyr Ser Glu
                405                 410                 415

Lys Glu Thr Ala Ala Glu Pro Gln His
            420                 425
```

<210> SEQ ID NO 32
<211> LENGTH: 418
<212> TYPE: PRT
<213> ORGANISM: Pseudomonas syringae strain 1448a

<400> SEQUENCE: 32

```
Met Arg Pro Gln Ala Thr Leu Thr Val Leu Pro Val Glu Arg Pro Leu
1               5                   10                  15

Val Gly Arg Val Ser Pro Pro Gly Ser Lys Ser Ile Thr Asn Arg Ala
            20                  25                  30

Leu Leu Leu Ala Gly Leu Ala Lys Gly Thr Ser Arg Leu Thr Gly Ala
        35                  40                  45

Leu Lys Ser Asp Asp Thr Arg Val Met Ser Glu Ala Leu Arg Leu Met
    50                  55                  60

Gly Val Gln Val Asp Glu Pro Asp Asp Ser Thr Phe Val Val Thr Ser
65                  70                  75                  80

Ser Gly His Trp Gln Ala Pro Gln Gln Ala Leu Phe Leu Gly Asn Ala
                85                  90                  95

Gly Thr Ala Thr Arg Phe Leu Thr Ala Ala Leu Ala Asn Phe Glu Gly
            100                 105                 110

Asp Phe Val Val Asp Gly Asp Glu Tyr Met Arg Lys Arg Pro Ile Gly
        115                 120                 125

Pro Leu Val Asp Ala Leu Gln Arg Met Gly Val Glu Val Ser Ala Pro
    130                 135                 140

Ser Gly Cys Pro Pro Val Ala Ile Lys Gly Lys Gly Gly Leu Glu Ala
145                 150                 155                 160

Gly Arg Ile Glu Ile Asp Gly Asn Leu Ser Ser Gln Tyr Val Ser Ala
                165                 170                 175

Leu Leu Met Ala Gly Ala Cys Gly Lys Gly Pro Val Glu Val Ala Leu
            180                 185                 190

Thr Gly Ser Glu Ile Gly Ala Arg Gly Tyr Val Asp Leu Thr Leu Ala
        195                 200                 205

Ala Met Gln Ala Phe Gly Ala Glu Val Gln Ala Ile Gly Glu Thr Ala
    210                 215                 220

Trp Lys Val Ser Ala Thr Gly Tyr Arg Ala Thr Asp Phe His Ile Glu
225                 230                 235                 240

Pro Asp Ala Ser Ala Ala Thr Tyr Leu Trp Ala Ala Gln Ala Leu Thr
                245                 250                 255

Glu Gly Asp Ile Asp Leu Gly Val Ala Ser Asp Ala Phe Thr Gln Pro
            260                 265                 270

Asp Ala Leu Ala Ser Gln Ile Ile Ala Ser Phe Pro Asn Met Pro Ala
        275                 280                 285

Val Ile Asp Gly Ser Gln Met Gln Asp Ala Ile Pro Thr Leu Ala Val
    290                 295                 300

Leu Ala Ala Phe Asn Arg Gln Pro Val Arg Phe Val Gly Ile Ala Asn
305                 310                 315                 320

Leu Arg Val Lys Glu Cys Asp Arg Ile Ser Ala Leu Ser His Gly Leu
                325                 330                 335

Cys Ala Ile Ala Pro Gly Leu Ala Val Glu Glu Gly Asp Asp Leu Leu
            340                 345                 350

Val His Ala Asn Pro Ala Leu Ala Gly Thr Thr Val Asp Ala Leu Ile
        355                 360                 365

Asp Thr His Ser Asp His Arg Ile Ala Met Cys Phe Ala Leu Ala Gly
    370                 375                 380
```

```
Leu Lys Ile Ala Gly Ile Arg Ile Leu Asp Pro Asp Cys Val Gly Lys
385                 390                 395                 400

Thr Tyr Pro Gly Tyr Trp Asp Ala Leu Ala Ser Leu Gly Val Arg Val
                405                 410                 415

Gln Arg


<210> SEQ ID NO 33
<211> LENGTH: 418
<212> TYPE: PRT
<213> ORGANISM: Pseudomonas syringae strain DC3000

<400> SEQUENCE: 33

Met Arg Pro Gln Ala Thr Leu Thr Val Met Pro Val Glu Arg Pro Leu
1               5                   10                  15

Val Gly Arg Val Ser Pro Pro Gly Ser Lys Ser Ile Thr Asn Arg Ala
            20                  25                  30

Leu Leu Leu Ala Gly Leu Ala Lys Gly Thr Ser Arg Leu Thr Gly Ala
        35                  40                  45

Leu Lys Ser Asp Asp Thr Arg Val Met Ser Glu Ala Leu Arg Leu Met
    50                  55                  60

Gly Val Gln Val Asp Glu Pro Asp Asp Ser Thr Phe Val Val Thr Ser
65                  70                  75                  80

Ser Gly His Trp Gln Ala Pro Gln Gln Ala Leu Phe Leu Gly Asn Ala
                85                  90                  95

Gly Thr Ala Thr Arg Phe Leu Thr Ala Ala Leu Ala Asn Phe Glu Gly
            100                 105                 110

Asp Phe Val Val Asp Gly Asp Glu Tyr Met Arg Lys Arg Pro Ile Gly
        115                 120                 125

Pro Leu Val Asp Ala Leu Gln Arg Met Gly Val Glu Ile Ser Ala Pro
    130                 135                 140

Ser Gly Cys Pro Pro Val Ala Ile Lys Gly Lys Gly Gly Leu Gln Ala
145                 150                 155                 160

Gly Arg Ile Glu Ile Asp Gly Asn Leu Ser Ser Gln Tyr Val Ser Ala
                165                 170                 175

Leu Leu Met Ala Gly Ala Cys Gly Lys Gly Ser Leu Glu Val Ala Leu
            180                 185                 190

Thr Gly Ser Glu Ile Gly Ala Arg Gly Tyr Val Asp Leu Thr Leu Ala
        195                 200                 205

Ala Met Gln Ala Phe Gly Ala Glu Val Gln Ala Ile Gly Asp Ala Ala
    210                 215                 220

Trp Lys Val Ser Ala Thr Gly Tyr His Ala Thr Asp Phe His Ile Glu
225                 230                 235                 240

Pro Asp Ala Ser Ala Ala Thr Tyr Leu Trp Ala Ala Gln Ala Leu Thr
                245                 250                 255

Glu Gly Asn Ile Asp Leu Gly Val Ala Ser Asp Ala Phe Thr Gln Pro
            260                 265                 270

Asp Ala Leu Ala Ser Gln Ile Ile Asp Ser Phe Pro Asn Met Pro Ala
        275                 280                 285

Val Ile Asp Gly Ser Gln Met Gln Asp Ala Ile Pro Thr Leu Ala Val
    290                 295                 300

Leu Ala Ala Phe Asn Arg Gln Pro Val Arg Phe Val Gly Ile Ala Asn
305                 310                 315                 320

Leu Arg Val Lys Glu Cys Asp Arg Ile Ser Ala Leu Cys Asp Gly Leu
                325                 330                 335
```

Cys Ala Ile Ala Pro Gly Leu Ala Val Glu Glu Gly Asp Asp Leu Ile
340 345 350

Val His Ala Asn Pro Ala Leu Ala Gly Thr Thr Val Asn Ala Leu Ile
355 360 365

Asp Thr His Ser Asp His Arg Ile Ala Met Cys Phe Ala Leu Ala Gly
370 375 380

Leu Lys Ile Lys Gly Ile His Ile Gln Asp Pro Asp Cys Val Ala Lys
385 390 395 400

Thr Tyr Pro Gly Tyr Trp Asp Ala Leu Ala Ser Leu Gly Val Ser Val
405 410 415

Gln Arg

<210> SEQ ID NO 34
<211> LENGTH: 418
<212> TYPE: PRT
<213> ORGANISM: Pseudomonas syringae strain B728

<400> SEQUENCE: 34

Met Arg Pro Gln Ala Thr Leu Thr Val Leu Pro Val Glu Arg Pro Leu
1 5 10 15

Val Gly Arg Val Ser Pro Pro Gly Ser Lys Ser Ile Thr Asn Arg Ala
20 25 30

Leu Leu Leu Ala Gly Leu Ala Lys Gly Thr Ser Arg Leu Thr Gly Ala
35 40 45

Leu Lys Ser Asp Asp Thr Arg Val Met Ser Glu Ala Leu Arg Leu Met
50 55 60

Gly Val Gln Val Asp Glu Pro Asp Asp Ser Thr Phe Val Val Thr Ser
65 70 75 80

Ser Gly His Trp Gln Ala Pro Gln Gln Ala Leu Phe Leu Gly Asn Ala
85 90 95

Gly Thr Ala Thr Arg Phe Leu Thr Ala Ala Leu Ala Asn Phe Glu Gly
100 105 110

Asp Phe Val Val Asp Gly Asp Glu Tyr Met Arg Lys Arg Pro Ile Gly
115 120 125

Pro Leu Val Asp Ala Leu Gln Arg Met Gly Val Glu Val Ser Ala Pro
130 135 140

Ser Gly Cys Pro Pro Val Ala Ile Lys Gly Lys Gly Gly Leu Glu Ala
145 150 155 160

Gly Arg Ile Glu Ile Asp Gly Asn Leu Ser Ser Gln Tyr Val Ser Ala
165 170 175

Leu Leu Met Ala Gly Ala Cys Gly Lys Gly Pro Val Glu Val Ala Leu
180 185 190

Thr Gly Ser Glu Ile Gly Ala Arg Gly Tyr Leu Asp Leu Thr Leu Ala
195 200 205

Ala Met Arg Ala Phe Gly Ala Glu Val Gln Ala Ile Gly Asp Ala Ala
210 215 220

Trp Lys Val Ser Ala Thr Gly Tyr Arg Ala Thr Asp Phe His Ile Glu
225 230 235 240

Pro Asp Ala Ser Ala Ala Thr Tyr Leu Trp Ala Ala Gln Ala Leu Thr
245 250 255

Glu Gly Ala Ile Asp Leu Gly Val Ala Ser Asn Ala Phe Thr Gln Pro
260 265 270

Asp Ala Leu Ala Ser Gln Ile Ile Ala Ser Phe Pro Asn Met Pro Ala
275 280 285

Val Ile Asp Gly Ser Gln Met Gln Asp Ala Ile Pro Thr Leu Ala Val

```
    290                 295                 300

Leu Ala Ala Phe Asn Arg Gln Pro Val Arg Phe Val Gly Ile Ala Asn
305                 310                 315                 320

Leu Arg Val Lys Glu Cys Asp Arg Ile Ser Ala Leu Ser Asn Gly Leu
                325                 330                 335

Cys Ala Ile Ala Pro Gly Leu Ala Val Glu Glu Gly Asp Asp Leu Ile
            340                 345                 350

Val Thr Ala Asn Pro Thr Leu Ala Gly Thr Thr Val Asp Ala Leu Ile
        355                 360                 365

Asp Thr His Ser Asp His Arg Ile Ala Met Cys Phe Ala Leu Ala Gly
    370                 375                 380

Leu Lys Ile Ala Gly Ile Arg Ile Leu Asp Pro Asp Cys Val Ala Lys
385                 390                 395                 400

Thr Tyr Pro Gly Tyr Trp Asp Ala Leu Ala Ser Leu Gly Val Ser Val
                405                 410                 415

Gln Arg


<210> SEQ ID NO 35
<211> LENGTH: 425
<212> TYPE: PRT
<213> ORGANISM: Agrobacterium tumefaciens strain C58

<400> SEQUENCE: 35

Met Ile Glu Leu Thr Ile Thr Pro Pro Gly His Pro Leu Ser Gly Lys
1               5                   10                  15

Val Glu Pro Pro Gly Ser Lys Ser Ile Thr Asn Arg Ala Leu Leu Leu
            20                  25                  30

Ala Gly Leu Ala Lys Gly Lys Ser His Leu Ser Gly Ala Leu Lys Ser
        35                  40                  45

Asp Asp Thr Leu Tyr Met Ala Glu Ala Leu Arg Glu Met Gly Val Lys
    50                  55                  60

Val Thr Glu Pro Asp Ala Thr Thr Phe Val Val Glu Gly Thr Gly Val
65                  70                  75                  80

Leu Gln Gln Pro Glu Lys Pro Leu Phe Leu Gly Asn Ala Gly Thr Ala
                85                  90                  95

Thr Arg Phe Leu Thr Ala Ala Gly Ala Leu Val Asp Gly Ala Val Ile
            100                 105                 110

Ile Asp Gly Asp Glu His Met Arg Lys Arg Pro Ile Leu Pro Leu Val
        115                 120                 125

Gln Ala Leu Arg Ala Leu Gly Val Glu Ala Asp Ala Pro Thr Gly Cys
    130                 135                 140

Pro Pro Val Thr Val Arg Gly Lys Gly Met Gly Phe Pro Lys Gly Ser
145                 150                 155                 160

Val Thr Ile Asp Ala Asn Leu Ser Ser Gln Tyr Val Ser Ala Leu Leu
                165                 170                 175

Met Ala Ala Ala Cys Gly Asp Lys Pro Val Asp Ile Ile Leu Lys Gly
            180                 185                 190

Glu Glu Ile Gly Ala Lys Gly Tyr Ile Asp Leu Thr Thr Ser Ala Met
        195                 200                 205

Glu Ala Phe Gly Ala Lys Val Glu Arg Val Ser Asn Ala Ile Trp Arg
    210                 215                 220

Val His Pro Thr Gly Tyr Thr Ala Thr Asp Phe His Ile Glu Pro Asp
225                 230                 235                 240

Ala Ser Ala Ala Thr Tyr Leu Trp Gly Ala Glu Leu Leu Thr Gly Gly
                245                 250                 255
```

```
Ala Ile Asp Ile Gly Thr Pro Ala Asp Lys Phe Thr Gln Pro Asp Ala
            260                 265                 270

Lys Ala Tyr Glu Val Met Ala Gln Phe Pro His Leu Pro Ala Glu Ile
        275                 280                 285

Asp Gly Ser Gln Met Gln Asp Ala Ile Pro Thr Ile Ala Val Ile Ala
    290                 295                 300

Ala Phe Asn Glu Thr Pro Val Arg Phe Val Gly Ile Ala Asn Leu Arg
305                 310                 315                 320

Val Lys Glu Cys Asp Arg Ile Arg Ala Val Ser Leu Gly Leu Asn Glu
                325                 330                 335

Ile Arg Glu Gly Leu Ala His Glu Glu Gly Asp Asp Leu Ile Val His
            340                 345                 350

Ala Asp Pro Ser Leu Ala Gly Gln Thr Val Asp Ala Ser Ile Asp Thr
        355                 360                 365

Phe Ala Asp His Arg Ile Ala Met Ser Phe Ala Leu Ala Ala Leu Lys
    370                 375                 380

Ile Gly Gly Ile Ala Ile Gln Asn Pro Ala Cys Val Ala Lys Thr Tyr
385                 390                 395                 400

Pro Gly Tyr Trp Lys Ala Leu Ala Ser Leu Gly Val Asp Tyr Thr Glu
                405                 410                 415

Lys Glu Ser Ala Ala Glu Pro Gln His
            420                 425


<210> SEQ ID NO 36
<211> LENGTH: 444
<212> TYPE: PRT
<213> ORGANISM: Unknown
<220> FEATURE:
<223> OTHER INFORMATION: Isolated from soil sample

<400> SEQUENCE: 36

Met Ala Cys Leu Pro Asp Asp Ser Gly Pro His Val Gly His Ser Thr
1               5                   10                  15

Pro Pro Arg Leu Asp Gln Glu Pro Cys Thr Leu Ser Ser Gln Lys Thr
            20                  25                  30

Val Thr Val Thr Pro Pro Asn Phe Pro Leu Thr Gly Lys Val Ala Pro
        35                  40                  45

Pro Gly Ser Lys Ser Ile Thr Asn Arg Ala Leu Leu Leu Ala Ala Leu
    50                  55                  60

Ala Lys Gly Thr Ser Arg Leu Ser Gly Ala Leu Lys Ser Asp Asp Thr
65                  70                  75                  80

Arg His Met Ser Val Ala Leu Arg Gln Met Gly Val Thr Ile Asp Glu
                85                  90                  95

Pro Asp Asp Thr Thr Phe Val Val Thr Ser Gln Gly Ser Leu Gln Leu
            100                 105                 110

Pro Ala Gln Pro Leu Phe Leu Gly Asn Ala Gly Thr Ala Met Arg Phe
        115                 120                 125

Leu Thr Ala Ala Val Ala Thr Val Gln Gly Thr Val Val Leu Asp Gly
    130                 135                 140

Asp Glu Tyr Met Gln Lys Arg Pro Ile Gly Pro Leu Leu Ala Thr Leu
145                 150                 155                 160

Gly Gln Asn Gly Ile Gln Val Asp Ser Pro Thr Gly Cys Pro Pro Val
                165                 170                 175

Thr Val His Gly Met Gly Lys Val Gln Ala Lys Arg Phe Glu Ile Asp
            180                 185                 190
```

```
Gly Gly Leu Ser Ser Gln Tyr Val Ser Ala Leu Leu Met Leu Ala Ala
        195                 200                 205

Cys Gly Glu Ala Pro Ile Glu Val Ala Leu Thr Gly Lys Asp Ile Gly
    210                 215                 220

Ala Arg Gly Tyr Val Asp Leu Thr Leu Asp Cys Met Arg Ala Phe Gly
225                 230                 235                 240

Ala Gln Val Asp Ala Val Asp Asp Thr Thr Trp Arg Val Ala Pro Thr
                245                 250                 255

Gly Tyr Thr Ala His Asp Tyr Leu Ile Glu Pro Asp Ala Ser Ala Ala
            260                 265                 270

Thr Tyr Leu Trp Ala Ala Glu Val Leu Thr Gly Gly Arg Ile Asp Ile
        275                 280                 285

Gly Val Ala Ala Gln Asp Phe Thr Gln Pro Asp Ala Lys Ala Gln Ala
    290                 295                 300

Val Ile Ala Gln Phe Pro Asn Met Gln Ala Thr Val Val Gly Ser Gln
305                 310                 315                 320

Met Gln Asp Ala Ile Pro Thr Leu Ala Val Leu Ala Ala Phe Asn Asn
                325                 330                 335

Thr Pro Val Arg Phe Thr Glu Leu Ala Asn Leu Arg Val Lys Glu Cys
            340                 345                 350

Asp Arg Val Gln Ala Leu His Asp Gly Leu Asn Glu Ile Arg Pro Gly
        355                 360                 365

Leu Ala Thr Ile Glu Gly Asp Asp Leu Leu Val Ala Ser Asp Pro Ala
    370                 375                 380

Leu Ala Gly Thr Ala Cys Thr Ala Leu Ile Asp Thr His Ala Asp His
385                 390                 395                 400

Arg Ile Ala Met Cys Phe Ala Leu Ala Gly Leu Lys Val Ser Gly Ile
                405                 410                 415

Arg Ile Gln Asp Pro Asp Cys Val Ala Lys Thr Tyr Pro Asp Tyr Trp
            420                 425                 430

Lys Ala Trp Pro Ser Leu Gly Val His Leu Asn Asp
        435                 440


<210> SEQ ID NO 37
<211> LENGTH: 427
<212> TYPE: PRT
<213> ORGANISM: Escherichia coli

<400> SEQUENCE: 37

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
        35                  40                  45

Asp Val Arg His Met Leu Asn Ala Leu Thr Ala Leu Gly Val Ser Tyr
    50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
                85                  90                  95

Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125
```

```
Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Glu Lys Leu Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
            420                 425


<210> SEQ ID NO 38
<211> LENGTH: 444
<212> TYPE: PRT
<213> ORGANISM: Zea mays

<400> SEQUENCE: 38

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80
```

```
Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440
```

<210> SEQ ID NO 39
<211> LENGTH: 455
<212> TYPE: PRT
<213> ORGANISM: Agrobacterium sp. CP4

<400> SEQUENCE: 39

```
Met Ser His Gly Ala Ser Ser Arg Pro Ala Thr Ala Arg Lys Ser Ser
1               5                   10                  15
```

-continued

```
Gly Leu Ser Gly Thr Val Arg Ile Pro Gly Asp Lys Ser Ile Ser His
            20                  25                  30

Arg Ser Phe Met Phe Gly Gly Leu Ala Ser Gly Glu Thr Arg Ile Thr
        35                  40                  45

Gly Leu Leu Glu Gly Glu Asp Val Ile Asn Thr Gly Lys Ala Met Gln
    50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
    130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285

Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
                405                 410                 415

Ser Glu Asn Pro Val Thr Val Asp Asp Ala Thr Met Ile Ala Thr Ser
            420                 425                 430

Phe Pro Glu Phe Met Asp Leu Met Ala Gly Leu Gly Ala Lys Ile Glu
        435                 440                 445
```

```
Leu Ser Asp Thr Lys Ala Ala
    450                 455


<210> SEQ ID NO 40
<211> LENGTH: 428
<212> TYPE: PRT
<213> ORGANISM: Bacillus subtilis

<400> SEQUENCE: 40

Met Lys Arg Asp Lys Val Gln Thr Leu His Gly Glu Ile His Ile Pro
1               5                   10                  15

Gly Asp Lys Ser Ile Ser His Arg Ser Val Met Phe Gly Ala Leu Ala
            20                  25                  30

Ala Gly Thr Thr Thr Val Lys Asn Phe Leu Pro Gly Ala Asp Cys Leu
        35                  40                  45

Ser Thr Ile Asp Cys Phe Arg Lys Met Gly Val His Ile Glu Gln Ser
    50                  55                  60

Ser Ser Asp Val Val Ile His Gly Lys Gly Ile Asp Ala Leu Lys Glu
65                  70                  75                  80

Pro Glu Ser Leu Leu Asp Val Gly Asn Ser Gly Thr Thr Ile Arg Leu
                85                  90                  95

Met Leu Gly Ile Leu Ala Gly Arg Pro Phe Tyr Ser Ala Val Ala Gly
            100                 105                 110

Asp Glu Ser Ile Ala Lys Arg Pro Met Lys Arg Val Thr Glu Pro Leu
        115                 120                 125

Lys Lys Met Gly Ala Lys Ile Asp Gly Arg Ala Gly Gly Glu Phe Thr
    130                 135                 140

Pro Leu Ser Val Ser Gly Ala Ser Leu Lys Gly Ile Asp Tyr Val Ser
145                 150                 155                 160

Pro Val Ala Ser Ala Gln Ile Lys Ser Ala Val Leu Leu Ala Gly Leu
                165                 170                 175

Gln Ala Glu Gly Thr Thr Thr Val Thr Glu Pro His Lys Ser Arg Asp
            180                 185                 190

His Thr Glu Arg Met Leu Ser Ala Phe Gly Val Lys Leu Ser Glu Asp
        195                 200                 205

Gln Thr Ser Val Ser Ile Ala Gly Gly Gln Lys Leu Thr Ala Ala Asp
    210                 215                 220

Ile Phe Val Pro Gly Asp Ile Ser Ser Ala Ala Phe Phe Leu Ala Ala
225                 230                 235                 240

Gly Ala Met Val Pro Asn Ser Arg Ile Val Leu Lys Asn Val Gly Leu
                245                 250                 255

Asn Pro Thr Arg Thr Gly Ile Ile Asp Val Leu Gln Asn Met Gly Ala
            260                 265                 270

Lys Leu Glu Ile Lys Pro Ser Ala Asp Ser Gly Ala Glu Pro Tyr Gly
        275                 280                 285

Asp Leu Ile Ile Glu Thr Ser Ser Leu Lys Ala Val Glu Ile Gly Gly
    290                 295                 300

Asp Ile Ile Pro Arg Leu Ile Asp Glu Ile Pro Ile Ile Ala Leu Leu
305                 310                 315                 320

Ala Thr Gln Ala Glu Gly Thr Thr Val Ile Lys Asp Ala Ala Glu Leu
                325                 330                 335

Lys Val Lys Glu Thr Asn Arg Ile Asp Thr Val Val Ser Glu Leu Arg
            340                 345                 350

Lys Leu Gly Ala Glu Ile Glu Pro Thr Ala Asp Gly Met Lys Val Tyr
        355                 360                 365
```

Gly Lys Gln Thr Leu Lys Gly Gly Ala Ala Val Ser Ser His Gly Asp
    370                 375                 380

His Arg Ile Gly Met Met Leu Gly Ile Ala Ser Cys Ile Thr Glu Glu
385                 390                 395                 400

Pro Ile Glu Ile Glu His Thr Asp Ala Ile His Val Ser Tyr Pro Thr
                405                 410                 415

Phe Phe Glu His Leu Asn Lys Leu Ser Lys Lys Ser
            420                 425

<210> SEQ ID NO 41
<211> LENGTH: 431
<212> TYPE: PRT
<213> ORGANISM: Enterobacteriaceae

<400> SEQUENCE: 41

Met Lys Val Thr Ile Gln Pro Gly Asp Leu Thr Gly Ile Leu Gln Ser
1               5                   10                  15

Pro Ala Ser Lys Ser Ser Met Gln Arg Ala Cys Ala Ala Ala Leu Val
            20                  25                  30

Ala Lys Gly Ile Ser Glu Ile Ile Asn Pro Gly His Ser Asn Asp Asp
        35                  40                  45

Lys Ala Ala Arg Asp Ile Val Ser Arg Leu Gly Ala Arg Leu Glu Asp
    50                  55                  60

Gln Pro Asp Gly Ser Leu Gln Ile Thr Ser Glu Gly Val Lys Pro Val
65                  70                  75                  80

Ala Pro Phe Ile Asp Cys Gly Glu Ser Gly Leu Ser Ile Arg Met Phe
                85                  90                  95

Thr Pro Ile Val Ala Leu Ser Lys Glu Glu Val Thr Ile Lys Gly Ser
            100                 105                 110

Gly Ser Leu Val Thr Arg Pro Met Asp Phe Phe Asp Glu Ile Leu Pro
        115                 120                 125

His Leu Gly Val Lys Val Lys Ser Asn Gln Gly Lys Leu Pro Leu Val
    130                 135                 140

Ile Gln Gly Pro Leu Lys Pro Ala Asp Val Thr Val Asp Gly Ser Leu
145                 150                 155                 160

Ser Ser Gln Phe Leu Thr Gly Leu Leu Leu Ala Tyr Ala Ala Ala Asp
                165                 170                 175

Ala Ser Asp Val Ala Ile Lys Val Thr Asn Leu Lys Ser Arg Pro Tyr
            180                 185                 190

Ile Asp Leu Thr Leu Asp Val Met Lys Arg Phe Gly Leu Lys Thr Pro
        195                 200                 205

Glu Asn Arg Asn Tyr Glu Glu Phe Tyr Phe Lys Ala Gly Asn Val Tyr
    210                 215                 220

Asp Glu Thr Lys Met Gln Arg Tyr Thr Val Glu Gly Asp Trp Ser Gly
225                 230                 235                 240

Gly Ala Phe Leu Leu Val Ala Gly Ala Ile Ala Gly Pro Ile Thr Val
                245                 250                 255

Arg Gly Leu Asp Ile Ala Ser Thr Gln Ala Asp Lys Ala Ile Val Gln
            260                 265                 270

Ala Leu Met Ser Ala Asn Ala Gly Ile Ala Ile Asp Ala Lys Glu Ile
        275                 280                 285

Lys Leu His Pro Ala Asp Leu Asn Ala Phe Glu Phe Asp Ala Thr Asp
    290                 295                 300

Cys Pro Asp Leu Phe Pro Pro Leu Val Ala Leu Ala Ser Tyr Cys Lys
305                 310                 315                 320

-continued

```
Gly Glu Thr Lys Ile Lys Gly Val Ser Arg Leu Ala His Lys Glu Ser
                325                 330                 335

Asp Arg Gly Leu Thr Leu Gln Asp Glu Phe Gly Lys Met Gly Val Glu
            340                 345                 350

Ile His Leu Glu Gly Asp Leu Met Arg Val Ile Gly Gly Lys Gly Val
        355                 360                 365

Lys Gly Ala Glu Val Ser Ser Arg His Asp His Arg Ile Ala Met Ala
    370                 375                 380

Cys Ala Val Ala Ala Leu Lys Ala Val Gly Glu Thr Thr Ile Glu His
385                 390                 395                 400

Ala Glu Ala Val Asn Lys Ser Tyr Pro Asp Phe Tyr Ser Asp Leu Lys
                405                 410                 415

Gln Leu Gly Gly Val Val Ser Leu Asn His Gln Phe Asn Phe Ser
            420                 425                 430
```